United States Patent
Disingrini et al.

(10) Patent No.: US 9,127,015 B2
(45) Date of Patent: Sep. 8, 2015

(54) TRICYCLOPYRAZOLE DERIVATIVES

(75) Inventors: Teresa Disingrini, Vanzago (IT); Sergio Mantegani, Milan (IT); Mario Varasi, Milan (IT)

(73) Assignee: NERVIANO MEDICAL SCIENCES S.R.L., Nerviano (IT)

( * ) Notice: Subject to any disclaimer, the term of this patent is extended or adjusted under 35 U.S.C. 154(b) by 360 days.

(21) Appl. No.: 13/512,904

(22) PCT Filed: Nov. 24, 2010

(86) PCT No.: PCT/EP2010/068129
§ 371 (c)(1),
(2), (4) Date: Jul. 17, 2012

(87) PCT Pub. No.: WO2011/067145
PCT Pub. Date: Jun. 9, 2011

(65) Prior Publication Data
US 2012/0277214 A1 Nov. 1, 2012

(30) Foreign Application Priority Data
Dec. 4, 2009 (EP) .................................... 09178074

(51) Int. Cl.
*A61K 31/437* (2006.01)
*C07D 471/14* (2006.01)
*C07D 487/14* (2006.01)

(52) U.S. Cl.
CPC .................................... *C07D 487/14* (2013.01)

(58) Field of Classification Search
CPC ........................... A61K 31/437; C07D 471/14
USPC ............................................ 514/293; 546/82
See application file for complete search history.

(56) References Cited

FOREIGN PATENT DOCUMENTS

| EP | 0154142 A1 | 9/1985 |
|---|---|---|
| EP | 1 746 100 A1 | 1/2007 |
| WO | WO 96/39408 | 12/1996 |
| WO | WO 02/48144 A1 | 6/2002 |

OTHER PUBLICATIONS

International Search Report dated Feb. 4, 2011 issued in PCT/EP2010/068129.
Cohen P. et al., "The Development and Therapeutic Potential of Protein Kinase Inhibitors", Current Opinion in Chemical Biology 3:459-465 (1999).
Velculescu V.E., "Defining the Blueprint of the Cancer Genome", Carcinogenesis 29(6):1087-1091 (2008).
Gueiffier A. et al., "Synthesis of 1H-Imidazo[1,2-a]Pyrazolo[3,4-c]Pyridines", Chem. Pharm. Bull. 38(9):2352-2356 (1990).
Anderson W.K. et al., "Synthesis and Antileukemic Activity of Bis[[(Carbamoyl)Oxyl]Methyl]-Substituted Pyrrolo[2,1-a]Isoquinolines, Pyrrolo[1,2-a]Quinolines, Pyrrolo[2,1-a]Isobenzazepines, and Pyrrolo[1,2-a]Benzazepines", J. Med. Chem. 31(11):2097-2102 (1988).
Nishiwaki E. et al., "Efficient Synthesis of Oligo-N-Methylpyrrolecarboxamides and Related Compounds", Heterocycles 27(8):1945-1952 (1988).
Freedlander R.S. et al., "Neutral Trichloroacetylations of Alcohols by Hexachloracetone", J. Org. Chem. 46:3519-3521 (1981).
Harbuck J.W. et al., "Facile Introduction of Ester Groups into the Pyrrole Nucleus Via Trichloroacetylation and Alcoholysis", J. Org. Chem. 37(23):3618-3622 (1972).
Booth C. et al., "Preparation and Reactivity of β-(Tri-N-Butylstannyl)Acrylates", Tetrahedron Letters 33(3):413-416 (1992).
Stevens C.V. et al., "A Cooper-Catalyzed Domino Radical Cyclization Route to Benzospiro-Indolizidinepyrrolidinones", Tetrahedron Letters 48:7108-7111 (2007).
Dumas D.J. et al., "Total Synthesis of Peramine", J. Org. Chem. 53:4650-4653 (1988).
Crowley et al., "Cyclization Via Solid Phase Synthesis. Unidirectional Dieckmann Products from Solid Phase and Benzyl Triethylcarbinyl Pimelates", Journal of the American Chemical Society 92(21):6363-6365 (Oct. 21, 1970).
Borch R.F. et al., "The Cyanohydridoborate Anion as a Selective Reducing Agent", Journal of the American Chemical Society 93(12):2897-2904 (Jun. 16, 1971).
Youngman M.A. et al., "Mannich Reactions of a Resin-Bound Terminal Alkyne", Tetrahedron Letters 38(36):6347-6350 (1997).
Palmer B.D. et al., "Structure-Activity Relationships for 5-Substituted 1-Phenylbenzimidazoles as Selective Inhibitors of the Platelet-Derived Growth Factor Receptor", J. Med. Chem. 42:2373-2382 (1999).
Lackey K. et al., "The Discovery of Potent cRaf1 Kinase Inhibitors", Bioorganic & Medicinal Chemistry Letters 10:223-226 (2000).
Koresawa M. et al., "High-Throughput Screening with Quantitation of ATP Consumption: A Universal Non-Radioisotope, Homogeneous Assay for Protein Kinase", ASSAY and Drug Development Technologies 2(2):153-160 (2004).

*Primary Examiner* — Brenda Coleman

(74) *Attorney, Agent, or Firm* — Scully, Scott, Murphy & Presser, P.C.

(57) ABSTRACT

Compounds which are tricyclopyrazole derivatives or pharmaceutically acceptable salts thereof, their preparation process and pharmaceutical compositions comprising them are disclosed; these compounds are useful in the treatment of diseases caused by and/or associated with an altered protein kinase activity such as cancer, viral infection, prevention of AIDS development in HIV-infected individuals, cell proliferative disorders, autoimmune and neurodegenerative disorders; also disclosed is a process under Solid Phase Synthesis conditions for preparing the compounds of the invention and chemical libraries comprising a plurality of them.

15 Claims, No Drawings

TRICYCLOPYRAZOLE DERIVATIVES

This application is a national stage application filed under 35 U.S.C. 371 of PCT/EP2010/068129, filed Nov. 24, 2010. The present invention relates to certain substituted derivatives of tricyclopyrazole compounds, which modulate the activity of protein kinases. The compounds of this invention are therefore useful in treating diseases caused by dysregulated protein kinase activity. The present invention also relates to methods for preparing these compounds, combinatorial libraries thereof, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For general reference to PKs malfunctioning or disregulation see, for instance, Current Opinion in Chemical Biology 1999, 3, 459-465 and Carcinogenesis 2008, 29, 1087-191.

Substituted hexahydroarylquinolizine derivatives useful as antidiabetics, antidepressants, antihypertensives, and inhibitors of blood platelet aggregation, are disclosed in EP154142 A in the name of Merck and Co.

Synthesis of 1H-imidazo[1,2-a]pyrazolo[3,4-c]pyridine derivatives are described in Chemical & Pharmaceutical Bulletin (1990), 38(9), 2352-6, without reporting any biological activity.

Tricyclic 5,6-dihydro-9H-pyrazolo[3,4-c]-1,2,4-triazolo[4,3-α]pyridine derivatives as phosphodiesterase inhibitors useful for the treatment of an inflammatory condition, asthma, arthritis, bronchitis, chronic obstructive airways disease, psoriasis, allergic rhinitis, dermatitis as well as AIDS, septic shock and other diseases, such as cachexia, are disclosed in WO9639408 in the name of Pfizer Inc.

Pyrrolo[2,1-a]isoquinolines, pyrrolo[1,2-a]quinolines, pyrrolo[2,1-a]isobenzazepines, and pyrrolo[1,2-a]benzazepines derivatives endowed with antineoplastic activity are described in Journal of Medicinal Chemistry (1988), 31(11), 2097-102.

Pyrrolo[2,1-a]isoquinolines as phosphodiesterase 10a inhibitors useful for treating cancer, are disclosed in WO2002048144 in the name of Bayer Aktiengesellschaft.

The present inventors have now discovered that the new compounds of formula (I), described below, are kinase inhibitors and are thus useful in therapy as antitumor agents.

Accordingly, a first object of the present invention is to provide a tricyclic compound represented by formula (I):

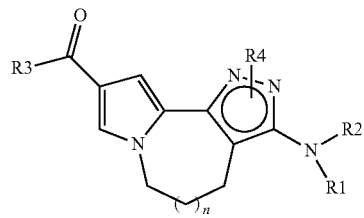

wherein n is 0 or 1;

R1, R2 and R4, each independently one from the other, are selected from the group consisting of —$R^a$, —$COR^a$, —$CONHR^a$, —$SO_2R^a$ and —$COOR^a$;

R3 is a group —$NR^aR^b$ or —$OR^a$;

wherein $R^a$ and $R^b$, the same or different, are each independently hydrogen or a group optionally substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl or, taken together with the nitrogen atom to which they are bonded, either $R^a$ and $R^b$, may form an optionally substituted 3 to 8 membered heterocycle, optionally containing one additional heteroatom or heteroatomic group selected from S, O, N or NH, and pharmaceutically acceptable salts thereof.

The present invention also provides methods of synthesizing the substituted compounds, represented by formula (I), prepared through a synthetic process comprising well known reactions carried out according to conventional techniques, as well as through an extremely versatile solid-phase and/or combinatorial process.

The present invention also provides a method for treating diseases caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPSI, MST4, NEK6, NIM1, P38alpha, PAK-4, PDGFR, PDK1, PERK, PIM1, PIM2, PKAalpha, PKCbeta, PLK1, RET, ROS1, SULU1, Syk, TLK2, TRKA, TYK, VEGFR2, VEGFR3, ZAP70.

A preferred method of the present invention is to treat a disease caused by and/or associated with dysregulated protein kinase activity selected from the group consisting of cancer, viral infection, prevention of AIDS development in HIV-infected individuals, cell proliferative disorders, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The compounds of this invention may be useful in inhibiting tumour angiogenesis and metastasis, as well as in the treatment of organ transplant rejection and host versus graft disease.

The present invention further provides a method of treatment comprising a compound of formula (I) in combination with radiation therapy or chemotherapy regimen for simultaneous, separate or sequential use in anticancer therapy.

Moreover the invention provides an in vitro method for inhibiting protein kinase activity which comprises contacting the said protein kinase with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, DNA damaging or intercalating agents, platin-based agents, alkylating agents, antimetabolite agents, hormonal agents, antihormonal agents such as antiestrogens, antiandrogens and aromatase inhibitors, immunological agents, interferon-type agents, cyclooxygenase inhibitors (e.g. COX-2 inhibitors), matrixmetalloprotease inhibitors, tyrosine kinase inhibitors, other kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, inhibitors of kinesins, therapeutic monoclonal antibodies, inhibitors of mTOR, histone deacetylase inhibitors, inhibitors of hypoxic response and the like, for simultaneous, separate or sequential use in anticancer therapy.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

As used herein, a compound of formula (I) wherein n is 0 and R1, R2, R3 and R4 are as defined above, namely 4,5-dihydro-1H-pyrazolo[4,3-g]indolizine derivatives, may be represented by the general formula (I)A:

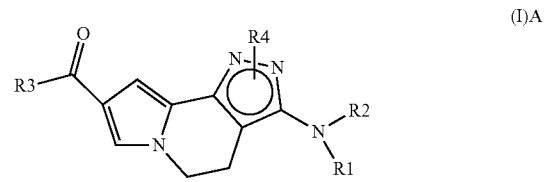

(I)A and a compound of formula (I) wherein n is 1 and R1, R2, R3 and R4 are as defined above, namely 1,4,5,6-tetrahydropyrazolo[3,4-c]pyrrolo[1,2-a]azepine derivatives, may be represented by the general formula (I)B:

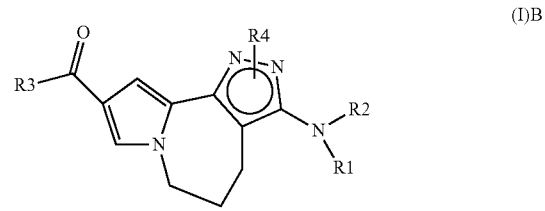

(I)B

Unless otherwise specified, when referring to the compounds of formula (I) per se as well as to any pharmaceutical composition thereof or to any therapeutic method of treatment comprising them, the present invention includes all the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release the active parent drug according to formula (I) in vivo.

N-oxides are compounds of formula (I) wherein nitrogen and oxygen are tethered through a dative bond.

All forms of chiral isomers or other forms of isomers including enantiomers and diastereomers, are intended to be covered herein. Compounds containing a chiral center may be used as a racemic mixture or as an enantiomerically enriched mixture, or the racemic mixture may be separated using well-known techniques and an individual enantiomer may be used alone.

In cases wherein compounds may exist in other tautomeric forms, such as keto-enol tautomers, each tautomeric form is contemplated as being included within this invention whether existing in equilibrium or predominantly in one form.

As such, unless otherwise provided, when in compounds of formula (I) n, R1, R2 and R3 are as defined above, R4 is hydrogen and only one of the following tautomeric forms of formula (I)a or (I)b is indicated, the remaining one has still to be intended as comprised within the scope of the invention:

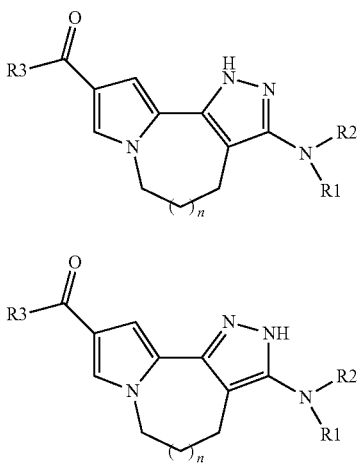

In the present description, unless otherwise indicated, with the term "straight or branched $C_1$-$C_6$ alkyl" we intend any group such as, for instance, methyl, ethyl, n-propyl, isopropyl, n-butyl, isobutyl, sec-butyl, tert-butyl, n-pentyl, n-hexyl, and the like.

With the term "straight or branched $C_2$-$C_6$ alkenyl" or "straight or branched $C_2$-$C_6$ alkynyl" we intend any of the unsaturated alkenyl or alkynyl groups with from 2 to 6 carbon atoms for instance including vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term "$C_3$-$C_6$ cycloalkyl" we intend, unless otherwise specified, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "aryl" we intend a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non-limiting examples of such aryl groups are phenyl, α- or β-naphthyl or biphenyl groups.

With the term "heteroaryl" we intend aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the meanings provided to $R^a$ and $R^b$, any of the above groups may be further optionally substituted in any of their free positions by one or more groups, for instance 1 to 6 groups, selected from: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, $C_3$-$C_6$ cycloalkyl, heterocyclyl, aryl, heteroaryl; amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

In the present description, unless otherwise specified, with the term "cyano" we intend a —CN residue.

With the term "nitro" we intend a —$NO_2$ group.

With the term "halogen" we intend a fluorine, chlorine, bromine or iodine atom.

With the term "polyfluorinated alkyl or alkoxy" we intend a straight or branched $C_1$-$C_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkyloxy, alkylcarbonyloxy and the like, has to be intended as conventionally construed from the parts to which it derives. So far, as an example, the terms heterocyclyl-alkyl and cycloalkyl-alkyl stand for a straight or branched alkyl group being further substituted by a heterocyclic or cycloalkyl group, respectively, as above defined.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A preferred class of compounds of formula (I) are the compounds wherein:

R1 is a group —CONHR$^a$ wherein R$^a$ is hydrogen or a group optionally substituted selected from straight or branched $C_1$-$C_6$ alkyl, straight or branched $C_2$-$C_6$ alkenyl, aryl and aryl $C_1$-$C_6$ alkyl.

Another preferred class of compounds of formula (I) are the compounds wherein:

R1 is a group —COR$^a$ wherein R$^a$ is hydrogen or a group optionally substituted selected from straight or branched $C_1$-$C_6$ alkyl, straight or branched $C_2$-$C_6$ alkenyl, aryl and aryl $C_1$-$C_6$ alkyl.

Another preferred class of compounds of formula (I) are the compounds wherein:

R1 is a group —SO$_2$R$^a$ wherein R$^a$ is hydrogen or a group optionally substituted selected from straight or branched $C_1$-$C_6$ alkyl, straight or branched $C_2$-$C_6$ alkenyl, aryl and aryl $C_1$-$C_6$ alkyl.

A further preferred class of compounds of formula (I) are the compounds wherein:

R2 is hydrogen.

A more preferred class of compounds of formula (I) are the compounds wherein:

R3 is a group —NR$^a$R$^b$ wherein both of R$^a$ and R$^b$ are hydrogen or one of them is a hydrogen and the remaining one of R$^a$ or R$^b$ is a group optionally substituted selected from straight or branched $C_1$-$C_6$ alkyl, straight or branched $C_2$-$C_6$ alkenyl, aryl and aryl $C_1$-$C_6$ alkyl.

The most preferred class of compounds of formula (I) are the compounds wherein:

R4 is an hydrogen.

For a reference to any specific compound of formula (I) of the invention, optionally in the form of pharmaceutically acceptable salts, see the experimental section.

The present invention also provides a process for the preparation of a compound of formula (I) as defined above, characterized in that the process comprises the following steps:

a) reaction of the compound of formula (II):

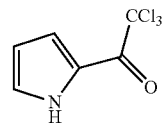

(II)

with an alcohol of formula (III)

R$^{a'}$—OH (III)

wherein R$^{a'}$ is straight or branched $C_1$-$C_6$ alkyl group;

b) acylation by Friedel-Craft reaction of the resultant compound of formula (IV):

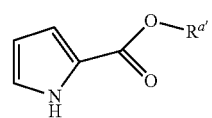

(IV)

wherein R$^{a'}$ is as defined above;

c) reaction of the resultant compound of formula (V):

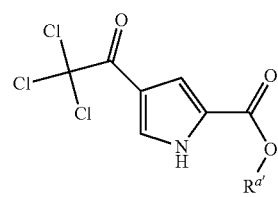

(V)

wherein R$^{a'}$ is as defined above, with a suitable alcohol of formula (III) as defined above;

d) alkylation of the resultant compound of formula (VI):

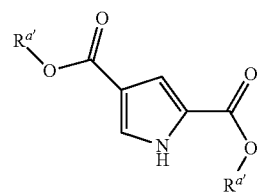

(VI)

wherein both R$^{a'}$ are independently as defined above, with suitable halo-cyanoalkane of formula (XXI):

(XXI)

wherein n is 0 or 1;

e) intramolecular condensation of the resultant compound of formula (VII):

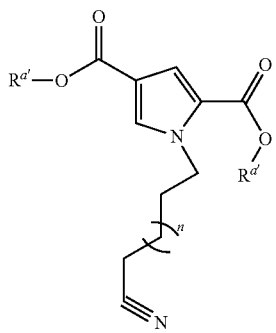

(VII)

wherein n is as defined above and both $R^{a'}$ are independently as defined above;

f) treatment with hydrazine or an hydrazine salt thereof, of the resultant compound of formula (VIII):

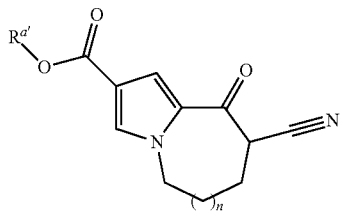

(VIII)

wherein n and $R^{a'}$ are as defined above, to give a compound of formula (I):

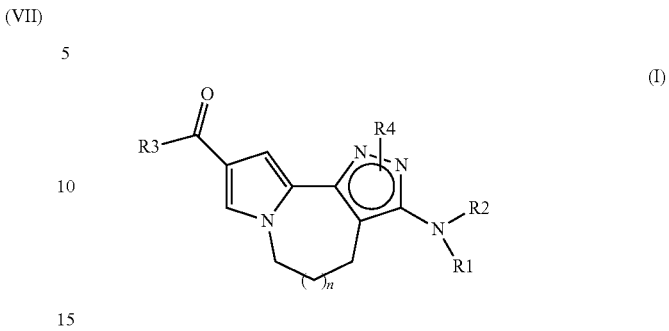

(I)

wherein n is 0 or 1; R1, R2 and R4 are hydrogen and R3 is —$OR^{a'}$, wherein $R^{a'}$ is a straight or branched $C_1$-$C_6$ alkyl group; optionally separating the resultant compound of formula (I) into the single isomers; and/or converting the resultant compound of formula (I) into a different compound of formula (I) by replacing the group —$OR^{a'}$ with a different group which R3 represents, and/or introducing the R4 group, and/or derivatizing the amino moiety; and/or removing the R4 group, and/or converting it into a pharmaceutically acceptable salt if desired.

Said optional conversions of a compound of formula (I) are summarized in scheme A below.

Scheme A

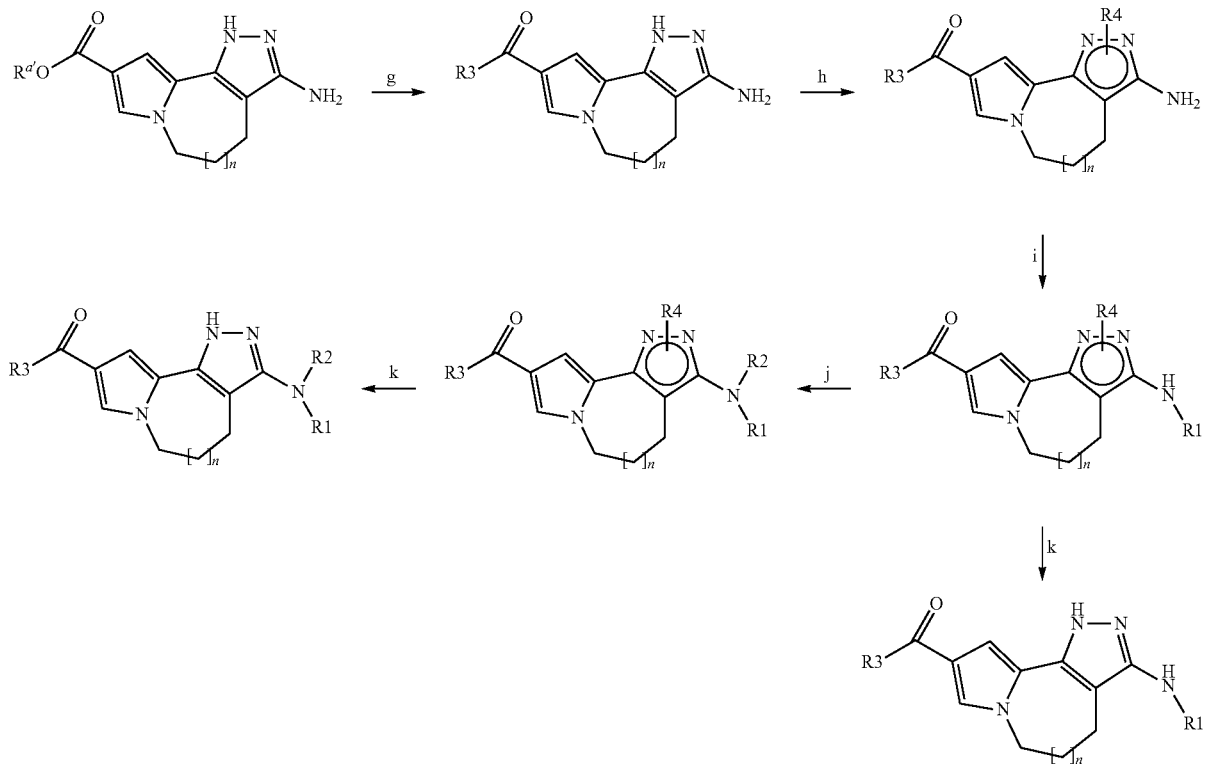

wherein n, R1, R2, R3 and R4 are as defined above and $R^a$ is straight or branched $C_1$-$C_6$ alkyl group.

The present invention further provides a process for the preparation of a compound of formula (I) as defined above, characterized in that the compound of formula (I) wherein n is as defined in formula (I);

R1, R2 and R4 are hydrogen, and $R^a$ is straight or branched $C_1$-$C_6$ alkyl group, is optionally converted into the corresponding compound of formula (I) by replacing the group —$OR^{a'}$ with a different group which R3 represents, said conversion is carried out in step g) by one or more of the following reactions:

g.1) hydrolysis under basic condition to give the corresponding compound of formula (I) wherein R3 is OH, optionally followed by the coupling of the resultant compound with an amine of formula (IX):

$HNR^aR^b$ (IX)

wherein $R^a$ and $R^b$ are as defined in claim 1, to give the corresponding compound of formula (I) wherein R3 is —$NR^aR^{b'}$ and $R^a$ and $R^b$ are as defined in claim 1;

g.2) transesterification by reactions with a compound of formula (III) as defined above, to give the corresponding compound of formula (I) wherein R3 is $OR^{a'}$ and $R^{a'}$ is a different $C_1$-$C_6$ alkyl;

g.3) coupling with an amine of formula (IX):

$HNR^aR^b$ (IX)

wherein $R^a$ and $R^b$ are as defined in formula (I), to give the corresponding compound of formula (I) wherein R3 is —$NR^aR^{b'}$ and $R^a$ and $R^b$ are as defined in formula (I).

The present invention further provides a process for the preparation of a compound of formula (I) as defined above, characterized in that the compound of formula (I) wherein n and R3 are as defined in formula (I), and R1, R2 and R4 are hydrogen, is optionally converted into the corresponding compound of formula (I) by introducing the group R4, said conversion is carried out in step h) by one or more of the following reactions:

h.1) coupling with an equivalent of an halide of formula (X):

$R^aZ$ (X)

wherein $R^a$ is as defined in formula (I) but not hydrogen and Z is a halogen, to give the corresponding compound of formula (I) wherein R4 is $R^a$, and $R^a$ is as defined in formula (I) but not hydrogen;

h.2) coupling with an equivalent of an acyl halide of formula (XI):

$R^aCOZ$ (XI)

wherein $R^a$ and Z are as defined above, to give the corresponding compound of formula (I) wherein R4 is —$COR^a$ and $R^a$ is as defined above;

h.3) coupling with an equivalent of an alcohoxycarbonyl halide of formula (XII):

$R^aOCOZ$ (XII)

wherein $R^a$ and Z are as defined above, to give the corresponding compound of formula (I) wherein R4 is —$OCOR^a$ and $R^a$ is as defined above;

h.4) coupling with an equivalent of a sulfonyl halide of formula (XIII):

$R^aSO_2Z$ (XIII)

wherein $R^a$ and Z are as defined above, to give the corresponding compound of formula (I) wherein R4 is —$SO_2R^a$ and $R^a$ is as defined above;

h.5) coupling with an equivalent of an isocyanate of formula (XIV):

$R^aNCO$ (XIV)

wherein $R^a$ is as defined above, to give the corresponding compound of formula (I) wherein R4 is —$CONHR^a$ and $R^a$ is as defined above.

The present invention further provides a process for the preparation of a compound of formula (I) as defined above, characterized in that the compound of formula (I) wherein n and R3 are as defined in formula (I); R1 and R2 are hydrogen and R4 is as defined in formula (I) but not hydrogen, is optionally converted into the corresponding compound of formula (I) by derivatizing the amino moiety, said conversion is carried out in step i) by one or more of the following reactions:

i.1) coupling with an equivalent of an acyl halide of formula (XI):

$R^aCOZ$ (XI)

wherein $R^a$ is as defined in formula (I) but not hydrogen and Z is a halogen, to give the corresponding compound of formula (I) wherein one of R1 or R2 is hydrogen and the other one is —$COR^a$ and $R^a$ is as defined above;

i.2) coupling with an equivalent of an alkoxycarbolyl halide of formula (XII):

$R^aOCOZ$ (XII)

wherein $R^a$ and Z are as defined above, to give the corresponding compound of formula (I) wherein one of R1 or R2 is hydrogen and the other one is —$OCOR^a$ and $R^a$ is as defined above;

i.3) coupling with an equivalent of a sulfonyl halide of formula (XIII):

$R^aSO_2Z$ (XIII)

wherein $R^a$ and Z are as defined above, to give the corresponding compound of formula (I) wherein one of R1 or R2 is hydrogen and the other one is —$SO_2R^a$ and $R^a$ is as defined above;

i.4) coupling with an equivalent of an isocyanate of formula (XIV):

$R^aNCO$ (XIV)

wherein $R^a$ is as defined above, to give the corresponding compound of formula (I) wherein one of R1 or R2 is hydrogen and the other one is —$CONHR^a$ and $R^a$ is as defined above;

i.5) coupling with an equivalent of a carbonyl compound of formula (XV):

$R^aCORb^a$ (XV)

wherein $R^a$ and $R^b$ are as defined in formula (I), to give the corresponding compound of formula (I) wherein one of R1 or R2 is hydrogen and the other one is —$COR^a$ and $R^a$ is as defined above.

The present invention further provides a process for the preparation of a compound of formula (I) as defined above, characterized in that the compound of formula (I) wherein n and R3 are as defined in formula (I); one of R1 and R2 is hydrogen and the other is as defined in formula (I) but not hydrogen, and R4 is as defined in formula (I) but not hydrogen, is optionally converted into the corresponding compound of formula (I) by further derivatizing the amino moiety, said conversion is carried out in step j) by one or more of the reaction described under steps i.1)-i.5) described above.

The present invention further provides a process for the preparation of a compound of formula (I) as defined above, characterized in that the compound of formula (I) wherein n, R1, R2 and R3 are as defined in formula (I) and R4 is as defined in formula (I) but not hydrogen, is optionally converted into the corresponding compound of formula (I) by removing the group R4 by treatment with a basic solution to give the corresponding compound of formula I wherein R4 is hydrogen, said conversion is carried out in step k).

The above process is an analogy process which can be carried out according to well-known methods.

The starting materials of the process object of the present invention, comprehensive of any possible variant, as well as any reactant thereof, are known compounds and if not commercially available per se may be prepared according to well-known methods.

For example, the compound of formula (II) and (XXI) are commercially available.

The compounds of formula (III), (IX), (X), (XI), (XII), (XIII), (XIV), (XV) and (XXI) are either commercially available or known and easily obtained according to known methods, for a general reference see: Smith, Michael—March's Advanced Organic Chemistry: reactions mechanisms and structure—$5^{th}$ Edition, Michael B. Smith and Jerry March, John Wiley & Sons Inc., New York (N.Y.), 2001.

According to step a) of the process the 2,2,2-trichloro-1-(1H-pyrrol-2-yl)ethanone is reacted with ethanol to obtain the ethyl 1H-pyrrole-2-carboxylate. This reaction can be conducted in a variety of ways and experimental conditions, which are widely known in the art for condensation reactions. For a general reference to the operative conditions see: Nishiwaki, E. et al, Heterocycles [HTCYAM] 1988, 27, 1945; Freedlander, R. S. et al, J Org Chem [JOCEAH] 1981, 46, 3519; Harbuck, J. W. et al, J Org Chem [JOCEAH] 1972, 37, 3618; and Booth, C et al, Tetrahedron Lett [TELEAY] 1992, 33 (3), 413. Preferably, the reaction is carried out in presence of a base like trialkyl amine, sodium or potassium carbonates, alkali hydroxide or alkali hydride. The solvent, in case is not the same ethanol, could be a suitable solvent such as THF, ACN, dioxane or mixture of them and the temperature raging from room temperature to reflux.

According to step b) of the process, the compound of formula (IV) is reacted with trichloroacetyl chloride in presence of strong lewis acid such as $AlCl_3$, $ZnCl_2$, Pyridine, $FeCl_3$ or $Sm(OTf)_3$ in a dry solvent as ether, DCM, THF. Preferably, the reaction is carried out at reflux temperature.

According to step c) of the process, the compound of formula (V) is reacted with ethanol and the reaction is carried out as described under step (a).

According to step d) of the process, the reaction of the compound of formula (VI) with the halo-cyanoalkane can be conducted in a variety of ways and experimental conditions, which are widely known in the art for condensation reactions. For a general reference to the operative conditions see: Stevens, C. V. et al, Tetrahedron Lett [TELEAY] 2007, 48 (40), 7108-7111 and Dumas, D. J., J Org Chem [JOCEAH] 1988, 53, 4650. Preferably, the reaction is carried out in presence of bases such as alkali carbonates, alkali hydride in a suitable solvent such as tetahydrofuran, dichloromethane, acetonitrile, 1,4-dioxane or dimethylamide.

According to step e) of the process, the intramolecular condensation of the compound of formula (VII) can be conducted in a variety of ways and experimental conditions, which are widely known in the art. For a general reference see: Crowley, J. I. et al, J Am Chem Soc [JACSAT] 1970, 92, 6363-6365. Preferably the reaction is carried out according to the conditions of the Dieckmann reaction with potassium or sodium alkoxide in acetonitrile, tetrahydrofuran, toluene or an alcoholic solvent.

According to step f) of the process, the reaction between the compound of formula (VIII) and hydrazine or an hydrazine salt, can carried out in a variety of ways and experimental conditions, which are widely known in the art. Preferably, the reaction is carried out in the presence of catalytic amounts of an acid, for instance hydrochloric, acetic or sulphuric acid; in a suitable solvent such as, for instance, tetrahydrofuran, 1,4-dioxane, acetonitrile, methanol or ethanol; at a temperature ranging from about room temperature to reflux and for a time varying from about 30 minutes to about 8 hours.

According to any one of steps g.1) to g.3) of the process, the conversion of the alkoxycarbonyl derivative of formula (I) obtained in step e) into a different compound of formula (I) by replacing the group —$OR^{a'}$ with a different group which R3 represents, can be carried out in a variety of ways, according to conventional methods.

According to step g.1) of the process, the hydrolysis under acid or basic condition of the alkoxycarbonyl derivative for conversion into the corresponding carboxylic acid derivative, is conducted according to standard procedures as reported in The Chemistry of Carboxylic Acids and Esters, Saul Patai, Interscience Publisher (John Wiley&Sons 1969).

According to step g.2) of the process, the transesterification of the alkoxycarbonyl derivative is conducted according to standard procedures as reported in The Chemistry of Carboxylic Acids and Esters, Saul Patai, Interscience Publisher (John Wiley&Sons 1969).

According to step g.3) of the process, the coupling of the alkoxycarbonyl or the corresponding carboxylic acid derivative with an amine is conducted according to standard procedures as reported in The Chemistry of Amides, Saul Patai, Interscience Publisher (John Wiley&Sons 1970). Preferably, the reaction is carried out in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (HBTOH), O-benzotriazolyltetramethylisouronium tetrafluoroborate (TBTU), or benzotriazol-1-yloxytripyrrolidinophosphonium hexafluorophosphate (PyBOP), in an appropriate solvent such as dichloromethane or dimethylformamide, under the setting well-known to skilled person.

According to any one of steps h.1) to h.5) of the process, the introduction of the group R4 can be carried out in a variety of ways, according to conventional methods.

The selective introduction of the R4 group on the pyrazole nitrogen in position 1 or 2, due to the tautomeric equilibrium, could be obtained working with a stoichiometric amount of the alkylating, acylating, carbonylating, sulphorilating agent or isocyanate of formula (X), (XI), (XII), (XIII), (XIV) respectively, so as to prevent the multi-derivatization even on the amino group in position 3. The reaction is conducted in a suitable solvent such as dichloromethane, dimethylformamide, tetrahydrofuran or dioxane without using a base that could cleave in situ the R4 substituent just inserted.

According to any one of steps i.1) to i.5) of the process, the derivatization of the amino moiety, can be carried out in a variety of ways, according to conventional methods. For reference see: The Chemistry of Amino Group, Saul Patai, Interscience Publisher (John Wiley&Sons 1968), or J. Am. Chem. or J. Am. Chem. Soc., 1971, 93, 2897, or Comprehensive Organic Synthesis, Trost B. N., Fleming L. (Eds. Pergamon Press: New York, 1991; Vol. 8).

Preferably, according to any one of steps i.1) to i.4) of the process, the compound of formula (I) is dissolved in a suitable solvent such as dichloromethane, dimethylformamide, tetrahydrofuran, 1,4-dioxane or the like, and a suitable base such as pyridine, triethyliamine, diisopropylamine or sodium carbonate is added therein. The compound of formula (XI), (XII), (XIII) respectively, is then added and the mixture stirred for a time of about 2 hours to about 15 hours, at a temperature ranging from about 20° C. to about 80° C. In the case of isocyanate of formula (XIV) the use of the base is optional.

Preferably, according to step i.5) of the process, the compound of formula (I) is reacted with an aldehyde or ketone derivative of formula (XV) under reductive conditions. From the above, it is clear to the skilled man that by employing an aldehyde derivative of formula (XV) wherein one of $R^a$ and $R^b$ is hydrogen, the corresponding derivative wherein R1 is —$CH_2R^a$ is obtained. Likewise, by employing a ketone derivative, the corresponding derivative wherein R1 is —$CHR^aR^b$, wherein $R^a$ and $R^b$ are as defined above but different from hydrogen, is obtained.

According to any one of steps j.1) to j.5) of the process, the further derivatization of the amino moiety, can be carried out in a variety of ways, according to conventional methods. It is clear to the person skilled in the art that the further derivatization of the amino moiety is carried out in the same conditions reported in the step i) described above, to obtain a bis-substitution on the nitrogen in position 3.

According to step k) of the process, the removal of the group $R^4$, can be carried out in a variety of ways, according to conventional methods. Preferably, the removal can be carried out reacting the compound of formula (I) with a basic solution such as hydrazine, ammonia, metal hydroxide and so on. With strongest base condition also the imides eventually present in position 3 can be hydrolyzed.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

In addition to the above, the compounds of formula (I) may be advantageously prepared according to combinatorial chemistry techniques widely known in the art, by accomplishing the aforementioned reactions between the intermediates in a serial manner and by working under solid-phase-synthesis (SPS) conditions.

The present invention also provides a process for the preparation of a compound of formula (I) as defined above, characterized in that the process comprises the following steps:

l) acylation of the alkoxycarbonyl derivative of formula (I) obtained in step f) described above, with trifluoroacetic anhydride;
m) removal from the resultant compound of the trifluoroacetyl group in position 1 or 2 of the pyrazolo ring;
n) loading of the resultant compound of formula (I) trifluoroacetylated in position 3 onto a resin as suitable solid support, wherein the resin is a commercially available polystyrenic resin such as for instance, Br-Wang resin, Trityl resin, Cl-trityl resin, Merriefield resin, MAMP resin or isocianate resin and derivatives thereof;
o) hydrolyzing under acid or basic conditions the alkoxycarbonyl group and the trifluoroacetyl group of the resultant compound of formula (XVI);
p) coupling the carboxyl group of the resultant compound of formula (XVII) with an amine of formula (IX) described above;
q) derivatizing the amino moiety in position 3 of resultant compound of formula (XVIII);
r) cleaving the resin from the resultant compound of formula (XIX), so as to obtain the desired compounds of formula I, optionally converting the resultant compound of formula (I) into a different compound of formula (I) and/or converting it into a pharmaceutically acceptable salt if desired.

Said solid-phase-synthesis (SPS) is summarized in scheme B below.

Scheme B

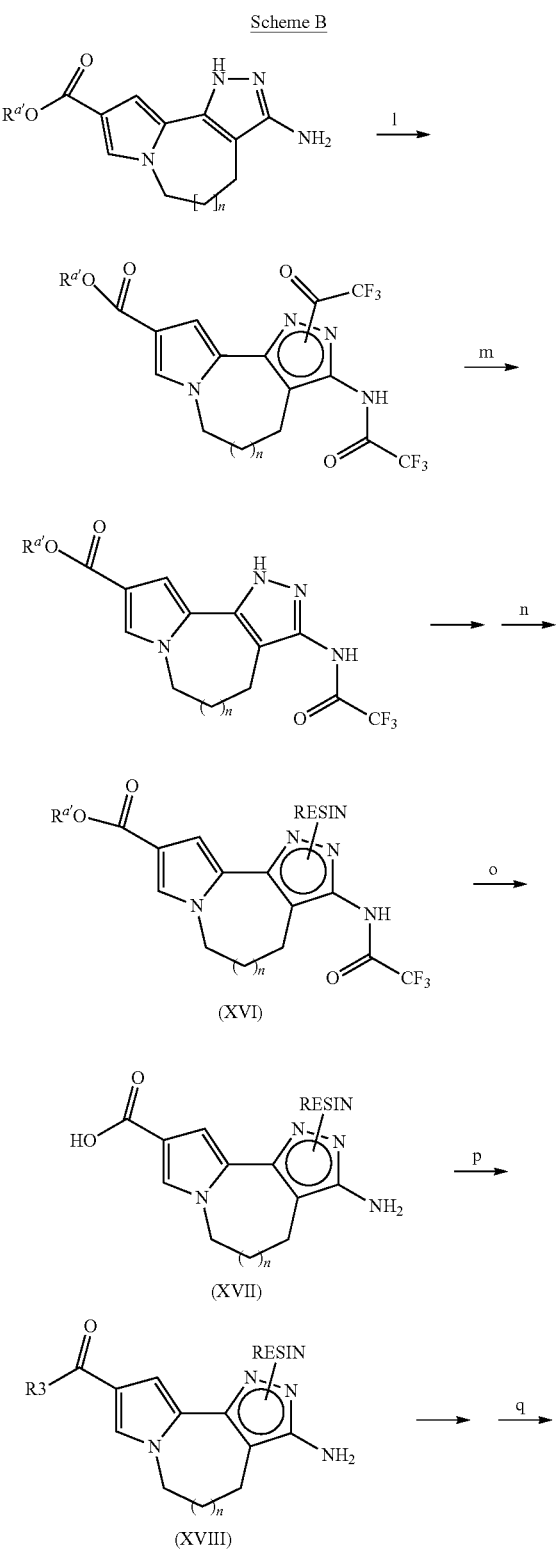

-continued

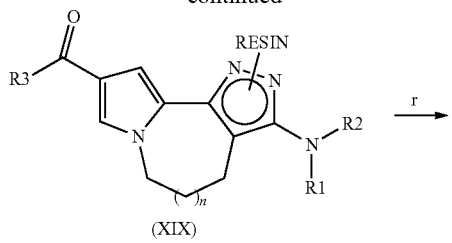

(XIX)

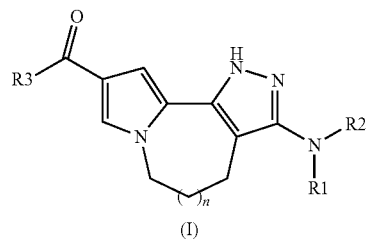

(I)

wherein the resin is a commercially available polystyrenic resin such as for instance, Br-Wang resin, Trityl resin, Cl-trityl resin, Merriefield resin, MAMP resin or isocianate resin and derivatives thereof; n, R1, R2 and R3 are as defined in formula (I) and $R^{a'}$ is straight or branched $C_1$-$C_6$ alkyl group.

Any of the above reactions is carried out according to known methods, by working as formerly reported, and allows obtaining compounds of formula (I) as set forth above.

Step l) is carried out as described under step i.1).

Step m) is carried out as described under step k).

According to step n) the compound of formula (I) is loaded on the trityl chloride resin (copolystyrene-1% DVB) to obtain the compound of formula XVI. The loading reaction may be carried out in a suitable solvent such as dichloromethane or tetrahydrofuran and in the presence of a base such as trethylamine, pyridine, diisopropylamine and so on. The reaction is shacked in a time between 18 and 24 h at room temperature. For references see: M. A. Youngman, et al. Tetrahedron Lett., 1997, 38, 6347; K. Barlos, et al. Poster P316, 24th European Peptide Symposium, Edinburgh, 1996.

Step o) is carried out as described under step g.1).

Step p) is carried out as described under step g.3).

Step q) is carried out as described under step i) and j).

According to step (r), the cleavage of the resin is performed under acidic conditions in the presence of suitable acids such as, for instance, hydrochloric, trifluoroacetic, methanesulfonic or p-toluensulfonic acid. Preferably the reaction is carried out using trifluoroacetic acid in dichloromethane as solvent.

Clearly, by working according to combinatorial chemistry techniques as formerly indicated, a plurality of compounds of formula (I) may be obtained.

Hence, it is a further object of the present invention a library of two or more compounds of formula (I), according to a preferred embodiment of the invention,

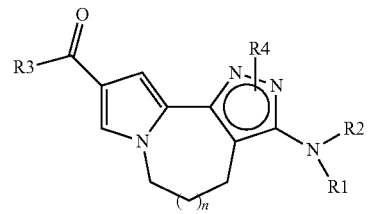

(I)

wherein
n is 0 or 1;
R1, R2 and R4, each independently one from the other, are selected from the group consisting of —$R^a$, —$COR^a$, —$CONHR^a$, —$SO_2R^a$ and —$COOR^a$;
R3 is a group —$NR^aR^b$ or —$OR^a$;
wherein $R^a$ and $R^b$, the same or different, are each independently hydrogen or a group optionally substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl or, taken together with the nitrogen atom to which they are bonded, either $R^a$ and $R^b$, may form an optionally substituted 3 to 8 membered heterocycle, optionally containing one additional heteroatom or heteroatomic group selected from S, O, N or NH,
and pharmaceutically acceptable salts thereof.

For a general reference to the above libraries of compounds of formula (I) see the experimental section.

From all of the above, it is clear to the skilled person that once a library of such derivatives is thus prepared, for instance consisting of about a thousands of compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

PHARMACOLOGY

The inhibiting activity of putative kinase inhibitors and the potency of selected compounds is determined through a method of assay based on the use of the Kinase-Glo® Luminescent Kinase Assay (commercially available from Promega corporation and described in Koresawa, M. and Okabe, T. (2004) High-throughput screening with quantitation of ATP consumption: A universal non-radioisotope, homogeneous assay for protein kinase. *Assay Drug Dev. Technol.* 2, 153-60).

The depletion of ATP as a result of kinase activity can be monitored in a highly sensitive manner through the use of Kinase-Glo® or Kinase-Glo® Plus Reagent, which uses luciferin, oxygen and ATP as substrates in a reaction that produces oxyluciferin and light.

The short forms and abbreviations used herein have the following meaning:
ACN acetonitrile
BSA bovine serum albumine
Tris 2-Amino-2-(hydroxymethyl)-1,3-propanediol
Hepes N-(2-Hydroxyethyl)piperazine-N'-(2-ethanesulfonic acid)
DTT threo-1,4-Dimercapto-2,3-butanediol
THF tetrahydrofuran TertBuOK potassium tertbuthoxy
MTBE methyl tertiary butyl ether
DIPEA diisopropylethylamine
PyBOP benzotriazol-1-yloxytris(pyrrolidino)phosphonium exafluorophosphate
EDC 1-ethyl-3-(3'-dimethylaminopropyl)carbodiimide
DHBTOH 3,4-dihydro-3-hydroxy-4-oxo-1,2,3-benzotriazine
TEA triethylamine
TFA trifluoroacetic acid
TFAA trifluoroacetic anhydride
TMOF trimethyl orto formate
DCE dichloroethane
DCM dichloromethane
DMF dimethylformammide
DMSO dimethylsulfoxide
HOBT hydroxybenzotriazole
KDa kiloDalton
mg milligram
μg microgram
ng nanogram
L liter
mL milliliter
μL microliter
M molar
mM millimolar
μM micromolar
nM nanomolar Kinase reaction conditions are target (enzyme) dependent and thus undergo individual adaptations. The Kinase-Glo® Luminescent Kinase Assay can be used with virtually any kinase and substrate combination.

Also the buffer conditions may vary depending on the kinase of interest (e.g for PKA a composition of 40 mM Tris pH 7.5, 20 mM $MgCl_2$, 0.1 mg/ml BSA, in 50 μl final volume is used). Typically the range of ATP titration is 0.1 μM to 10 μM.

The optimal kinase substrate results in the greatest change in luminescence when comparing kinase reaction wells with no kinase wells.

The optimal amount of kinase is determined by making two fold serial dilutions across plates using the optimal amount of ATP and optimal kinase substrate. The optimal amount of kinase to use in subsequent compound screens and 1050 determinations is the amount required for luminescence to be within the linear range of the kinase titration curve (sigmoidal dose response).

Robotized Kinase-Glo® Assay

This assay was set up for the measurement of kinase activity and/or inhibition.

It is homogeneous, quick, radioactivity-free and suitable for all type of protein kinases, such as PLK family, ABL, ACK1, AKT1, ALK, AUR1, AUR2, BRK, CDC7/DBF4, CDK2/CYCA, CHK1, CK2, EE2FK, EGFR1, ERK2, FAK, FGFR1, FLT3, GSK3beta, IGFR1, IKK2, IR, JAK2, JAK3, KIT, LCK, LYN, MAPKAPK2, MELK, MET, MPS1, MST4, NEK6, NIM1, P38alpha, PAK-4, PDGFR, PDK1, PERK, PIM1, PIM2, PIM3, PKAalpha, PKCbeta, PLK1, RET, SULU1, SYK, TRKA, VEGFR2, VEGFR3 or ZAP70.

We established the assay in 384 well-plates: the test mix consisted of:
1) 3× Enzyme mix (done in Kinase Buffer 3×), 5 μl/well
2) 3× substrate and ATP mix (done in $ddH_2O$), 5 μl/well
3) 3× compound of formula (I) (diluted into ddH2O-3% DMSO)-5 μl/well As an outcome, the percentage of inhibition at 10 μM was evaluated for each compound tested: see below for compound dilution and assay scheme. Each enzyme had its own buffer constitution, substrate type and concentration. Incubation time instead was 90 min for all targets.

Test compounds were received as a 1 mM solution in 100% DMSO into 96 well plates. The plates were diluted to 30 μM in $ddH_2O$, 3% DMSO; 4 plates are reorganized in 384 well plate by dispensing 5 μl of each 96 wp into the four quadrants of a 384wp. In well P23 and P24 the internal standard inhibitor staurosporine was added.

Assay Scheme

Test plates were first added with 5 μl of the compound dilution (30 μM, corresponding to 3× dilution) and then loaded onto a robotized station together with one reservoir for the Enzyme mix (3×) and one for the ATP mix (3×), specific for each target under study.

To start the assay, the robot aspirated 5 μl of ATP/Substrate mix, made an air gap inside the tips (5 μl) and aspirated 5 μl of Enzyme mix. The subsequent dispensation into the test plates allowed the kinase reaction to start after 3 cycles of mixing, done by the robot itself by up and down pipetting. At this point, the correct concentration was restored for all reagents.

The robot incubated the plates for 90 minutes at room temperature, and then stopped the reaction by pipetting 15 μl of Kinase-Glo® reagent into the reaction mix. Three cycles of mixing were done immediately after the addition of the reagent.

The principle of the Kinase-Glo® technique is the presence in the reagent mixture of oxygen, luciferin and luciferase enzyme: in the presence of ATP, remaining from the kinase reaction, oxi-luciferin is produced with the emission of light, directly dependent on the amount of ATP. For optimal performances of this technique, the kinase reaction should utilize at least 15-20% of the available ATP.

After another 60 minutes of incubation to stabilize the luminescent signal, the plates were read on a ViewLux® instrument. Data were analyzed using the software package Assay Explorer® that provided percent inhibition data.

As example herein are reported the assay conditions used for testing the compounds of formula (I) against ALKtide YFF APCo kinase;
ATP concentration: 1 μM
Enzyme concentration: 100 nM
Reaction buffer: Hepes 50 mM pH 7.5, $MgCl_2$ 5 mM, $MnCl_2$ 1 mM, DTT 1 mM, $Na_3VO_4$ 3 uM, 0.2 mg/ml BSA.
Assay procedure: add 5 ul compound of formula (I) (3×), add 5 μl ATP/S mix (3×) in buffer 1×; add 5 μl enzyme in buffer 2×+3×BSA; for the blank, add 5 μl buffer 2×+3×BSA without enzyme. After 90 minutes of incubation, add 15 μl/well of Kinase-Glo reagent. After 60-90 minutes of incubation to stabilize the luminescent signal, the plates are read on a ViuwLux instrument.

The inhibitory activity of putative kinase inhibitors and the potency of selected compounds were also determined using a trans-phosphorylation assay.

Specific peptide or protein substrates are trans-phosphorylated by their specific ser-thr or tyr kinase in the presence of ATP traced with $^{33}P$-γ-ATP, and in the presence of their own optimal buffer and cofactors. At the end of the phosphorylation reaction, more than 98% unlabeled ATP and radioactive ATP is captured by an excess of the ion exchange dowex resin; the resin then settles down to the bottom of the reaction plate by gravity. Supernatant is subsequently withdrawn and transferred into a counting plate, then evaluated by β-counting.

Reaction conditions are target (enzyme) dependent and thus undergo individual adaptations. Also the buffer conditions may vary depending on the kinase of interest. The assay can be used with virtually any kinase and substrate combination and is suitable for all type of protein kinases, such as ABL, ACK1, AKT1, ALK, AUR1, AUR2, BRK, BUB1, CDC7/DBF4, CDK21CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPSI, MST4, NEK6, NIM1, P38alpha, PAK-4, PDGFR, PDK1, PERK, PIM1, PIM2, PKAalpha, PKCbeta, PLK1, RET, ROS1, SULU1, Syk, TLK2, TRKA, TYK, VEGFR2, VEGFR3, ZAP70.

As example herein are reported the assay conditions used for testing the compounds of formula (I) against cdc7 and cdk2 kinase.

Inhibition Assay of Cdc7 Activity

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate.

The resulting $^{33}$P-labeled product is separated from unreacted tracer, transferred into a scintillation cocktail and light emitted is measured in a scintillation counter.

The inhibition assay of Cdc7/Dbf4 activity is performed according to the following protocol.

The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}$P phosphorylated MCM2 substrate remains in solution. The supernatant is collected, transferred into Optiplate plates and the extent of substrate phosphorylation is evaluated by β counting.

The inhibition assay of Cdc7/Dbf4 activity was performed in 96 wells plate according to the following protocol.

To each well of the plate were added:
  10 μl test compound (10 increasing concentrations in the nM to uM range to generate a dose-response curve). The solvent for test compounds contained 3% DMSO. (final concentration 1%)
  10 μl substrate MCM2 (6 M final concentration), a mixture of cold ATP (2 M final concentration) and radioactive ATP (1/5000 molar ratio with cold ATP).
  10 μl enzyme (Cdc7/Dbf4, 2 nM final concentration) that started the reaction. The buffer of the reaction consisted in 50 mM HEPES pH 7.9 containing 15 mM MgCl$_2$, 2 mM DTT, 3 uM NaVO$_3$, 2 mM glycerophosphate and 0.2 mg/ml BSA.

After incubation for 60 minutes at room temperature, the reaction was stopped by adding to each well 150 l of Dowex resin in the presence of 150 mM formic acid. After another 60 min incubation, 50 L of suspension were withdrawn and transferred into 96-well OPTI-PLATEs containing 150 l of MicroScint 40 (Packard); after 5-10 minutes shaking the plates were read for 1 min in a Packard TOP-Count radioactivity reader.

IC50 determination: inhibitors were tested at different concentrations ranging from 0.0005 to 10 M. Experimental data were analyzed by the computer program Assay Explorer using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Inhibition Assay of Cdk2/Cyclin A Activity

Kinase reaction: 1.5 μM histone H1 substrate, 25 μATP (0.2 μCi P33-ATP), 30 ng of baculovirus co-expressed Cdk2/Cyclin A, 10 M inhibitor in a final volume of 100 l buffer (TRIS HCl 10 mM pH 7.5, MgCl$_2$ 10 mM, 7.5 mM DTT) were added to each well of a 96 U bottom well plate. After 10 min at 37° C. incubation, reaction was stopped by 20 l EDTA 120 mM.

Capture: 100 μl were transferred from each well to MultiScreen plate, to allow substrate binding to phosphocellulose filter. Plates were then washed 3 times with 150 l/well PBS Ca++/Mg++free and filtered by MultiScreen filtration system.

Detection: filters were allowed to dry at 37° C., then 100 l/well scintillant were added and 33P labeled histone H1 was detected by radioactivity counting in the Top-Count instrument.

Results: Data are analysed by an internally customized version of the SW package "Assay Explorer" that provides either % inhibition for primary assays or sigmoidal fittings of the ten-dilutions curves for IC$_{50}$ determination in the secondary assays/hit confirmation routines.

As an example, in Table A are reported some compounds of the present invention which showed IC$_{50}$ of less 10 μM when tested against different kinases.

TABLE A

| Entry | Code | IC$_{50}$ (uM) | Enzyme |
|---|---|---|---|
| 190 | A20-M1-B8 | 2.43 | ABL |
| 193 | A21-M1-B8 | 4.94 | ABL |
| 200 | A35-M1-B8 | 3.50 | ABL |
| 10 | A5-M1-B8 | 2.23 | ABL |
| 390 | A21-M1-B34 | 5.34 | ABL |
| 397 | A35-M1-B34 | 4.31 | ABL |
| 400 | A5-M1-B34 | 0.82 | ABL |
| 434 | A21-M1-B36 | 3.23 | ABL |
| 467 | A5-M1-B37 | 5.10 | ABL |
| 561 | A5-M1-B41 | 0.40 | ABL |
| 578 | A5-M1-B42 | 1.79 | ABL |
| 615 | A5-M1-B43 | 0.54 | ABL |
| 10 | A5-M1-B8 | 1.86 | ABL |
| 619 | A38-M1-B41 | 2.29 | ABL |
| 619 | A38-M1-B41 | 0.92 | ABL |
| 100 | A5-M1-B25 | 1.92 | ACK1 |
| 120 | A5-M1-B26 | 3.04 | ACK1 |
| 141 | A5-M1-B27 | 2.40 | ACK1 |
| 163 | A5-M1-B28 | 4.33 | ACK1 |
| 190 | A20-M1-B8 | 1.04 | ACK1 |
| 193 | A21-M1-B8 | 0.63 | ACK1 |
| 196 | A6-M1-B8 | 1.89 | ACK1 |
| 200 | A35-M1-B8 | 0.49 | ACK1 |
| 10 | A5-M1-B8 | 0.63 | ACK1 |
| 221 | A35-M1-B10 | 3.13 | ACK1 |
| 224 | A5-M1-B10 | 3.25 | ACK1 |
| 238 | A21-M1-B17 | 1.41 | ACK1 |
| 246 | A5-M1-B17 | 2.16 | ACK1 |
| 263 | A35-M1-B30 | 6.56 | ACK1 |
| 266 | A5-M1-B30 | 4.71 | ACK1 |
| 307 | A35-M1-B7 | 5.91 | ACK1 |
| 310 | A5-M1-B7 | 1.43 | ACK1 |
| 331 | A5-M1-B31 | 3.16 | ACK1 |
| 342 | A20-M1-B32 | 3.06 | ACK1 |
| 351 | A35-M1-B32 | 1.21 | ACK1 |
| 354 | A5-M1-B32 | 1.38 | ACK1 |
| 390 | A21-M1-B34 | 0.89 | ACK1 |
| 397 | A35-M1-B34 | 1.08 | ACK1 |
| 400 | A5-M1-B34 | 0.36 | ACK1 |
| 434 | A21-M1-B36 | 3.34 | ACK1 |
| 443 | A5-M1-B36 | 4.12 | ACK1 |
| 467 | A5-M1-B37 | 1.00 | ACK1 |

TABLE A-continued

| Entry | Code | IC$_{50}$ (uM) | Enzyme |
|---|---|---|---|
| 480 | A21-M1-B38 | 2.04 | ACK1 |
| 489 | A5-M1-B38 | 2.16 | ACK1 |
| 509 | A35-M1-B39 | 2.85 | ACK1 |
| 512 | A5-M1-B39 | 1.94 | ACK1 |
| 536 | A5-M1-B40 | 1.73 | ACK1 |
| 552 | A21-M1-B41 | 2.45 | ACK1 |
| 559 | A35-M1-B41 | 2.87 | ACK1 |
| 561 | A5-M1-B41 | 0.96 | ACK1 |
| 576 | A35-M1-B42 | 2.20 | ACK1 |
| 578 | A5-M1-B42 | 0.44 | ACK1 |
| 615 | A5-M1-B43 | 1.01 | ACK1 |
| 680 | A5-M2-B26 | 4.84 | ACK1 |
| 855 | A5-M2-B31 | 3.51 | ACK1 |
| 894 | A35-M2-B33 | 3.82 | ACK1 |
| 897 | A5-M2-B33 | 2.47 | ACK1 |
| 918 | A33-M2-B34 | 1.44 | ACK1 |
| 957 | A35-M2-B36 | 3.98 | ACK1 |
| 959 | A5-M2-B36 | 0.74 | ACK1 |
| 1020 | A35-M2-B39 | 1.41 | ACK1 |
| 1023 | A5-M2-B39 | 0.55 | ACK1 |
| 1024 | A27-M2-B39 | 3.17 | ACK1 |
| 1051 | A21-M2-B41 | 1.56 | ACK1 |
| 1055 | A5-M2-B41 | 0.44 | ACK1 |
| 10 | A5-M1-B8 | 0.48 | ACK1 |
| 619 | A38-M1-B41 | 2.48 | ACK1 |
| 1100 | A38-M2-B41 | 2.82 | ACK1 |
| 1055 | A5-M2-B41 | 0.24 | ACK1 |
| 619 | A38-M1-B41 | 1.00 | ACK1 |
| 200 | A35-M1-B8 | 0.30 | ACK1 |
| 397 | A35-M1-B34 | 1.58 | ACK1 |
| 620 | A39-M1-B8 | 0.75 | ACK1 |
| 621 | A39-M1-B34 | 5.54 | ACK1 |
| 397 | A35-M1-B34 | 4.91 | ALK |
| 400 | A5-M1-B34 | 5.81 | ALK |
| 615 | A5-M1-B43 | 3.40 | ALK |
| 390 | A21-M1-B34 | 5.06 | BRK |
| 397 | A35-M1-B34 | 4.35 | BRK |
| 400 | A5-M1-B34 | 0.86 | BRK |
| 467 | A5-M1-B37 | 5.77 | BRK |
| 480 | A21-M1-B38 | 6.30 | BRK |
| 561 | A5-M1-B41 | 4.35 | BRK |
| 578 | A5-M1-B42 | 3.64 | BRK |
| 615 | A5-M1-B43 | 4.68 | BRK |
| 63 | A16-M1-B18 | 2.99 | CDC7/DBF4 |
| 63 | A16-M1-B18 | 1.90 | CDK2/CYCA |
| 615 | A5-M1-B43 | 7.87 | EGFR1 |
| 397 | A35-M1-B34 | 5.76 | FGFR1 |
| 615 | A5-M1-B43 | 7.27 | FGFR1 |
| 63 | A16-M1-B18 | 1.92 | GSK3beta |
| 190 | A20-M1-B8 | 2.02 | KIT |
| 200 | A35-M1-B8 | 3.52 | KIT |
| 400 | A5-M1-B34 | 4.13 | KIT |
| 434 | A21-M1-B36 | 5.03 | KIT |
| 561 | A5-M1-B41 | 1.83 | KIT |
| 578 | A5-M1-B42 | 6.61 | KIT |
| 615 | A5-M1-B43 | 1.31 | KIT |
| 54 | A8-M1-B16 | 2.68 | KIT |
| 26 | A9-M1-B13 | 5.85 | KIT |
| 56 | A9-M1-B16 | 0.85 | KIT |
| 58 | A11-M1-B16 | 2.66 | KIT |
| 10 | A5-M1-B8 | 5.98 | KIT |
| 63 | A16-M1-B18 | 2.61 | KIT |
| 64 | A16-M1-B19 | 4.47 | KIT |
| 397 | A35-M1-B34 | 3.50 | LCK |
| 400 | A5-M1-B34 | 3.99 | LCK |
| 434 | A21-M1-B36 | 5.14 | LCK |
| 561 | A5-M1-B41 | 1.15 | LCK |
| 615 | A5-M1-B43 | 0.59 | LCK |
| 619 | A38-M1-B41 | 4.13 | LCK |
| 200 | A35-M1-B8 | 2.13 | LYN |
| 709 | A32-M2-B28 | 3.09 | MELK |
| 752 | A30-M2-B8 | 2.57 | MELK |
| 918 | A33-M2-B34 | 1.23 | MELK |
| 976 | A24-M2-B37 | 3.00 | MELK |
| 63 | A16-M1-B18 | 6.33 | MELK |
| 397 | A35-M1-B34 | 4.17 | PKCbeta |
| 709 | A32-M2-B28 | 1.63 | Syk |
| 752 | A30-M2-B8 | 2.10 | Syk |
| 1151 | A42-M2-B33 | 3.15 | Syk |
| 918 | A33-M2-B34 | 0.48 | Syk |
| 976 | A24-M2-B37 | 2.78 | Syk |
| 397 | A35-M1-B34 | 3.98 | VEGFR3 |
| 400 | A5-M1-B34 | 4.94 | VEGFR3 |
| 665 | A1-M2-B25 | 1.56 | ZAP70 |
| 709 | A32-M2-B28 | 0.80 | ZAP70 |
| 752 | A30-M2-B8 | 0.59 | ZAP70 |
| 1151 | A42-M2-B33 | 1.83 | ZAP70 |
| 918 | A33-M2-B34 | 0.72 | ZAP70 |
| 976 | A24-M2-B37 | 1.15 | ZAP70 |

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

General Methods

Flash Chromatography was performed on silica gel (Merck grade 9395, 60A). The high-pressure liquid chromatography retention times (HPLC: r.t. values) were determined by:

HPLC Method 1A and 1B:

A Waters Alliance LC mod. 2795 equipped with a variable UV detector mod 2487, a Chemiluminescence Nitrogen detector (CLND, Antek 8060) and a Waters ZQ2000 mass detector (ESI interface) was used in this application. The total flow was splitted and distributed to the three detectors at a fixed ratio (64:15:21 UV:MS:CLND). The liquid chromatograph was equipped with a 30×3.0 mm I.D. column (Waters X-Bridge C18, 3.5 um particles), thermostated at 50° C. Two mobile phases were used: phase A was 0.05% w/v formic acid (1 mL/L of 50% formic acid Fluka 09676 in highly purified water) and phase B was 70/25/5 (v/v/v) MeOH/iPrOH/H$_2$O containing 0.035% w/v of formic acid (700 uL/L of 50% formic acid Fluka 09676).

A 5 μL volume of 1 mM nominal sample solution in DMSO was injected (sequential, partial loop mode with no air gaps) and a generic reversed phase gradient analysis was carried out at 0.8 mL/min into either a fast variant (method 1A) or a slower one (method 1B), as indicated in the following table:

| Method 1A | | Method 1B | |
|---|---|---|---|
| tR (min) | phase B (%) | tR (min) | phase B (%) |
| 0.00 | 0 | 0.00 | 0 |
| 5.00 | 100 | 8.00 | 100 |
| 5.70 | 100 | 9.00 | 100 |

-continued

| Method 1A | | Method 1B | |
|---|---|---|---|
| tR (min) | phase B (%) | tR (min) | phase B (%) |
| 5.71 | 0 | 9.01 | 0 |
| 6.3 | stop time | 9.6 | stop time |
| 7.9 | total analysis time (*) | 11.2 | total analysis time (*) |

(*) between consecutive injections

The UV detector was operated at 220 nm, 5 Hz sampling rate. The MS device was operated at 3.2 kV capillary voltage, 30 V cone, 2 V extractor, 0.5 V RF lens, 400 L/hr desolvation flow, 100 L/hr cone flow, 100° C. source temperature, 150° C. desolvation temperature, ESI(+) full scan 120-1200 amu acquisition, at 1.7 Hz sampling rate. The CLND detector was operated at 1050° C. furnace temp, 280 mL/min inlet oxygen flow, 80 mL/min inlet argon, 25 mL/min make-up argon, 30 mL/min ozone, 28 torr vacuum, 750 V PMT voltage, PMT chamber at +10° C., sensitivity high, select 5, 4 Hz sampling rate.

HPLC Method 2:

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC Conditions:

Column: Phenomenex Gemini C18, 3 μm, 50×4.6 mm (default)

Temperature: 40° C.

Mobile phase A: Acetate Buffer 5 mM pH 4.5: acetonitrile 95:5 (v:v)

Mobile phase B: Acetate Buffer 5 mM pH 4.5: acetonitrile 5:95 (v:v)

Elution Gradient:

| Time (min) | % Mobile Phase A |
|---|---|
| 0 | 100 |
| 7 | 0 |
| 9 | 0 |
| 11 | 100 |
| 13 | 100 |

Flow rate: 1 mL/min

Injection volume: 10 μL

Column temperature: 40° C.

MS Conditions:

The LCQ mass spectrometer operates with an electrospray ionization (ESI) interface in positive and negative ion mode following the operation parameters reported in table 1. MS/MS experiments are performed on the most intense ion of each scan automatically by Xcalibur software. A 45% collision energy was used for the fragmentation of the precursor ions.

TABLE 1

Mass Spectrometer Instrument parameters

| Parameter | Value |
|---|---|
| Capillary Temperature (° C.) | 255 |
| Source Voltage (kV) | 4.00 |
| Capillary Voltage (V) | 21.0 |

TABLE 1-continued

Mass Spectrometer Instrument parameters

| Parameter | Value |
|---|---|
| Tube Lens Offset (V) | −5.0 |
| Multipole RF Amplifier (Vp-p) | 400.0 |
| Multipole 1 Offset (V) | −3.00 |
| Multipole 2 Offset (V) | −6.50 |
| InterMultipole Lens Voltage (V) | −16.00 |
| Trap DC Offset Voltage (V) | −10.00 |
| Full Micro scans | 3 |
| Full AGC Target Ions | $5*10^7$ |
| Full Max Ion Time (ms) | 150 |
| MSn Micro scans | 3 |
| MSn AGC Target Ions | $2*10^7$ |
| MSn Max Ion Time (ms) | 200 |
| Electron Multiplier (V) | −950.0 |

HPLC Method 3:

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC Conditions:

Column: Phenomenex Gemini C18, 3 µm, 50×4.6 mm (default)

Temperature: 40° C.

Mobile phase A: Acetate Buffer 5 mM pH 4.5: acetonitrile 95:5 (v:v)

Mobile phase B: Acetate Buffer 5 mM pH 4.5: acetonitrile 5:95 (v:v)

Elution Gradient:

| Time (min) | % Mobile Phase A |
|---|---|
| 0 | 100 |
| 2 | 80 |
| 9 | 60 |
| 10 | 0 |
| 12 | 0 |
| 12.10 | 100 |

Flow rate: 1 mL/min
Injection volume: 10 µL
Column temperature: 40° C.
MS Conditions:

The LCQ mass spectrometer operates with an electrospray ionization (ESI) interface in positive and negative ion mode following the operation parameters reported in table 1. MS/MS experiments are performed on the most intense ion of each scan automatically by Xcalibur software. A 45% collision energy was used for the fragmentation of the precursor ions.

TABLE 1

Mass Spectrometer Instrument parameters

| Parameter | Value |
|---|---|
| Capillary Temperature (° C.) | 255 |
| Source Voltage (kV) | 4.00 |
| Capillary Voltage (V) | 21.0 |
| Tube Lens Offset (V) | −5.0 |
| Multipole RF Amplifier (Vp-p) | 400.0 |
| Multipole 1 Offset (V) | −3.00 |
| Multipole 2 Offset (V) | −6.50 |

TABLE 1-continued

Mass Spectrometer Instrument parameters

| Parameter | Value |
|---|---|
| InterMultipole Lens Voltage (V) | −16.00 |
| Trap DC Offset Voltage (V) | −10.00 |
| Full Micro scans | 3 |
| Full AGC Target Ions | $5*10^7$ |
| Full Max Ion Time (ms) | 150 |
| MSn Micro scans | 3 |
| MSn AGC Target Ions | $2*10^7$ |
| MSn Max Ion Time (ms) | 200 |
| Electron Multiplier (V) | −950.0 |

Retention times (HPLC r.t.) are given in minutes at 220 nm or at 254 nm. Mass is given as m/z ratio.

When necessary, the compounds have been purified by preparative HPLC on a Waters X-Bridge Prep Shield RP18 (19×100 mm, 5 µm) column or a Phenomenex Gemini C18 (21.2×250 mm, 10 µm) column, using a Waters FractionLynx Autopurification System equipped with a 996 Waters PDA detector and a Micromass mod. ZQ single quadrupole mass spectrometer, electron spray ionization, positive mode. Mobile phase A was water 0.05% NH3/acetonitrile 95:5, and Mobile phase B was acetonitrile. Gradient from 10 to 90% B in 8 min or 15 min. Flow rate 20 ml/min.

$^1$H-NMR spectrometry was performed on a Bruker AVANCE 400 MHz single bay instrument with gradients. It is equipped with a QNP probe (interchangeable 4 nuclei probe—$^1$H, 13C, 19F and 31P) (NMR method 1) or on a Mercury VX 400 operating at 400.45 MHz equipped with a 5 mm double resonance probe [1H (15N-31P) ID_PFG Varian] (NMR method 2).

The compounds of formula (I), having an asymmetric carbon atom and obtained as racemic mixture, were resolved by HPLC separation on chiral columns. In particular, for example, preparative columns CHIRALPACK® AD, CHIRALPACK® AS, CHIRALCELL° OJ can be used.

As formerly indicated, several compounds of formula (I) of the invention have been synthesized, according to solution and combinatorial chemistry techniques.

In this respect, some compounds thus prepared have been conveniently and unambiguously identified, as per the coding system of tables III together with HPLC retention time (methods 1A, 1B, 2 and 3) and mass.

Each code, which identifies a single specific compound of formula (I), consists of three units A-M-B.

A represents any substituent R1 and R2—[see formula (I)] and is attached to the M central core through the nitrogen in position 3; each A substituent is represented in the following table I.

B represents any substituent R3 [see formula (I)] and is attached to the rest of the M central core through the carbon atom of the carbonyl group; each B substituent is represented in the following table II.

M refers to the central core, more precisely M1 represents 4,5-dihydro-1H-pyrazolo[4,3-g]indolizine core [see formula (I)A] whereas M2 represents 1,4,5,6-tetrahydropyrazolo[3,4-c]pyrrolo[1,2-a]azepine core [see formula (I) B]; each cores being substituted in position 3 by groups A and at the carbonyl group by groups B, substantially as follows:

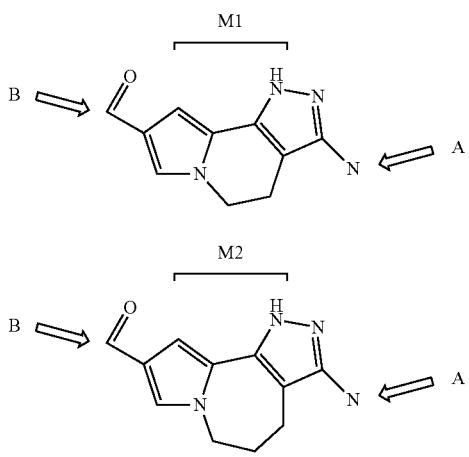

For ease of reference, each A and B groups of tables I and II has been identified with the proper chemical formula also indicating the point of attachment with the rest of the molecule M1 or M2.

Just as an example, the compound A1-M1-B1 (entry 1 of table III) represents a 4,5-dihydro-1H-pyrazolo[4,3-g]indolizine (central core M1), being substituted at the nitrogen in 3-position by the group A1 and at the carbonyl group by the group B1; likewise, the compound A44-M2-B28 (entry 1116 of table III) represents a 1,4,5,6-tetrahydropyrazolo[3,4-c]pyrrolo[1,2-a]azepine (central core M2), being substituted at the nitrogen in 3-position by the group A44 and at the carbonyl group by the group B28.

TABLE I-continued

| FRAGMENT | CODE |
|---|---|
| | A1 |
| | A2 |
| | A3 |
| | A4 |
| | A5 |
| | A6 |
| | A7 |
| | A8 |
| | A9 |
| | A10 |
| | A11 |

TABLE I-continued
| Structure | Label |
|---|---|
| 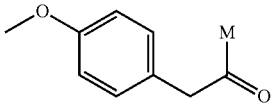 | A12 |
| 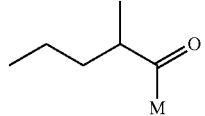 | A13 |
| 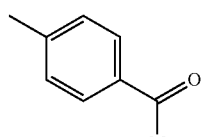 | A14 |
| 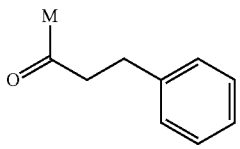 | A15 |
| 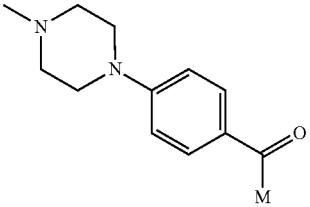 | A16 |
| 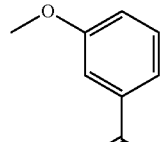 | A17 |
| 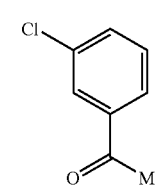 | A18 |
| 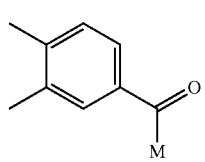 | A19 |
| 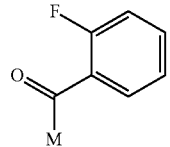 | A20 |
| 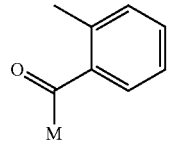 | A21 |
| 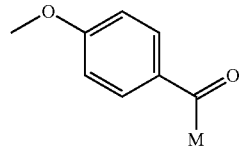 | A22 |
| 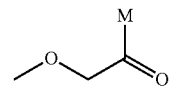 | A23 |
| 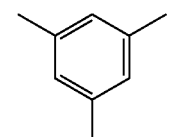 | A24 |
| 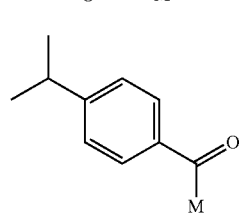 | A25 |
| 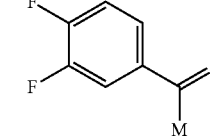 | A26 |
| 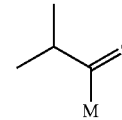 | A27 |
| 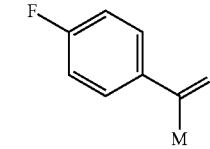 | A28 |
|  | A29 |
| 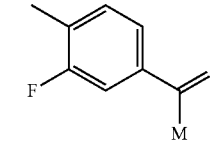 | A30 |
| 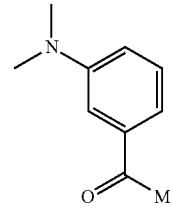 | A31 |

TABLE I-continued
| | |
|---|---|
| 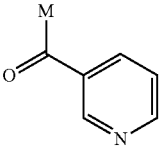 | A32 |
| 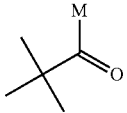 | A33 |
| 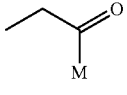 | A34 |
| 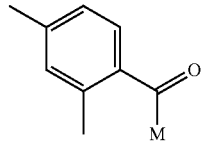 | A35 |
| 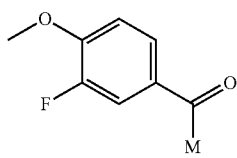 | A36 |
| 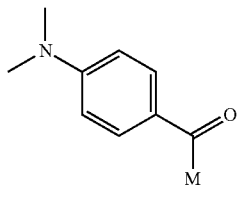 | A37 |
| 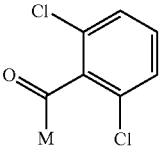 | A38 |
| 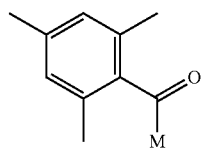 | A39 |
| 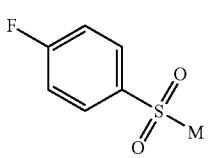 | A40 |
| 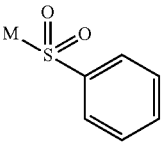 | A41 |
| 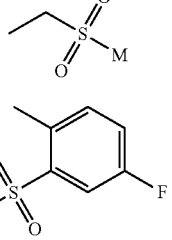 | A42 |
| 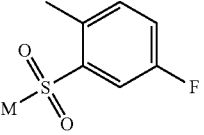 | A43 |
| 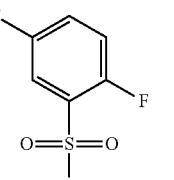 | A44 |
| 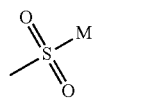 | A45 |
| 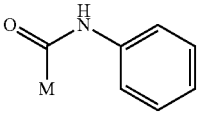 | A46 |
| 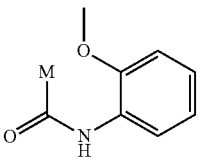 | A47 |
| 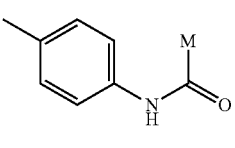 | A48 |
| 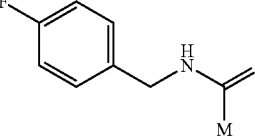 | A49 |
| 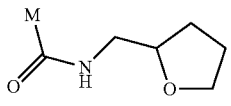 | A50 |
| 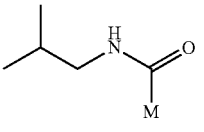 | A51 |
| 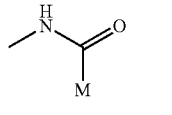 | A52 |
| 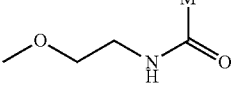 | A53 |

TABLE I-continued
| FRAGMENT | CODE |
|---|---|
| 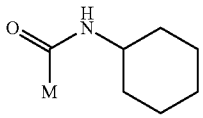 | A54 |
TABLE II
B groups
| FRAGMENT | CODE |
|---|---|
| 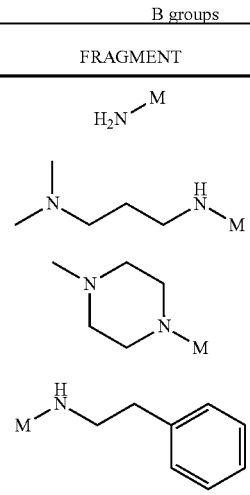 | B1 |
| | B2 |
| | B3 |
| | B4 |
| | B5 |
| | B6 |
| | B7 |
| | B8 |
| | B9 |
| | B10 |
| | B11 |
| | B12 |
TABLE II-continued
B groups
| FRAGMENT | CODE |
|---|---|
| 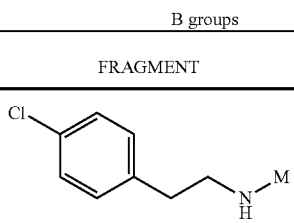 | B13 |
| 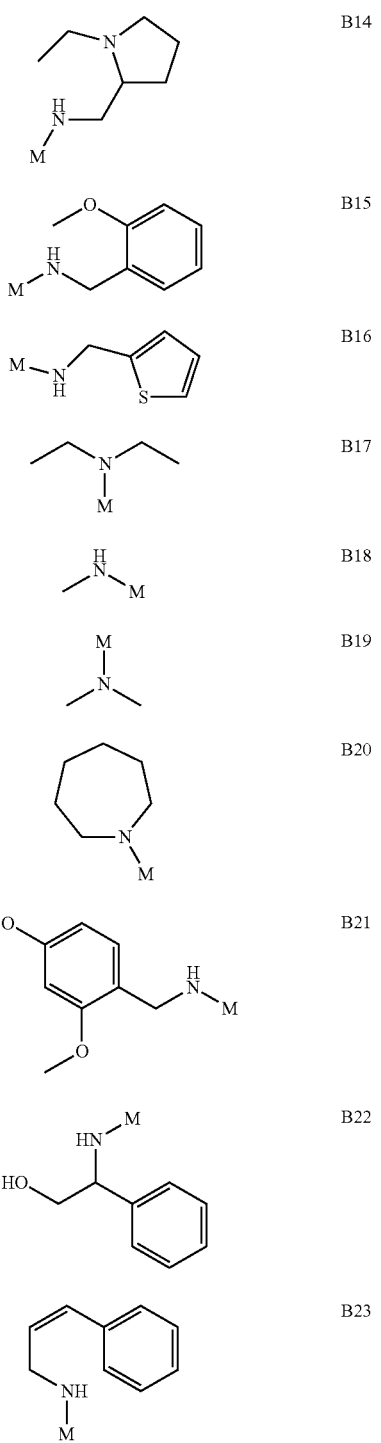 | B14 |
| | B15 |
| | B16 |
| | B17 |
| | B18 |
| | B19 |
| | B20 |
| | B21 |
| | B22 |
| | B23 |

TABLE II-continued

B groups

| FRAGMENT | CODE |
|---|---|
| 1,4-diazepane, N-methyl, N'-M | B24 |
| M-NH-CH2-(pyridin-4-yl) | B25 |
| M-NH-CH2-(pyridin-2-yl) | B26 |
| sec-butyl-NH-M | B27 |
| cyclopentyl-NH-M | B28 |
| (CH3)2N-CH2CH2-NH-M | B29 |
| cyclopropyl-NH-M | B30 |
| M-NH-CH2CH2-(piperidin-1-yl) | B31 |
| 1-propyl-4-M-piperazine | B32 |
| CH3O-CH2CH2-NH-M | B33 |
| 1-M-4-(piperidin-1-yl)piperidine | B34 |
| 1-(pyridin-2-yl)-4-M-piperazine | B35 |
| allyl-NH-M | B36 |
| 1-ethyl-4-M-piperazine | B37 |
| 4-M-thiomorpholine | B38 |
| isobutyl-NH-M | B39 |
| 1-isopropyl-4-M-piperazine | B40 |
| M-NH-CH2-cyclopropyl | B41 |
| 1-M-piperidine | B42 |
| M-NH-CH2CH2-(pyrrolidin-1-yl) | B43 |

Preparation 1

Preparation of Ethyl 1H-pyrrole-2-carboxylate (IV, Wherein Ra' is —CH$_2$—CH$_3$)

A solution of 2,2,2-trichloro-1-(1H-pyrrol-2-yl)-ethanone (25 g, 0.12 mol) in ethanol (200 mL) was treated with potassium carbonate (5 g). The mixture was then heated to reflux for 1 hour. After this time the residue solid was filtered off, and the solution concentrated under reduced pressure. Ethyl acetate (200 mL) was added and washed 2 times with water. The organic phase was dried with anhydrous sodium sulphate to obtain a pale yellow solid (18 g). HPLC (Method 2): m/z 140.12 [M+H]+@ Rt=4.01 min. 1H NMR (400 MHz, DMSO-d6) δ ppm 1.29 (t, J=7.07, 3 H) 4.23 (q, J=7.07, 2 H) 6.04-6.25 (m, 1 H) 6.65-6.86 (m, 1 H) 7.00-7.06 (m, 1 H) 11.83 (br. s., 1 H)

Preparation 2

Preparation of Ethyl 4-(trichloroacetyl)-1H-pyrrole-2-carboxylate (V, Wherein Ra' is —CH$_2$—CH$_3$)

To ethyl 1H-pyrrole-2-carboxylate (18 g, 0.12 mol) dissolved in DCM (200 mL), was added anhydrous AlCl3 (40 g).

After 10 minutes of vigorous stirring was added drop wise a solution of trichloro-acetyl chloride (20 mL) in DCM (100 mL). The reaction was heated to reflux for 3 hours. The mixture was then allowed to reach room temperature and poured in a 2 L backer with iced HCl 6N left stirring for 2 hours. The DCM was extract and washed 2 times with NaHCO3 and water. A dark solid was obtained which was not purified. HPLC (Method 2): m/z 282.45 [M−H] @ Rt=6.55 min. 1H NMR (400 MHz, DMSO-d6) δ ppm 1.32 (s, J=7.07 Hz, 3 H) 4.30 (s, J=7.07 Hz, 2 H) 7.26-7.40 (m, 1 H) 7.85-8.09 (m, 1 H) 13.06 (br. s., 1 H).

Preparation 3

Preparation of Diethyl 1H-pyrrole-2,4-dicarboxylate (VI, Wherein Both of Ra' are —CH$_2$—CH$_3$)

To a solution of ethyl 4-(trichloroacetyl)-1H-pyrrole-2-carboxylate (30 g, 0.12 mol) in ethanol (250 mL) was added potassium carbonate (7 g). The mixture was then heated to reflux for 1 hour. After this time the residue solid was filtered off, and the solution concentrated under vacuum. Ethyl acetate (200 mL) was added and washed 2 times with water. The organic phase was dried with anhydrous sodium sulphate to obtain a brown solid (28 g).

HPLC (Method 2): m/z 212.34 [M+H]+@ Rt=4.79 min. 1H NMR (400 MHz, DMSO-d6) δ ppm 1.26 (t, J=7.07 Hz, 3H) 1.28 (t, J=7.07 Hz, 3H) 4.19 (q, J=7.11 Hz, 2 H) 4.25 (q, J=7.07 Hz, 2 H) 7.06 (dd, J=2.50, 1.65 Hz, 1 H) 7.54 (dd, J=3.35, 1.65 Hz, 1 H) 12.50 (br. s., 1 H)

Preparation 4

Preparation of Diethyl 1-(3-cyanopropyl)-1H-pyrrole-2,4-dicarboxylate (VII, Wherein n is 0 and Both of Ra' are —CH$_2$—CH$_3$)

To diethyl 1H-pyrrole-2,4-dicarboxylate (28 g, 0.13 mol) dissolved in ACN was added 30 g of potassium carbonate (0.21 mol) and 17 mL of 4-bromo-butyronitrile (0.14 mol, d=1.3). The reaction was refluxed over night. The solvent was then evaporated under reduced pressure, the residue dissolved in ethyl acetate and washed 2 times with water. The crude was purified with a silica column (10 p silica) eluent cycloesane/ethyl acetate 7:3. 20 g of a white solid was obtained.

HPLC (Method 2): m/z 296.51 [M+NH4+]+@ Rt=5.88 min. 1H NMR (400 MHz, DMSO-d6) δ ppm 1.24 (t, J=7.07 Hz, 3H) 1.27 (t, J=7.07 Hz, 3H) 2.03 (m, 2H) 2.48 (t, J=7.19 Hz, 2H) 4.19 (q, J=7.07 Hz, 2 H) 4.24 (q, J=7.07 Hz, 2 H) 4.38 (t, J=7.19 Hz, 2H) 7.16 (d, J=1.95 Hz, 1 H) 7.80 (d, J=1.83 Hz, 1 H)

Preparation 5

Preparation of Ethyl 7-cyano-8-oxo-5,6,7,8-tetrahydroindolizine-2-carboxylate (VIII, Wherein n is 0 and Ra' is —CH$_2$—CH$_3$)

To the diethyl 1-(3-cyanopropyl)-1H-pyrrole-2,4-dicarboxylate (7 g) dissolved in anhydrous THF (150 mL), under nitrogen atmosphere, a solution of TertBuOK 1N in THF (50 mL) was added drop wise. The reaction was left stirring. After 15 minutes water and citric acid were added (pH≅5), after 30 minutes of vigorous stirring the solution was extract with 100 mL of ethyl acetate. The organic phase was then washed with water and NaHCO3 (pH≅10) dried on anhydrous Na2SO4. 5 g of a white solid were obtained (yield 87%). HPLC (Method 2): m/z 250.31 [M+NH4+]+@ Rt=4.23 min. 1H NMR (400 MHz, DMSO-d6) (mixture of tautomers cheto/enolic form ratio 56:44) δ ppm 1.26 (t, J=7.07 Hz, 3 H 56%) 1.28 (t, J=7.07 Hz, 3 H 44%) 2.62 (m, 2 H) 4.06 (t, J=6.83 Hz, 2 H 44%) 4.17 (q, J=7.07 Hz, 2 H 56%) 4.20 (q, J=7.07 Hz, 2 H 44%) 4.38 (dt, J=12.19 J=4.02 Hz, 2 H 56%) 4.51 (dd, J=11.24 J=5.08 Hz, 1 H 56%) 7.00 (d, J=1.59 Hz, 1H 44%) 7.23 (d, J=1.71, 1 H 56%) 7.65 (d, J=1.59, 1H 44%) 7.85 (d, J=1.59, 1H 56%) 10.96 (s, 1H 44% OH enolic)

Example 1

Preparation of the Ethyl 3-amino-4,5-dihydro-1H-pyrazolo[4,3-g]indolizine-8-carboxylate (I, Wherein n is 0, R1, R2 and R4 are Hydrogen, and R3 is —O—CH$_2$—CH$_3$)

To ethyl 7-cyano-8-oxo-5,6,7,8-tetrahydroindolizine-2-carboxylate (12 g, 52 mmol) in ethanol a solution of hydrazine monohydrate (6.5 g, 130 mmol) and acetic acid (9 g, 150 mmol) was added. The reaction was refluxed for 62 hours and concentrated under reduced pressure. The residue was dissolved in ethyl acetate and washed with water and NH3. The organic phase was dried on Na2SO4. 10 g of a pale yellow solid were obtained (yield 78%).

HPLC(Method 2): m/z 247.25 [M+H]+@ Rt=3.17 min. 1H NMR (400 MHz, DMSO-d6) δ ppm 1.25 (t, J=7.13 Hz, 3 H) 2.69 (t, J=6.71 Hz, 2 H) 4.05 (t, J=6.71 Hz, 2 H) 4.17 (q, J=7.07 Hz, 2 H) 4.40-5.13 (m, 2 H) 6.48 (br. s., 2H) 7.49 (s, 1 H) 11.49 (br. s., 1 H)

Example 2

Preparation of Compound Ethyl 3-[(trifluoroacetyl)amino]-4,5-dihydro-1H-pyrazolo[4,3-g]indolizine-8-carboxylate (I, Wherein n is 0, R1 is —COCF3, R2 and R4 are Hydrogen, and R3 is —O—CH$_2$—CH$_3$)

To the compound ethyl 3-amino-4,5-dihydro-1H-pyrazolo[4,3-g]indolizine-8-carboxylate (5 g, 20.3 mmol) in DCM, was added TEA (11 g, 110 mmol) and TFAA (21 g 100 mmol). The reaction mixture was stirred at room temperature for 3 hours and then concentrated in vacuo. To the residue diluted NH3 and MeOH were added and stirred for 1 hour. The solution was then concentrated. 100 mL of water was added and extracted with ethylacetate (3×100 mL).The organic phase was dried with anhydrous sodium sulphate to obtain a pale yellow solid (6.5 g, 92%).

LCMS (HPLC Method 2): m/z 343 [M+H]+@ Rt 4.75 min (100% by ELS detection).

1H NMR (400 MHz, DMSO-D6) δ ppm 13.13 (s, 1 H) 11.61 (s, 1 H) 7.62 (s, 1 H) 6.68 (s, 1 H) 4.21 (q, J=7.07 Hz, 2 H) 4.13 (t, J=6.83 Hz, 2 H) 2.81 (t, J=6.77 Hz, 2 H) 1.28 (t, J=7.13 Hz, 3 H)

Preparation 6

Preparation of Solid Supported 3-amino-4,5-dihydro-1H-pyrazolo[4,3-g]indolizine-8-carboxylic acid (XVII, Wherein n is 0)

To polystyrene trityl chloride resin (Aldrich, loading 1.73 mmol/g) swelled in DCM a solution of ethyl 3-[(trifluoroacetyl)amino]-4,5-dihydro-1H-pyrazolo[4,3-g]indolizine-8-carboxylate (1.5 eq) and TEA (2 eq) in DCM (10 ml 1 g) was added. The mixture was shaken for 24 hrs at room temperature. The resin was filtered off, washed with DMF (3×), DCM (3×), MeOH (3×), DCM, MeOH, DCM, MeOH, DCM (3×) and the unreacted chlorides were capped washing the resin with a solution of TEA/MeOH/DCM (1:2:7) (2×). Then the resin was washed with DCM (3×), MeOH (3×), DCM (3×) and dried under vacuum. Usually loading is over 90%: Calculated loading with increase of weight was 1.00 mmol/g The resin was then used in the next step.

The resin obtained from the first step was then treated with a solution of NaOH (40 eq), H2O (1 ml/12 mmol NaOH), THF (2 ml/12 mmol NaOH) and minimal amount of MeOH to give a homogeneous solution.

The reaction was left shaking for 72 hrs at 50° C. Then was filtered off and washed sequentially with DMF (3×), MeON (3×), Water, MeOH, DCM, MeOH, DCM (3×).

After a check cleavage (40% TFA in DCM r.t. 30 min) the LCMS (HPLC Method 2) m/z 219 [M+H]+@ Rt 1.02 min (100% by ELS detection), the title compound was obtained.

Preparation 7

Preparation of Diethyl 1-(4-cyanobutyl)-1H-pyrrole-2,4-dicarboxylate (VII, Wherein n is 1 and Both of Ra' are —CH$_2$—CH$_3$)

To diethyl 1H-pyrrole-2,4-dicarboxylate (28 g, 0.13 mol) dissolved in ACN was added 30 g of potassium carbonate (0.21 mol) and 16.5 mL of 5-bromo-pentanenitrile (0.14 mol, d=1.377). The reaction was refluxed over night. The solvent was then evaporated under reduced pressure, the residue dissolved in ethyl acetate and washed 2 times with water. The crude was purified with a silica column (10 p silica) eluent cycloesane/ethyl acetate 7:3. 20 g of a white solid was obtained. HPLC (Method 2): m/z 293.51 [M+H+]+@ Rt=5.61 min. 1H NMR (400 MHz, DMSO-d6) δ ppm 1.23-1.34 (m, 6 H), 1.42-1.56 (m, 2 H), 1.73-1.85 (m, 2 H), 3.27-3.28 (m, 2 H), 4.16-4.30 (m, 4 H), 4.36 (t, J=7.0 Hz, 2 H), 7.17 (d, J=2.0 Hz, 1 H), 7.83 (d, J=2.0 Hz, 1 H).

Preparation 8

Preparation of Ethyl 8-cyano-9-oxo-6,7,8,9-tetrahydro-5H-pyrrolo[1,2-a]azepine-2-carboxylate (VIII, Wherein n is 1 and Ra' is —CH$_2$—CH$_3$)

To the diethyl 1-(4-cyanobutyl)-1H-pyrrole-2,4-dicarboxylate (7 g) dissolved in anhydrous THF (150 mL), under nitrogen atmosphere, a solution of TertBuOK 1N in THF (50 mL) was added drop wise. The reaction was left stirring. After 15 minutes water and citric acid were added (pH≅5), after 30 minutes of vigorous stirring the solution was extract with 100 mL of Ethyl acetate. The organic phase was then washed with water and NaHCO3 (pH≅10) dried on anhydrous Na2SO4. 5 g of a white solid were obtained (yield 87%). HPLC (Method 2): m/z 264 [M+NH4+]+@ Rt=4.6 min. 1H NMR (400 MHz, DMSO-d6) (mixture of tautomers cheto/enolic form ratio 55:45) ppm 1.35 (t, J=7.07 Hz, 3 H) 1.91-2.23 (m, 6H) 2.35 (m, 2 H) 3.95 (t, J=6.83 Hz, 2 H 45%) 4.21 (q, J=7.07 Hz, 2 H 55%) 4.23 (q, J=7.07 Hz, 2 H 45%) 4.51 (dt, J=12.19 J=4.02 Hz, 2 H 55%) 4.57 (m, 1 H 55%) 7.12 (d, J=1.59 Hz, 1 H 45%) 7.17 (d, J=1.71, 1 H 55%) 7.31 (d, J=1.59, 1 H 45%) 7.70 (d, J=1.59, 1H 55%) 10.82 (s, 1H 45% OH enolic)

Example 3

Preparation of the Ethyl 3-amino-1,4,5,6-tetrahydro-pyrazolo[3,4-c]pyrrolo[1,2-a]azepine-9-carboxylate (I, Wherein n is 1, R1, R2 and R4 are Hydrogen, and R3 is —O—CH$_2$—CH$_3$)

To ethyl 8-cyano-9-oxo-6,7,8,9-tetrahydro-5H-pyrrolo[1,2-a]azepine-2-carboxylate (12 g, 49 mmol) in ethanol a solution of hydrazine monohydrate (6.5 g, 130 mmol) and acetic acid (9 g, 150 mmol) was added. The reaction was refluxed for 62 hours and concentrated under reduced pressure. The residue was dissolved in ethyl acetate and washed with water and NH3. The organic phase was dried on Na2SO4. 10 g of a pale yellow solid were obtained (yield 78%).

HPLC(Method 2): m/z 261.3 [M+H]+@ Rt=3.13 min. 1H NMR (400 MHz, DMSO-d6) δ ppm 1.25 (t, J=7.1 Hz, 3 H) 2.54 (t, J=6.3 Hz, 2 H), 4.17 (q, J=7.2 Hz, 2 H), 4.10-4.23 (m, 2 H), 4.44 (br. s., 1 H), 6.82 (d, J=1.8 Hz, 1 H), 7.43 (d, J=2.0 Hz, 1 H), 11.70 (br. s., 1 H).

Example 4

Preparation of Compound Ethyl 3-[(trifluoroacetyl) amino]-1,4,5,6-tetrahydropyrazolo[3,4-c]pyrrolo[1,2-a]azepine-9-carboxylate (I, Wherein n is 1, R1 is —COCF3, R2 and R4 are Hydrogen, and R3 is —O—CH$_2$—CH$_3$)

To the compound ethyl 3-amino-1,4,5,6-tetrahydropyrazolo[3,4-c]pyrrolo[1,2-a]azepine-9-carboxylate (5 g, 19.2 mmol) in DCM, was added TEA (11 g, 110 mmol) and TFAA (21 g 100 mmol). The reaction mixture was stirred at room temperature for 3 hours and then concentrated in vacuo. To the residue diluted NH3 and MeOH were added and stirred for 1 hour. The solution was then concentrated. 100 mL of water was added and extracted with ethylacetate (3×100 mL).The organic phase was dried with anhydrous sodium sulphate to obtain a pale yellow solid (6.5 g, 92%). LCMS (HPLC Method 2): m/z 357 [M+H]+@ Rt 4.76 min (100% by ELS detection).

1H NMR (400 MHz, DMSO-D6) δ ppm 1.26 (t, J=7.1 Hz, 3 H) 1.94-2.05 (m, 2 H), 2.54-2.60 (m, 2 H), 4.16-4.21 (m, 2 H), 4.21-4.24 (m, 2 H), 7.02 (d, J=2.0 Hz, 1 H), 7.53 (d, J=1.8 Hz, 1 H), 11.27 (s, 1 H), 12.96 (br. s., 1 H).

Preparation 9

Preparation of Solid Supported 3-amino-1,4,5,6-tetrahydropyrazolo[3,4-c]pyrrolo[1,2-a]azepine-9-carboxylic acid (XVII, Wherein n is 1)

To polystyrene trityl chloride resin (Aldrich, loading 1.73 mmol/g) swelled in DCM a solution of ethyl 3-[(trifluoroacetyl)amino]-1,4,5,6-tetrahydropyrazolo[3,4-c]pyrrolo[1,2-a]azepine-9-carboxylate (1.5 eq) and TEA (2 eq) in DCM (10 ml/g) was added. The mixture was shaken for 24 hrs at room temperature. The resin was filtered off, washed with DMF (3×), DCM (3×), MeOH (3×), DCM, MeOH, DCM, MeOH, DCM (3×) and the unreacted chlorides were capped washing the resin with a solution of TEA/MeOH/DCM (1:2:7) (2×). Then the resin was washed with DCM (3×), MeOH (3×), DCM (3×) and dried under vacuum. Usually loading is over 90%: Calculated loading with increase of weight was 1.00 mmol/g. The resin was then used in the next step.

The resin obtained from the first step was then treated with a solution of NaOH (40 eq), H2O (1 ml/12 mmol NaOH), THF (2 ml/12 mmol NaOH) and minimal amount of MeOH to give a homogeneous solution.

The reaction was left shaking for 72 hrs at 50° C. Then was filtered off and washed sequentially with DMF (3×), MeOH (3×), Water, MeOH, DCM, MeOH, DCM (3×).

After a check cleavage (40% TFA in DCM room temperature for 30 min) the LCMS (HPLC Method 2) m/z 233 [M+H]+ @ Rt 1.15 min (100% by ELS detection), the title compound was obtained.

Example 6

Preparation A5-M1-B36 (entry 443, Table III)

To the 3-amino-4,5-dihydro-1H-pyrazolo[4,3-g]indolizine-8-carboxylic acid bond on resin (XVII, prepared as described under preparation 6), suspended in a solution of DCM/DMF 1:1 v/v, 1.5 eq of EDC, 1.5 eq of HOBT, 5 eq of TEA and 5 eq of allylamine were added. The suspension was left shaking for 24 hours at room temperature. The resin was filtered off, washed with DMF (3×), DCM (3×), MeOH (3×), DCM, MeOH, DCM, MeOH, DCM (3×). After cleavage (TFA/DCM 40%) the product was found in LCMS 90% pure.

To the resultant 3-amino-N-prop-2-en-1-yl-4,5-dihydro-1H-pyrazolo[4,3-g]indolizine-8-carboxamide bond resin (loading 1 mmol/g) (XVIII) suspended in DCM, 5 eq of 2-chloro-benzoyl chloride, and 5.1 eq. of Pyridine were added. The suspension was left shaking over night. The resin was filtered off, washed with DMF (3×), DCM (3×), MeOH (3×), DCM, MeOH, DCM, MeOH, DCM (3×). The resultant 3-{bis[(2-chlorophenyl)carbonyl]amino}-N-prop-2-en-1-yl-4,5-dihydro-1H-pyrazolo[4,3-g]indolizine-8-carboxamide obtained but not isolated (XIX), was suspended in a solution of NaOH 1N in DMF (1:4 v/v) and was left shaking over night at room temperature. Then washed with DMF (3×), MeOH (3×), water, MeOH, DCM, MeOH, DCM (3×). After cleavage (TFA/DCM 40%) the title product was recovered and analyzed.

LCMS (HPLC Method 1A) m/z 392 [M+H]+@ Rt2.72 min (100% by UV:MS:CLND detection).

Example 7

Preparation A42-M2-B42 (entry 1187, Table III)

To the 3-amino-1,4,5,6-tetrahydropyrazolo[3,4-c]pyrrolo[1,2-a]azepine-9-carboxylic acid bond on resin (XVII, prepared as described under preparation 9), suspended in a solution of DCM/DMF 1:1 v/v, 1.5 eq of EDC, 1.5 eq of HOBT, 5 eq of TEA and 5 eq of piperidine were added. The suspension was left shaking for 24 hours at room temperature. The resin was filtered off, washed with DMF (3×), DCM (3×), MeOH (3×), DCM, MeOH, DCM, MeOH, DCM (3×). After a check cleavage (TFA/DCM 40%) the product was found in LCMS 90% pure.

To the resultant (3-amino-1,4,5,6-tetrahydropyrazolo[3,4-c]pyrrolo[1,2-a]azepin-9-yl)(piperidin-1-yl)methanone bond resin (loading 1 mmol/g) (XVIII) suspended in DCM, 5 eq of ethanesulphonyl chloride, and 5.1 eq. of Pyridine were added. The suspension was left shaking 24 hours at room temperature. The resin was filtered off, washed with DMF (3×), DCM (3×), MeOH (3×), DCM, MeOH, DCM, MeOH, DCM (3×). A mixture of desiderate compound and the bis-sulphonil derivative was detected.

To the resultant mixture of compounds resin (loading 1 mmol/g) a solution of 0.1M TBAF in THF was added and was shaken for 35 hours at room temperature. after that time the resin was washed off with DMF 3×, MeOH, DMF, MeOH, DCM, MeOH, DCM 3×. After cleavage (TFA/DCM 40%) the title product was recovered and analyzed.

LCMS (HPLC Method 1A) m/z 396 [M+H]+@ Rt 2.68 min (100% by UV:MS:CLND detection).

Example 8

Preparation A47-M2-B27 (entry 1526, Table III)

To the 3-amino-1,4,5,6-tetrahydropyrazolo[3,4-c]pyrrolo[1,2-a]azepine-9-carboxylic acid bond on resin (XVII, prepared as described under preparation 9), suspended in a solution of DCM/DMF 1:1 v/v, 1.5 eq of EDC, 1.5 eq of HOBT, 5 eq of TEA and 5 eq of racemic butan-2-amine were added. The suspension was left shaking for 24 hours at room temperature. The resin was filtered off, washed with DMF (3×), DCM (3×), MeOH (3×), DCM, MeOH, DCM, MeOH, DCM (3×). After a check cleavage (TFA/DCM 40%) the product was found in LCMS 90% pure.

To the resultant 3-amino-N-(butan-2-yl)-1,4,5,6-tetrahydropyrazolo[3,4-c]pyrrolo[1,2-a]azepine-9-carboxamide bond resin (loading 1 mmol/g) (XVIII), swollen in DCM, was added TEA (10 eq), and 1-isocyanato-2-methoxybenzene (10 eq) and left shaking over night at room temperature. The resin was filtered off, washed with DMF (3×), DCM (3×), MeOH (3×), DCM, MeOH, DCM, MeOH, DCM (3×). After cleavage (TFA/DCM 40%) the title product was recovered and analyzed.

LCMS (HPLC Method 1A) m/z 437 [M+H]+@ Rt 3.42 min (100% by UV:MS:CLND detection).

Example 9

Preparation A1-M1-B1 (entry 1, Table III)

To the ethyl 3-amino-4,5-dihydro-1H-pyrazolo[4,3-g]indolizine-8-carboxylate (prepared as described under Example 1) dissolved in a solution of THF, 5 eq of TEA and later on 2.5 eq of benzoyl chloride were added. The suspension was left shaking for 6 hours at room temperature. A LCMS reveal a poli-acetylation. The solvent was evaporated and the residue was then diluted with water and extracted with EtOAc (2×). The combined organic layers were dried over Na2SO4, the solvent evaporated under vacuum and the product has not been isolated. To the poli-acetylated mixture obtained from the first step a solution 2N NaOH was add. The suspension was heated to 60° C. until a limpid solution was obtained. Ethyl ether was then added and the phase separated. HCl 2N was then added to the water solution until neutrality was reached. The formed precipitate and was separated and dried under vacuum. The 3-[(phenylcarbonyl)amino]-4,5-dihydro-1H-pyrazolo[4,3-g]indolizine-8-carboxylic acid was recovered.

LCMS (HPLC Method 2) m/z 323 [M+H]+@ Rt 1.35 min (100% by ELS detection). 1H NMR (DMSO-d6, 400 MHz): δ ppm: 2.62 (t, J=6.7 Hz, 2 H), 4.13 (t, J=6.7 Hz, 2 H), 6.65 (d, J=1.2 Hz, 1 H), 7.31 (d, J=8.2 Hz, 2 H), 7.43 (d, J=1.7 Hz, 1 H), 7.59 (t, J=7.19 Hz, 1H), 8.01 (d, J=8.6 Hz, 2 H), 10.51 (s, 1 H), 11.81 (br. s., 1 H) 12.88 (br. s., 1 H).

To the resultant carboxylic acid derived, 2 eq of EDC and 3 eq of HOBT.NH4 were dissolved in DMF and left shaken over night at room temperature. Then water and EtOAc were added, the layer separated and the water was extracted with ethyl acetate a second time. The organic layer were combined, dried and evaporated under vacuum. The title compound was purified with preparative HPLC.

LCMS m/z 339 [M+NH4]+@ Rt 2.87 min. 1H NMR (DMSO-d6, 400 MHz): δ ppm: 1H NMR (DMSO-d6, 400 MHz): δ ppm=2.86 (t, J=6.8 Hz, 2 H), 4.08 (t, J=6.7 Hz, 2 H), 6.69 (d, J=1.6 Hz, 1 H), 6.77 (br. S, 1H), 7.34 (br. s, 1H), 7.45 (d, J=1.5 Hz, 1 H), 7.51-7.57 (m, 2 H), 7.62 (t, J=7.3 Hz, 1 H), 8.02 (d, J=7.3 Hz, 2 H), 10.54 (s, 1 H).

Following the procedure described in examples 1 to 9 and by using any proper reactant as per the process of the invention, the following compounds of table III were also prepared.

TABLE III

| Entry | Compound | HPLC method | HPLC RT min | [M + H]+ |
|---|---|---|---|---|
| 1 | A1-M1-B1 | 2 | 2.87 | 322 |
| 2 | A2-M1-B1 | 2 | 2.97 | 336 |
| 3 | A3-M1-B1 | 2 | 2.18 | 286 |
| 4 | A1-M1-B2 | 2 | 2.45 | 407 |
| 5 | A1-M1-B3 | 1A | 1.91 | 405 |
| 6 | A1-M1-B4 | 2 | 4.08 | 426 |
| 7 | A1-M1-B5 | 2 | 3.98 | 404 |
| 8 | A1-M1-B6 | 1A | 2.54 | 350 |
| 9 | A4-M1-B7 | 1A | 2.52 | 372 |
| 10 | A5-M1-B8 | 1A | 2.85 | 410 |
| 11 | A6-M1-B9 | 2 | 4.28 | 432 |
| 12 | A7-M1-B10 | 2 | 3.63 | 384 |
| 13 | A8-M1-B11 | 1B | 6.6 | 452 |
| 14 | A9-M1-B11 | 1B | 6.1 | 424 |
| 15 | A10-M1-B11 | 1B | 7.13 | 454 |
| 16 | A11-M1-B11 | 1B | 6.43 | 478 |
| 17 | A12-M1-B11 | 1B | 6.43 | 478 |
| 18 | A13-M1-B11 | 1B | 6.7 | 428 |
| 19 | A14-M1-B12 | 1B | 5.62 | 440 |
| 20 | A15-M1-B12 | 1B | 5.7 | 454 |
| 21 | A12-M1-B12 | 1B | 5.34 | 470 |
| 22 | A13-M1-B12 | 1B | 5.63 | 420 |
| 23 | A14-M1-B13 | 1B | 6.19 | 474 |
| 24 | A15-M1-B13 | 1B | 6.26 | 488 |
| 25 | A8-M1-B13 | 1B | 6.09 | 478 |
| 26 | A9-M1-B13 | 1B | 5.53 | 450 |
| 27 | A15-M1-B11 | 1B | 6.74 | 462 |
| 28 | A8-M1-B12 | 1B | 5.49 | 444 |
| 29 | A9-M1-B12 | 1B | 4.84 | 416 |
| 30 | A10-M1-B12 | 1B | 6.24 | 446 |
| 31 | A11-M1-B12 | 1B | 5.29 | 470 |
| 32 | A10-M1-B13 | 1B | 6.71 | 480 |
| 33 | A11-M1-B13 | 1B | 5.9 | 504 |
| 34 | A12-M1-B13 | 1B | 5.94 | 504 |
| 35 | A13-M1-B13 | 1B | 6.22 | 454 |
| 36 | A14-M1-B14 | 1B | 3.31 | 447 |
| 37 | A15-M1-B14 | 1B | 3.3 | 461 |
| 38 | A8-M1-B14 | 1B | 3.12 | 451 |
| 39 | A9-M1-B14 | 1B | 2.65 | 423 |
| 40 | A10-M1-B14 | 1B | 3.86 | 453 |
| 41 | A11-M1-B14 | 1B | 3.02 | 477 |
| 42 | A12-M1-B14 | 1B | 3.06 | 477 |
| 43 | A13-M1-B14 | 1B | 3.18 | 427 |
| 44 | A14-M1-B15 | 1B | 5.55 | 456 |
| 45 | A15-M1-B15 | 1B | 5.62 | 470 |
| 46 | A8-M1-B15 | 1B | 5.42 | 460 |
| 47 | A9-M1-B15 | 1B | 4.75 | 432 |
| 48 | A10-M1-B15 | 1B | 6.15 | 462 |
| 49 | A11-M1-B15 | 1B | 5.21 | 486 |
| 50 | A12-M1-B15 | 1B | 5.26 | 486 |
| 51 | A13-M1-B15 | 1B | 5.55 | 436 |
| 52 | A14-M1-B16 | 1B | 5.28 | 432 |
| 53 | A15-M1-B16 | 1B | 5.35 | 446 |
| 54 | A8-M1-B16 | 1B | 5.13 | 436 |
| 55 | A13-M1-B16 | 1B | 5.26 | 412 |
| 56 | A9-M1-B16 | 1B | 4.41 | 408 |
| 57 | A10-M1-B16 | 1B | 5.94 | 438 |
| 58 | A11-M1-B16 | 1B | 4.93 | 462 |
| 59 | A12-M1-B16 | 1B | 4.97 | 462 |
| 60 | A14-M1-B11 | 1B | 6.67 | 448 |
| 61 | A16-M1-B10 | 2 | 2.52 | 462 |
| 62 | A16-M1-B17 | 2 | 2.82 | 476 |
| 63 | A16-M1-B18 | 2 | 2 | 434 |
| 64 | A16-M1-B19 | 2 | 2.3 | 448 |
| 65 | A1-M1-B20 | 2 | 4.35 | 404 |
| 66 | A1-M1-B21 | 2 | 4.53 | 472 |
| 67 | A1-M1-B22 | 2 | 3.92 | 442 |
| 68 | A1-M1-B23 | 2 | 4.9 | 438 |
| 69 | A17-M1-B24 | 1A | 2.08 | 449 |
| 70 | A18-M1-B24 | 1A | 2.39 | 453 |
| 71 | A3-M1-B24 | 1A | 1.67 | 383 |
| 72 | A19-M1-B24 | 1A | 2.5 | 447 |
| 73 | A20-M1-B24 | 1A | 1.96 | 437 |
| 74 | A11-M1-B24 | 1A | 1.96 | 463 |
| 75 | A21-M1-B24 | 1A | 2.04 | 433 |
| 76 | A22-M1-B24 | 1A | 2.03 | 449 |
| 77 | A4-M1-B24 | 1A | 1.92 | 399 |
| 78 | A6-M1-B24 | 1A | 2.17 | 449 |
| 79 | A23-M1-B24 | 1A | 1.52 | 387 |
| 80 | A24-M1-B24 | 1A | 2.58 | 447 |
| 81 | A25-M1-B24 | 1A | 2.86 | 461 |
| 82 | A26-M1-B24 | 1A | 2.26 | 455 |
| 83 | A27-M1-B24 | 1A | 1.7 | 385 |
| 84 | A28-M1-B24 | 1A | 2.07 | 437 |
| 85 | A29-M1-B24 | 1A | 1.46 | 357 |
| 86 | A8-M1-B24 | 1A | 2.08 | 437 |
| 87 | A30-M1-B24 | 1A | 2.37 | 451 |
| 88 | A17-M1-B25 | 1A | 2.18 | 443 |
| 89 | A31-M1-B25 | 1A | 2.06 | 456 |
| 90 | A18-M1-B25 | 1A | 2.51 | 447 |
| 91 | A3-M1-B25 | 1A | 1.75 | 377 |
| 92 | A19-M1-B25 | 1A | 2.58 | 441 |
| 93 | A20-M1-B25 | 1A | 2.07 | 431 |
| 94 | A32-M1-B25 | 1A | 1.67 | 414 |
| 95 | A11-M1-B25 | 1A | 2.08 | 457 |
| 96 | A21-M1-B25 | 1A | 2.14 | 427 |
| 97 | A24-M1-B25 | 1A | 2.67 | 441 |
| 98 | A26-M1-B25 | 1A | 2.37 | 449 |
| 99 | A33-M1-B25 | 1A | 1.95 | 393 |
| 100 | A5-M1-B25 | 1A | 2.12 | 447 |
| 101 | A27-M1-B25 | 1A | 1.79 | 379 |
| 102 | A28-M1-B25 | 1A | 2.2 | 431 |
| 103 | A29-M1-B25 | 1A | 1.52 | 351 |
| 104 | A1-M1-B25 | 1A | 2.07 | 413 |
| 105 | A8-M1-B25 | 1A | 2.2 | 431 |
| 106 | A17-M1-B26 | 1A | 2.32 | 443 |
| 107 | A31-M1-B26 | 1A | 2.19 | 456 |
| 108 | A18-M1-B26 | 1A | 2.65 | 447 |
| 109 | A3-M1-B26 | 1A | 1.87 | 377 |
| 110 | A19-M1-B26 | 1A | 2.73 | 441 |
| 111 | A20-M1-B26 | 1A | 2.19 | 431 |
| 112 | A32-M1-B26 | 1A | 1.78 | 414 |
| 113 | A11-M1-B26 | 1A | 2.2 | 457 |
| 114 | A21-M1-B26 | 1A | 2.29 | 427 |
| 115 | A22-M1-B26 | 1A | 2.29 | 443 |
| 116 | A6-M1-B26 | 1A | 2.4 | 443 |
| 117 | A24-M1-B26 | 1A | 2.83 | 441 |
| 118 | A26-M1-B26 | 1A | 2.55 | 449 |
| 119 | A33-M1-B26 | 1A | 2.09 | 393 |
| 120 | A5-M1-B26 | 1A | 2.25 | 447 |
| 121 | A34-M1-B26 | 1A | 1.76 | 365 |
| 122 | A27-M1-B26 | 1A | 1.91 | 379 |
| 123 | A28-M1-B26 | 1A | 2.33 | 431 |
| 124 | A1-M1-B26 | 1A | 2.18 | 413 |
| 125 | A8-M1-B26 | 1A | 2.35 | 431 |
| 126 | A17-M1-B27 | 1A | 3.01 | 408 |
| 127 | A31-M1-B27 | 1A | 2.89 | 421 |
| 128 | A18-M1-B27 | 1A | 3.37 | 412 |
| 129 | A3-M1-B27 | 1A | 2.6 | 342 |
| 130 | A19-M1-B27 | 1A | 3.39 | 406 |
| 131 | A20-M1-B27 | 1A | 2.92 | 396 |
| 132 | A32-M1-B27 | 1A | 2.43 | 379 |
| 133 | A21-M1-B27 | 1A | 3.03 | 392 |
| 134 | A6-M1-B27 | 1A | 3.1 | 408 |
| 135 | A23-M1-B27 | 1A | 2.34 | 346 |
| 136 | A24-M1-B27 | 1A | 3.46 | 406 |
| 137 | A25-M1-B27 | 1A | 3.69 | 420 |
| 138 | A26-M1-B27 | 1A | 3.27 | 414 |
| 139 | A35-M1-B27 | 1A | 3.32 | 406 |
| 140 | A33-M1-B27 | 1A | 2.83 | 358 |
| 141 | A5-M1-B27 | 1A | 2.99 | 412 |
| 142 | A28-M1-B27 | 1A | 3.06 | 396 |
| 143 | A1-M1-B27 | 1A | 2.92 | 378 |
| 144 | A8-M1-B27 | 1A | 3.08 | 396 |
| 145 | A30-M1-B27 | 1A | 3.36 | 410 |
| 146 | A17-M1-B28 | 1A | 3.11 | 420 |
| 147 | A31-M1-B28 | 1A | 3.02 | 433 |
| 148 | A18-M1-B28 | 1A | 3.45 | 424 |
| 149 | A3-M1-B28 | 1A | 2.73 | 354 |
| 150 | A19-M1-B28 | 1A | 3.48 | 418 |
| 151 | A20-M1-B28 | 1A | 3.04 | 408 |
| 152 | A32-M1-B28 | 1A | 2.58 | 391 |
| 153 | A11-M1-B28 | 1A | 3.04 | 434 |
| 154 | A21-M1-B28 | 1A | 3.14 | 404 |

TABLE III-continued

| Entry | Compound | HPLC method | HPLC RT min | [M + H]+ |
|---|---|---|---|---|
| 155 | A4-M1-B28 | 1A | 3.08 | 370 |
| 156 | A6-M1-B28 | 1A | 3.21 | 420 |
| 157 | A23-M1-B28 | 1A | 2.48 | 358 |
| 158 | A24-M1-B28 | 1A | 3.55 | 418 |
| 159 | A26-M1-B28 | 1A | 3.37 | 426 |
| 160 | A35-M1-B28 | 1A | 3.4 | 418 |
| 161 | A36-M1-B28 | 1A | 3.15 | 438 |
| 162 | A33-M1-B28 | 1A | 2.94 | 370 |
| 163 | A5-M1-B28 | 1A | 3.1 | 424 |
| 164 | A28-M1-B28 | 1A | 3.16 | 408 |
| 165 | A29-M1-B28 | 1A | 2.44 | 328 |
| 166 | A1-M1-B28 | 1A | 3.03 | 390 |
| 167 | A8-M1-B28 | 1A | 3.19 | 408 |
| 168 | A30-M1-B28 | 1A | 3.46 | 422 |
| 169 | A17-M1-B29 | 1A | 2.12 | 423 |
| 170 | A18-M1-B29 | 1A | 2.44 | 427 |
| 171 | A3-M1-B29 | 1A | 1.69 | 357 |
| 172 | A20-M1-B29 | 1A | 2.01 | 411 |
| 173 | A32-M1-B29 | 1A | 1.63 | 394 |
| 174 | A11-M1-B29 | 1A | 2.03 | 437 |
| 175 | A21-M1-B29 | 1A | 2.07 | 407 |
| 176 | A22-M1-B29 | 1A | 2.1 | 423 |
| 177 | A4-M1-B29 | 1A | 1.98 | 373 |
| 178 | A6-M1-B29 | 1A | 2.23 | 423 |
| 179 | A24-M1-B29 | 1A | 2.62 | 421 |
| 180 | A26-M1-B29 | 1A | 2.32 | 429 |
| 181 | A33-M1-B29 | 1A | 1.91 | 373 |
| 182 | A27-M1-B29 | 1A | 1.75 | 359 |
| 183 | A28-M1-B29 | 1A | 2.13 | 411 |
| 184 | A1-M1-B29 | 1A | 2 | 393 |
| 185 | A8-M1-B29 | 1A | 2.13 | 411 |
| 186 | A17-M1-B8 | 1A | 2.87 | 406 |
| 187 | A18-M1-B8 | 1A | 3.24 | 410 |
| 188 | A3-M1-B8 | 1A | 2.44 | 340 |
| 189 | A19-M1-B8 | 1A | 3.27 | 404 |
| 190 | A20-M1-B8 | 1A | 2.79 | 394 |
| 191 | A32-M1-B8 | 1A | 2.3 | 377 |
| 192 | A11-M1-B8 | 1A | 2.79 | 420 |
| 193 | A21-M1-B8 | 1A | 2.88 | 390 |
| 194 | A22-M1-B8 | 1A | 2.85 | 406 |
| 195 | A4-M1-B8 | 1A | 2.79 | 356 |
| 196 | A6-M1-B8 | 1A | 2.97 | 406 |
| 197 | A24-M1-B8 | 1A | 3.35 | 404 |
| 198 | A25-M1-B8 | 1A | 3.57 | 418 |
| 199 | A26-M1-B8 | 1A | 3.14 | 412 |
| 200 | A35-M1-B8 | 1A | 3.17 | 404 |
| 201 | A36-M1-B8 | 1A | 2.92 | 424 |
| 202 | A33-M1-B8 | 1A | 2.68 | 356 |
| 203 | A34-M1-B8 | 1A | 2.32 | 328 |
| 204 | A27-M1-B8 | 1A | 2.51 | 342 |
| 205 | A28-M1-B8 | 1A | 2.93 | 394 |
| 206 | A8-M1-B8 | 1A | 2.95 | 394 |
| 207 | A30-M1-B8 | 1A | 3.23 | 408 |
| 208 | A17-M1-B10 | 1A | 2.82 | 394 |
| 209 | A31-M1-B10 | 1A | 2.67 | 407 |
| 210 | A18-M1-B10 | 1A | 3.18 | 398 |
| 211 | A3-M1-B10 | 1A | 2.37 | 328 |
| 212 | A19-M1-B10 | 1A | 3.23 | 392 |
| 213 | A20-M1-B10 | 1A | 2.72 | 382 |
| 214 | A32-M1-B10 | 1A | 2.22 | 365 |
| 215 | A11-M1-B10 | 1A | 2.73 | 408 |
| 216 | A22-M1-B10 | 1A | 2.78 | 394 |
| 217 | A6-M1-B10 | 1A | 2.92 | 394 |
| 218 | A24-M1-B10 | 1A | 3.31 | 392 |
| 219 | A25-M1-B10 | 1A | 3.55 | 406 |
| 220 | A26-M1-B10 | 1A | 3.08 | 400 |
| 221 | A35-M1-B10 | 1A | 3.13 | 392 |
| 222 | A36-M1-B10 | 1A | 2.86 | 412 |
| 223 | A33-M1-B10 | 1A | 2.6 | 344 |
| 224 | A5-M1-B10 | 1A | 2.78 | 398 |
| 225 | A27-M1-B10 | 1A | 2.44 | 330 |
| 226 | A28-M1-B10 | 1A | 2.87 | 382 |
| 227 | A1-M1-B10 | 1A | 2.71 | 364 |
| 228 | A8-M1-B10 | 1A | 2.88 | 382 |
| 229 | A30-M1-B10 | 1A | 3.17 | 396 |
| 230 | A17-M1-B17 | 1A | 3.07 | 408 |
| 231 | A31-M1-B17 | 1A | 2.95 | 421 |
| 232 | A18-M1-B17 | 1A | 3.41 | 412 |
| 233 | A3-M1-B17 | 1A | 2.65 | 342 |
| 234 | A19-M1-B17 | 1A | 3.43 | 406 |
| 235 | A20-M1-B17 | 1A | 2.97 | 396 |
| 236 | A32-M1-B17 | 1A | 2.5 | 379 |
| 237 | A11-M1-B17 | 1A | 2.97 | 422 |
| 238 | A21-M1-B17 | 1A | 3.07 | 392 |
| 239 | A4-M1-B17 | 1A | 2.98 | 358 |
| 240 | A6-M1-B17 | 1A | 3.15 | 408 |
| 241 | A24-M1-B17 | 1A | 3.5 | 406 |
| 242 | A25-M1-B17 | 1A | 3.72 | 420 |
| 243 | A26-M1-B17 | 1A | 3.33 | 414 |
| 244 | A36-M1-B17 | 1A | 3.1 | 426 |
| 245 | A33-M1-B17 | 1A | 2.88 | 358 |
| 246 | A5-M1-B17 | 1A | 3.04 | 412 |
| 247 | A27-M1-B17 | 1A | 2.7 | 344 |
| 248 | A28-M1-B17 | 1A | 3.11 | 396 |
| 249 | A1-M1-B17 | 1A | 2.96 | 378 |
| 250 | A8-M1-B17 | 1A | 3.13 | 396 |
| 251 | A30-M1-B17 | 1A | 3.4 | 410 |
| 252 | A17-M1-B30 | 1A | 2.7 | 392 |
| 253 | A31-M1-B30 | 1A | 2.52 | 405 |
| 254 | A19-M1-B30 | 1A | 3.11 | 390 |
| 255 | A20-M1-B30 | 1A | 2.58 | 380 |
| 256 | A32-M1-B30 | 1A | 2.08 | 363 |
| 257 | A21-M1-B30 | 1A | 2.68 | 376 |
| 258 | A22-M1-B30 | 1A | 2.65 | 392 |
| 259 | A4-M1-B30 | 1A | 2.58 | 342 |
| 260 | A24-M1-B30 | 1A | 3.19 | 390 |
| 261 | A25-M1-B30 | 1A | 3.45 | 404 |
| 262 | A26-M1-B30 | 1A | 2.96 | 398 |
| 263 | A35-M1-B30 | 1A | 3.01 | 390 |
| 264 | A36-M1-B30 | 1A | 2.72 | 410 |
| 265 | A33-M1-B30 | 1A | 2.46 | 342 |
| 266 | A5-M1-B30 | 1A | 2.65 | 396 |
| 267 | A28-M1-B30 | 1A | 2.73 | 380 |
| 268 | A1-M1-B30 | 1A | 2.57 | 362 |
| 269 | A8-M1-B30 | 1A | 2.74 | 380 |
| 270 | A30-M1-B30 | 1A | 3.06 | 394 |
| 271 | A17-M1-B3 | 1A | 2.04 | 435 |
| 272 | A31-M1-B3 | 1A | 1.93 | 448 |
| 273 | A18-M1-B3 | 1A | 2.38 | 439 |
| 274 | A3-M1-B3 | 1A | 1.62 | 369 |
| 275 | A37-M1-B3 | 1A | 2.14 | 448 |
| 276 | A19-M1-B3 | 1A | 2.47 | 433 |
| 277 | A20-M1-B3 | 1A | 1.92 | 423 |
| 278 | A32-M1-B3 | 1A | 1.55 | 406 |
| 279 | A11-M1-B3 | 1A | 1.94 | 449 |
| 280 | A21-M1-B3 | 1A | 2.01 | 419 |
| 281 | A22-M1-B3 | 1A | 2 | 435 |
| 282 | A4-M1-B3 | 1A | 1.88 | 385 |
| 283 | A6-M1-B3 | 1A | 2.13 | 435 |
| 284 | A24-M1-B3 | 1A | 2.55 | 433 |
| 285 | A25-M1-B3 | 1A | 2.85 | 447 |
| 286 | A26-M1-B3 | 1A | 2.23 | 441 |
| 287 | A36-M1-B3 | 1A | 2.07 | 453 |
| 288 | A34-M1-B3 | 1A | 1.53 | 357 |
| 289 | A27-M1-B3 | 1A | 1.65 | 371 |
| 290 | A28-M1-B3 | 1A | 2.04 | 423 |
| 291 | A29-M1-B3 | 1A | 1.41 | 343 |
| 292 | A8-M1-B3 | 1A | 2.05 | 423 |
| 293 | A30-M1-B3 | 1A | 2.39 | 437 |
| 294 | A17-M1-B7 | 1A | 2.63 | 422 |
| 295 | A31-M1-B7 | 1A | 2.46 | 435 |
| 296 | A3-M1-B7 | 1A | 2.17 | 356 |
| 297 | A19-M1-B7 | 1A | 3.06 | 420 |
| 298 | A20-M1-B7 | 1A | 2.52 | 410 |
| 299 | A32-M1-B7 | 1A | 2.04 | 393 |
| 300 | A11-M1-B7 | 1A | 2.54 | 436 |
| 301 | A21-M1-B7 | 1A | 2.62 | 406 |
| 302 | A22-M1-B7 | 1A | 2.6 | 422 |
| 303 | A6-M1-B7 | 1A | 2.74 | 422 |
| 304 | A24-M1-B7 | 1A | 3.13 | 420 |
| 305 | A25-M1-B7 | 1A | 3.39 | 434 |
| 306 | A26-M1-B7 | 1A | 2.89 | 428 |
| 307 | A35-M1-B7 | 1A | 2.95 | 420 |
| 308 | A36-M1-B7 | 1A | 2.67 | 440 |

TABLE III-continued

| Entry | Compound | HPLC method | HPLC RT min | [M + H]+ |
|---|---|---|---|---|
| 309 | A33-M1-B7 | 1A | 2.42 | 372 |
| 310 | A5-M1-B7 | 1A | 2.58 | 426 |
| 311 | A34-M1-B7 | 1A | 2.06 | 344 |
| 312 | A27-M1-B7 | 1A | 2.23 | 358 |
| 313 | A28-M1-B7 | 1A | 2.68 | 410 |
| 314 | A29-M1-B7 | 1A | 1.89 | 330 |
| 315 | A8-M1-B7 | 1A | 2.69 | 410 |
| 316 | A30-M1-B7 | 1A | 3 | 424 |
| 317 | A17-M1-B31 | 1A | 2.24 | 463 |
| 318 | A31-M1-B31 | 1A | 2.13 | 476 |
| 319 | A18-M1-B31 | 1A | 2.51 | 467 |
| 320 | A3-M1-B31 | 1A | 1.84 | 397 |
| 321 | A19-M1-B31 | 1A | 2.63 | 461 |
| 322 | A20-M1-B31 | 1A | 2.11 | 451 |
| 323 | A32-M1-B31 | 1A | 1.76 | 434 |
| 324 | A11-M1-B31 | 1A | 2.14 | 477 |
| 325 | A21-M1-B31 | 1A | 2.22 | 447 |
| 326 | A22-M1-B31 | 1A | 2.2 | 463 |
| 327 | A4-M1-B31 | 1A | 2.11 | 413 |
| 328 | A24-M1-B31 | 1A | 2.71 | 461 |
| 329 | A26-M1-B31 | 1A | 2.43 | 469 |
| 330 | A33-M1-B31 | 1A | 2.04 | 413 |
| 331 | A5-M1-B31 | 1A | 2.17 | 467 |
| 332 | A27-M1-B31 | 1A | 1.88 | 399 |
| 333 | A28-M1-B31 | 1A | 2.26 | 451 |
| 334 | A29-M1-B31 | 1A | 1.62 | 371 |
| 335 | A1-M1-B31 | 1A | 2.13 | 433 |
| 336 | A8-M1-B31 | 1A | 2.26 | 451 |
| 337 | A17-M1-B32 | 1A | 2.11 | 463 |
| 338 | A31-M1-B32 | 1A | 2 | 476 |
| 339 | A18-M1-B32 | 1A | 2.41 | 467 |
| 340 | A37-M1-B32 | 1A | 2.21 | 476 |
| 341 | A19-M1-B32 | 1A | 2.52 | 461 |
| 342 | A20-M1-B32 | 1A | 2 | 451 |
| 343 | A32-M1-B32 | 1A | 1.63 | 434 |
| 344 | A11-M1-B32 | 1A | 2.03 | 477 |
| 345 | A21-M1-B32 | 1A | 2.09 | 447 |
| 346 | A4-M1-B32 | 1A | 1.98 | 413 |
| 347 | A6-M1-B32 | 1A | 2.2 | 463 |
| 348 | A24-M1-B32 | 1A | 2.6 | 461 |
| 349 | A25-M1-B32 | 1A | 2.88 | 475 |
| 350 | A26-M1-B32 | 1A | 2.3 | 469 |
| 351 | A35-M1-B32 | 1A | 2.4 | 461 |
| 352 | A36-M1-B32 | 1A | 2.13 | 481 |
| 353 | A33-M1-B32 | 1A | 1.89 | 413 |
| 354 | A5-M1-B32 | 1A | 2.02 | 467 |
| 355 | A27-M1-B32 | 1A | 1.75 | 399 |
| 356 | A28-M1-B32 | 1A | 2.12 | 451 |
| 357 | A1-M1-B32 | 1A | 2 | 433 |
| 358 | A8-M1-B32 | 1A | 2.12 | 451 |
| 359 | A30-M1-B32 | 1A | 2.44 | 465 |
| 360 | A17-M1-B33 | 1A | 2.62 | 410 |
| 361 | A31-M1-B33 | 1A | 2.44 | 423 |
| 362 | A3-M1-B33 | 1A | 2.15 | 344 |
| 363 | A19-M1-B33 | 1A | 3.05 | 408 |
| 364 | A20-M1-B33 | 1A | 2.51 | 398 |
| 365 | A32-M1-B33 | 1A | 2.01 | 381 |
| 366 | A11-M1-B33 | 1A | 2.51 | 424 |
| 367 | A21-M1-B33 | 1A | 2.61 | 394 |
| 368 | A22-M1-B33 | 1A | 2.59 | 410 |
| 369 | A4-M1-B33 | 1A | 2.5 | 360 |
| 370 | A24-M1-B33 | 1A | 3.13 | 408 |
| 371 | A25-M1-B33 | 1A | 3.39 | 422 |
| 372 | A26-M1-B33 | 1A | 2.89 | 416 |
| 373 | A35-M1-B33 | 1A | 2.93 | 408 |
| 374 | A36-M1-B33 | 1A | 2.65 | 428 |
| 375 | A33-M1-B33 | 1A | 2.39 | 360 |
| 376 | A5-M1-B33 | 1A | 2.57 | 414 |
| 377 | A27-M1-B33 | 1A | 2.22 | 346 |
| 378 | A28-M1-B33 | 1A | 2.66 | 398 |
| 379 | A1-M1-B33 | 1A | 2.5 | 380 |
| 380 | A8-M1-B33 | 1A | 2.67 | 398 |
| 381 | A30-M1-B33 | 1A | 3 | 412 |
| 382 | A17-M1-B34 | 1A | 2.16 | 503 |
| 383 | A31-M1-B34 | 1A | 2.05 | 516 |
| 384 | A18-M1-B34 | 1A | 2.48 | 507 |
| 385 | A3-M1-B34 | 1A | 1.77 | 437 |
| 386 | A19-M1-B34 | 1A | 2.57 | 501 |
| 387 | A20-M1-B34 | 1A | 2.05 | 491 |
| 388 | A32-M1-B34 | 1A | 1.7 | 474 |
| 389 | A11-M1-B34 | 1A | 2.08 | 517 |
| 390 | A21-M1-B34 | 1A | 2.14 | 487 |
| 391 | A22-M1-B34 | 1A | 2.14 | 503 |
| 392 | A4-M1-B34 | 1A | 2.04 | 453 |
| 393 | A6-M1-B34 | 1A | 2.26 | 503 |
| 394 | A24-M1-B34 | 1A | 2.63 | 501 |
| 395 | A25-M1-B34 | 1A | 2.9 | 515 |
| 396 | A26-M1-B34 | 1A | 2.36 | 509 |
| 397 | A35-M1-B34 | 1A | 2.44 | 501 |
| 398 | A36-M1-B34 | 1A | 2.19 | 521 |
| 399 | A33-M1-B34 | 1A | 1.95 | 453 |
| 400 | A5-M1-B34 | 1A | 2.11 | 507 |
| 401 | A27-M1-B34 | 1A | 1.81 | 439 |
| 402 | A28-M1-B34 | 1A | 2.18 | 491 |
| 403 | A29-M1-B34 | 1A | 1.57 | 411 |
| 404 | A8-M1-B34 | 1A | 2.15 | 491 |
| 405 | A30-M1-B34 | 1A | 2.49 | 505 |
| 406 | A17-M1-B35 | 1A | 2.29 | 498 |
| 407 | A31-M1-B35 | 1A | 2.18 | 511 |
| 408 | A18-M1-B35 | 1A | 2.6 | 502 |
| 409 | A37-M1-B35 | 1A | 2.38 | 511 |
| 410 | A19-M1-B35 | 1A | 2.65 | 496 |
| 411 | A32-M1-B35 | 1A | 1.83 | 469 |
| 412 | A11-M1-B35 | 1A | 2.19 | 512 |
| 413 | A22-M1-B35 | 1A | 2.25 | 498 |
| 414 | A4-M1-B35 | 1A | 2.17 | 448 |
| 415 | A6-M1-B35 | 1A | 2.38 | 498 |
| 416 | A25-M1-B35 | 1A | 3.01 | 510 |
| 417 | A26-M1-B35 | 1A | 2.48 | 504 |
| 418 | A35-M1-B35 | 1A | 2.55 | 496 |
| 419 | A36-M1-B35 | 1A | 2.32 | 516 |
| 420 | A5-M1-B35 | 1A | 2.24 | 502 |
| 421 | A27-M1-B35 | 1A | 1.94 | 434 |
| 422 | A28-M1-B35 | 1A | 2.31 | 486 |
| 423 | A29-M1-B35 | 1A | 1.69 | 406 |
| 424 | A1-M1-B35 | 1A | 2.18 | 468 |
| 425 | A8-M1-B35 | 1A | 2.31 | 486 |
| 426 | A30-M1-B35 | 1A | 2.63 | 500 |
| 427 | A17-M1-B36 | 1A | 2.76 | 392 |
| 428 | A31-M1-B36 | 1A | 2.6 | 405 |
| 429 | A18-M1-B36 | 1A | 3.13 | 396 |
| 430 | A3-M1-B36 | 1A | 2.29 | 326 |
| 431 | A19-M1-B36 | 1A | 3.17 | 390 |
| 432 | A32-M1-B36 | 1A | 2.15 | 363 |
| 433 | A11-M1-B36 | 1A | 2.66 | 406 |
| 434 | A21-M1-B36 | 1A | 2.77 | 376 |
| 435 | A22-M1-B36 | 1A | 2.73 | 392 |
| 436 | A6-M1-B36 | 1A | 2.85 | 392 |
| 437 | A24-M1-B36 | 1A | 3.26 | 390 |
| 438 | A25-M1-B36 | 1A | 3.5 | 404 |
| 439 | A26-M1-B36 | 1A | 3.03 | 398 |
| 440 | A35-M1-B36 | 1A | 3.08 | 390 |
| 441 | A36-M1-B36 | 1A | 2.8 | 410 |
| 442 | A33-M1-B36 | 1A | 2.54 | 342 |
| 443 | A5-M1-B36 | 1A | 2.72 | 396 |
| 444 | A34-M1-B36 | 1A | 2.17 | 314 |
| 445 | A27-M1-B36 | 1A | 2.35 | 328 |
| 446 | A28-M1-B36 | 1A | 2.81 | 380 |
| 447 | A1-M1-B36 | 1A | 2.64 | 362 |
| 448 | A8-M1-B36 | 1A | 2.81 | 380 |
| 449 | A30-M1-B36 | 1A | 3.13 | 394 |
| 450 | A17-M1-B37 | 1A | 2.05 | 449 |
| 451 | A31-M1-B37 | 1A | 1.94 | 462 |
| 452 | A18-M1-B37 | 1A | 2.35 | 453 |
| 453 | A3-M1-B37 | 1A | 1.64 | 383 |
| 454 | A19-M1-B37 | 1A | 2.43 | 447 |
| 455 | A20-M1-B37 | 1A | 1.93 | 437 |
| 456 | A32-M1-B37 | 1A | 1.57 | 420 |
| 457 | A11-M1-B37 | 1A | 1.96 | 463 |
| 458 | A21-M1-B37 | 1A | 2.02 | 433 |
| 459 | A22-M1-B37 | 1A | 2.04 | 449 |
| 460 | A4-M1-B37 | 1A | 1.9 | 399 |
| 461 | A6-M1-B37 | 1A | 2.14 | 449 |
| 462 | A24-M1-B37 | 1A | 2.56 | 447 |

TABLE III-continued

| Entry | Compound | HPLC method | HPLC RT min | [M + H]+ |
|---|---|---|---|---|
| 463 | A25-M1-B37 | 1A | 2.78 | 461 |
| 464 | A26-M1-B37 | 1A | 2.24 | 455 |
| 465 | A36-M1-B37 | 1A | 2.05 | 467 |
| 466 | A33-M1-B37 | 1A | 1.84 | 399 |
| 467 | A5-M1-B37 | 1A | 1.98 | 453 |
| 468 | A27-M1-B37 | 1A | 1.68 | 385 |
| 469 | A28-M1-B37 | 1A | 2.05 | 437 |
| 470 | A29-M1-B37 | 1A | 1.45 | 357 |
| 471 | A8-M1-B37 | 1A | 2.05 | 437 |
| 472 | A30-M1-B37 | 1A | 2.37 | 451 |
| 473 | A17-M1-B38 | 1A | 2.97 | 438 |
| 474 | A31-M1-B38 | 1A | 2.85 | 451 |
| 475 | A3-M1-B38 | 1A | 2.56 | 372 |
| 476 | A19-M1-B38 | 1A | 3.37 | 436 |
| 477 | A20-M1-B38 | 1A | 2.88 | 426 |
| 478 | A32-M1-B38 | 1A | 2.4 | 409 |
| 479 | A11-M1-B38 | 1A | 2.88 | 452 |
| 480 | A21-M1-B38 | 1A | 2.98 | 422 |
| 481 | A22-M1-B38 | 1A | 2.95 | 438 |
| 482 | A4-M1-B38 | 1A | 2.9 | 388 |
| 483 | A6-M1-B38 | 1A | 3.07 | 438 |
| 484 | A24-M1-B38 | 1A | 3.44 | 436 |
| 485 | A25-M1-B38 | 1A | 3.66 | 450 |
| 486 | A26-M1-B38 | 1A | 3.24 | 444 |
| 487 | A35-M1-B38 | 1A | 3.27 | 436 |
| 488 | A36-M1-B38 | 1A | 3.02 | 456 |
| 489 | A5-M1-B38 | 1A | 2.95 | 442 |
| 490 | A27-M1-B38 | 1A | 2.62 | 374 |
| 491 | A28-M1-B38 | 1A | 3.03 | 426 |
| 492 | A1-M1-B38 | 1A | 2.88 | 408 |
| 493 | A8-M1-B38 | 1A | 3.05 | 426 |
| 494 | A30-M1-B38 | 1A | 3.33 | 440 |
| 495 | A17-M1-B39 | 1A | 3.09 | 408 |
| 496 | A31-M1-B39 | 1A | 2.99 | 421 |
| 497 | A3-M1-B39 | 1A | 2.7 | 342 |
| 498 | A19-M1-B39 | 1A | 3.46 | 406 |
| 499 | A20-M1-B39 | 1A | 3 | 396 |
| 500 | A32-M1-B39 | 1A | 2.53 | 379 |
| 501 | A11-M1-B39 | 1A | 3.01 | 422 |
| 502 | A21-M1-B39 | 1A | 3.11 | 392 |
| 503 | A22-M1-B39 | 1A | 3.06 | 408 |
| 504 | A4-M1-B39 | 1A | 3.04 | 358 |
| 505 | A6-M1-B39 | 1A | 3.19 | 408 |
| 506 | A24-M1-B39 | 1A | 3.54 | 406 |
| 507 | A25-M1-B39 | 1A | 3.75 | 420 |
| 508 | A26-M1-B39 | 1A | 3.36 | 414 |
| 509 | A35-M1-B39 | 1A | 3.38 | 406 |
| 510 | A36-M1-B39 | 1A | 3.13 | 426 |
| 511 | A33-M1-B39 | 1A | 2.92 | 358 |
| 512 | A5-M1-B39 | 1A | 3.07 | 412 |
| 513 | A34-M1-B39 | 1A | 2.57 | 330 |
| 514 | A27-M1-B39 | 1A | 2.75 | 344 |
| 515 | A28-M1-B39 | 1A | 3.15 | 396 |
| 516 | A1-M1-B39 | 1A | 3 | 378 |
| 517 | A8-M1-B39 | 1A | 3.16 | 396 |
| 518 | A30-M1-B39 | 1A | 3.43 | 410 |
| 519 | A17-M1-B40 | 1A | 2.09 | 463 |
| 520 | A31-M1-B40 | 1A | 1.97 | 476 |
| 521 | A3-M1-B40 | 1A | 1.68 | 397 |
| 522 | A19-M1-B40 | 1A | 2.49 | 461 |
| 523 | A20-M1-B40 | 1A | 1.96 | 451 |
| 524 | A32-M1-B40 | 1A | 1.62 | 434 |
| 525 | A11-M1-B40 | 1A | 2 | 477 |
| 526 | A21-M1-B40 | 1A | 2.07 | 447 |
| 527 | A22-M1-B40 | 1A | 2.07 | 463 |
| 528 | A4-M1-B40 | 1A | 1.94 | 413 |
| 529 | A6-M1-B40 | 1A | 2.18 | 463 |
| 530 | A24-M1-B40 | 1A | 2.57 | 461 |
| 531 | A25-M1-B40 | 1A | 2.85 | 475 |
| 532 | A26-M1-B40 | 1A | 2.29 | 469 |
| 533 | A35-M1-B40 | 1A | 2.37 | 461 |
| 534 | A36-M1-B40 | 1A | 2.12 | 481 |
| 535 | A33-M1-B40 | 1A | 1.87 | 413 |
| 536 | A5-M1-B40 | 1A | 2.02 | 467 |
| 537 | A34-M1-B40 | 1A | 1.6 | 385 |
| 538 | A27-M1-B40 | 1A | 1.73 | 399 |
| 539 | A28-M1-B40 | 1A | 2.1 | 451 |
| 540 | A29-M1-B40 | 1A | 1.49 | 371 |
| 541 | A1-M1-B40 | 1A | 1.97 | 433 |
| 542 | A8-M1-B40 | 1A | 2.11 | 451 |
| 543 | A30-M1-B40 | 1A | 2.42 | 465 |
| 544 | A17-M1-B41 | 1A | 2.92 | 406 |
| 545 | A31-M1-B41 | 1A | 2.78 | 419 |
| 546 | A18-M1-B41 | 1A | 3.28 | 410 |
| 547 | A3-M1-B41 | 1A | 2.49 | 340 |
| 548 | A19-M1-B41 | 1A | 3.31 | 404 |
| 549 | A20-M1-B41 | 1A | 2.83 | 394 |
| 550 | A32-M1-B41 | 1A | 2.33 | 377 |
| 551 | A11-M1-B41 | 1A | 2.82 | 420 |
| 552 | A21-M1-B41 | 1A | 2.93 | 390 |
| 553 | A22-M1-B41 | 1A | 2.88 | 406 |
| 554 | A4-M1-B41 | 1A | 2.85 | 356 |
| 555 | A6-M1-B41 | 1A | 3.02 | 406 |
| 556 | A24-M1-B41 | 1A | 3.39 | 404 |
| 557 | A25-M1-B41 | 1A | 3.61 | 418 |
| 558 | A26-M1-B41 | 1A | 3.19 | 412 |
| 559 | A35-M1-B41 | 1A | 3.22 | 404 |
| 560 | A33-M1-B41 | 1A | 2.72 | 356 |
| 561 | A5-M1-B41 | 1A | 2.89 | 410 |
| 562 | A27-M1-B41 | 1A | 2.56 | 342 |
| 563 | A28-M1-B41 | 1A | 2.98 | 394 |
| 564 | A1-M1-B41 | 1A | 2.82 | 376 |
| 565 | A30-M1-B41 | 1A | 3.27 | 408 |
| 566 | A17-M1-B42 | 1A | 3.14 | 420 |
| 567 | A18-M1-B42 | 1A | 3.5 | 424 |
| 568 | A19-M1-B42 | 1A | 3.51 | 418 |
| 569 | A32-M1-B42 | 1A | 2.6 | 391 |
| 570 | A11-M1-B42 | 1A | 3.06 | 434 |
| 571 | A22-M1-B42 | 1A | 3.11 | 420 |
| 572 | A4-M1-B42 | 1A | 3.09 | 370 |
| 573 | A24-M1-B42 | 1A | 3.58 | 418 |
| 574 | A25-M1-B42 | 1A | 3.79 | 432 |
| 575 | A26-M1-B42 | 1A | 3.41 | 426 |
| 576 | A35-M1-B42 | 1A | 3.43 | 418 |
| 577 | A36-M1-B42 | 1A | 3.18 | 438 |
| 578 | A5-M1-B42 | 1A | 3.12 | 424 |
| 579 | A34-M1-B42 | 1A | 2.63 | 342 |
| 580 | A27-M1-B42 | 1A | 2.81 | 356 |
| 581 | A28-M1-B42 | 1A | 3.21 | 408 |
| 582 | A1-M1-B42 | 1A | 3.06 | 390 |
| 583 | A8-M1-B42 | 1A | 3.22 | 408 |
| 584 | A30-M1-B42 | 1A | 3.48 | 422 |
| 585 | A17-M1-B6 | 1A | 2.66 | 380 |
| 586 | A31-M1-B6 | 1A | 2.49 | 393 |
| 587 | A18-M1-B6 | 1A | 3.04 | 384 |
| 588 | A3-M1-B6 | 1A | 2.19 | 314 |
| 589 | A19-M1-B6 | 1A | 3.09 | 378 |
| 590 | A20-M1-B6 | 1A | 2.55 | 368 |
| 591 | A32-M1-B6 | 1A | 2.04 | 351 |
| 592 | A11-M1-B6 | 1A | 2.55 | 394 |
| 593 | A6-M1-B6 | 1A | 2.76 | 380 |
| 594 | A24-M1-B6 | 1A | 3.17 | 378 |
| 595 | A25-M1-B6 | 1A | 3.43 | 392 |
| 596 | A26-M1-B6 | 1A | 2.92 | 386 |
| 597 | A35-M1-B6 | 1A | 2.98 | 378 |
| 598 | A36-M1-B6 | 1A | 2.69 | 398 |
| 599 | A33-M1-B6 | 1A | 2.42 | 330 |
| 600 | A5-M1-B6 | 1A | 2.62 | 384 |
| 601 | A28-M1-B6 | 1A | 2.7 | 368 |
| 602 | A8-M1-B6 | 1A | 2.71 | 368 |
| 603 | A30-M1-B6 | 1A | 3.04 | 382 |
| 604 | A17-M1-B43 | 1A | 2.16 | 449 |
| 605 | A18-M1-B43 | 1A | 2.47 | 453 |
| 606 | A19-M1-B43 | 1A | 2.58 | 447 |
| 607 | A32-M1-B43 | 1A | 1.68 | 420 |
| 608 | A11-M1-B43 | 1A | 2.05 | 463 |
| 609 | A21-M1-B43 | 1A | 2.13 | 433 |
| 610 | A22-M1-B43 | 1A | 2.14 | 449 |
| 611 | A6-M1-B43 | 1A | 2.26 | 449 |
| 612 | A24-M1-B43 | 1A | 2.65 | 447 |
| 613 | A26-M1-B43 | 1A | 2.35 | 455 |
| 614 | A33-M1-B43 | 1A | 1.94 | 399 |
| 615 | A5-M1-B43 | 1A | 2.1 | 453 |
| 616 | A28-M1-B43 | 1A | 2.18 | 437 |

TABLE III-continued

| Entry | Compound | HPLC method | HPLC RT min | [M + H]+ |
|---|---|---|---|---|
| 617 | A1-M1-B43 | 1A | 2.05 | 419 |
| 618 | A8-M1-B43 | 1A | 2.17 | 437 |
| 619 | A38-M1-B41 | 3 | 4.82 | 444 |
| 620 | A39-M1-B8 | 3 | 5.21 | 418 |
| 621 | A39-M1-B34 | 3 | 4.52 | 515 |
| 622 | A14-M2-B11 | 2 | 6.05 | 462 |
| 623 | A15-M2-B11 | 2 | 5.97 | 476 |
| 624 | A8-M2-B11 | 2 | 6 | 466 |
| 625 | A9-M2-B11 | 2 | 5.27 | 438 |
| 626 | A14-M2-B12 | 2 | 5.03 | 454 |
| 627 | A15-M2-B12 | 2 | 4.93 | 468 |
| 628 | A9-M2-B12 | 2 | 4.27 | 430 |
| 629 | A16-M2-B12 | 2 | 3.45 | 538 |
| 630 | A9-M2-B13 | 2 | 4.67 | 464 |
| 631 | A14-M2-B15 | 2 | 4.9 | 470 |
| 632 | A8-M2-B15 | 2 | 4.77 | 474 |
| 633 | A9-M2-B15 | 2 | 4.18 | 446 |
| 634 | A16-M2-B15 | 2 | 3.4 | 554 |
| 635 | A14-M2-B19 | 2 | 3.93 | 378 |
| 636 | A8-M2-B19 | 2 | 3.87 | 382 |
| 637 | A9-M2-B19 | 2 | 3.08 | 354 |
| 638 | A16-M2-B19 | 2 | 2.53 | 462 |
| 639 | A26-M2-B43 | 1A | 2.43 | 469 |
| 640 | A17-M2-B24 | 1A | 2.145 | 463 |
| 641 | A19-M2-B24 | 1A | 2.55 | 461 |
| 642 | A32-M2-B24 | 1A | 1.635 | 434 |
| 643 | A11-M2-B24 | 1A | 2.045 | 477 |
| 644 | A4-M2-B24 | 1A | 1.99 | 413 |
| 645 | A6-M2-B24 | 1A | 2.25 | 463 |
| 646 | A24-M2-B24 | 1A | 2.615 | 461 |
| 647 | A25-M2-B24 | 1A | 2.91 | 475 |
| 648 | A28-M2-B24 | 1A | 2.18 | 451 |
| 649 | A29-M2-B24 | 1A | 1.505 | 371 |
| 650 | A8-M2-B24 | 1A | 2.18 | 451 |
| 651 | A30-M2-B24 | 1A | 2.495 | 465 |
| 652 | A17-M2-B25 | 1A | 2.24 | 457 |
| 653 | A18-M2-B25 | 1A | 2.59 | 461 |
| 654 | A3-M2-B25 | 1A | 1.82 | 391 |
| 655 | A19-M2-B25 | 1A | 2.67 | 455 |
| 656 | A20-M2-B25 | 1A | 2.14 | 445 |
| 657 | A32-M2-B25 | 1A | 1.725 | 428 |
| 658 | A21-M2-B25 | 1A | 2.21 | 441 |
| 659 | A4-M2-B25 | 1A | 2.11 | 407 |
| 660 | A6-M2-B25 | 1A | 2.34 | 457 |
| 661 | A26-M2-B25 | 1A | 2.48 | 463 |
| 662 | A33-M2-B25 | 1A | 2.04 | 407 |
| 663 | A34-M2-B25 | 1A | 1.715 | 379 |
| 664 | A28-M2-B25 | 1A | 2.265 | 445 |
| 665 | A1-M2-B25 | 1A | 2.13 | 427 |
| 666 | A8-M2-B25 | 1A | 2.27 | 445 |
| 667 | A17-M2-B26 | 1A | 2.4 | 457 |
| 668 | A31-M2-B26 | 1A | 2.285 | 470 |
| 669 | A18-M2-B26 | 1A | 2.76 | 461 |
| 670 | A3-M2-B26 | 1A | 1.95 | 391 |
| 671 | A19-M2-B26 | 1A | 2.84 | 455 |
| 672 | A20-M2-B26 | 1A | 2.31 | 445 |
| 673 | A32-M2-B26 | 1A | 1.855 | 428 |
| 674 | A11-M2-B26 | 1A | 2.31 | 471 |
| 675 | A21-M2-B26 | 1A | 2.39 | 441 |
| 676 | A6-M2-B26 | 1A | 2.51 | 457 |
| 677 | A24-M2-B26 | 1A | 2.905 | 455 |
| 678 | A26-M2-B26 | 1A | 2.645 | 463 |
| 679 | A33-M2-B26 | 1A | 2.18 | 407 |
| 680 | A5-M2-B26 | 1A | 2.36 | 461 |
| 681 | A28-M2-B26 | 1A | 2.44 | 445 |
| 682 | A1-M2-B26 | 1A | 2.285 | 427 |
| 683 | A8-M2-B26 | 1A | 2.445 | 445 |
| 684 | A17-M2-B27 | 1A | 3.09 | 422 |
| 685 | A31-M2-B27 | 1A | 2.96 | 435 |
| 686 | A18-M2-B27 | 1A | 3.42 | 426 |
| 687 | A19-M2-B27 | 1A | 3.45 | 420 |
| 688 | A20-M2-B27 | 1A | 3.02 | 410 |
| 689 | A32-M2-B27 | 1A | 2.51 | 393 |
| 690 | A11-M2-B27 | 1A | 2.99 | 436 |
| 691 | A22-M2-B27 | 1A | 3.05 | 422 |
| 692 | A6-M2-B27 | 1A | 3.17 | 422 |
| 693 | A24-M2-B27 | 1A | 3.53 | 420 |
| 694 | A25-M2-B27 | 1A | 3.75 | 434 |
| 695 | A26-M2-B27 | 1A | 3.35 | 428 |
| 696 | A35-M2-B27 | 1A | 3.37 | 420 |
| 697 | A36-M2-B27 | 1A | 3.11 | 440 |
| 698 | A5-M2-B27 | 1A | 3.08 | 426 |
| 699 | A27-M2-B27 | 1A | 2.73 | 358 |
| 700 | A28-M2-B27 | 1A | 3.14 | 410 |
| 701 | A1-M2-B27 | 1A | 2.99 | 392 |
| 702 | A8-M2-B27 | 1A | 3.15 | 410 |
| 703 | A30-M2-B27 | 1A | 3.41 | 424 |
| 704 | A17-M2-B28 | 1A | 3.18 | 434 |
| 705 | A31-M2-B28 | 1A | 3.085 | 447 |
| 706 | A18-M2-B28 | 1A | 3.52 | 438 |
| 707 | A19-M2-B28 | 1A | 3.54 | 432 |
| 708 | A20-M2-B28 | 1A | 3.13 | 422 |
| 709 | A32-M2-B28 | 1A | 2.63 | 405 |
| 710 | A11-M2-B28 | 1A | 3.1 | 448 |
| 711 | A21-M2-B28 | 1A | 3.19 | 418 |
| 712 | A22-M2-B28 | 1A | 3.14 | 434 |
| 713 | A24-M2-B28 | 1A | 3.61 | 432 |
| 714 | A25-M2-B28 | 1A | 3.82 | 446 |
| 715 | A26-M2-B28 | 1A | 3.44 | 440 |
| 716 | A35-M2-B28 | 1A | 3.46 | 432 |
| 717 | A33-M2-B28 | 1A | 3.04 | 384 |
| 718 | A5-M2-B28 | 1A | 3.18 | 438 |
| 719 | A28-M2-B28 | 1A | 3.245 | 422 |
| 720 | A1-M2-B28 | 1A | 3.09 | 404 |
| 721 | A8-M2-B28 | 1A | 3.25 | 422 |
| 722 | A30-M2-B28 | 1A | 3.51 | 436 |
| 723 | A17-M2-B29 | 1A | 2.18 | 437 |
| 724 | A3-M2-B29 | 1A | 1.76 | 371 |
| 725 | A19-M2-B29 | 1A | 2.59 | 435 |
| 726 | A32-M2-B29 | 1A | 1.675 | 408 |
| 727 | A11-M2-B29 | 1A | 2.09 | 451 |
| 728 | A26-M2-B29 | 1A | 2.4 | 443 |
| 729 | A28-M2-B29 | 1A | 2.21 | 425 |
| 730 | A8-M2-B29 | 1A | 2.205 | 425 |
| 731 | A17-M2-B8 | 1A | 2.95 | 420 |
| 732 | A31-M2-B8 | 1A | 2.815 | 433 |
| 733 | A3-M2-B8 | 1A | 2.52 | 354 |
| 734 | A19-M2-B8 | 1A | 3.33 | 418 |
| 735 | A20-M2-B8 | 1A | 2.88 | 408 |
| 736 | A32-M2-B8 | 1A | 2.37 | 391 |
| 737 | A11-M2-B8 | 1A | 2.86 | 434 |
| 738 | A21-M2-B8 | 1A | 2.95 | 404 |
| 739 | A22-M2-B8 | 1A | 2.91 | 420 |
| 740 | A4-M2-B8 | 1A | 2.86 | 370 |
| 741 | A24-M2-B8 | 1A | 3.4 | 418 |
| 742 | A25-M2-B8 | 1A | 3.63 | 432 |
| 743 | A26-M2-B8 | 1A | 3.22 | 426 |
| 744 | A35-M2-B8 | 1A | 3.24 | 418 |
| 745 | A36-M2-B8 | 1A | 2.98 | 438 |
| 746 | A33-M2-B8 | 1A | 2.78 | 370 |
| 747 | A5-M2-B8 | 1A | 2.94 | 424 |
| 748 | A27-M2-B8 | 1A | 2.58 | 356 |
| 749 | A28-M2-B8 | 1A | 3.01 | 408 |
| 750 | A1-M2-B8 | 1A | 2.85 | 390 |
| 751 | A8-M2-B8 | 1A | 3.02 | 408 |
| 752 | A30-M2-B8 | 1A | 3.295 | 422 |
| 753 | A17-M2-B10 | 1A | 2.895 | 408 |
| 754 | A31-M2-B10 | 1A | 2.74 | 421 |
| 755 | A18-M2-B10 | 1A | 3.27 | 412 |
| 756 | A19-M2-B10 | 1A | 3.3 | 406 |
| 757 | A20-M2-B10 | 1A | 2.82 | 396 |
| 758 | A32-M2-B10 | 1A | 2.28 | 379 |
| 759 | A11-M2-B10 | 1A | 2.8 | 422 |
| 760 | A24-M2-B10 | 1A | 3.37 | 406 |
| 761 | A26-M2-B10 | 1A | 3.17 | 414 |
| 762 | A35-M2-B10 | 1A | 3.2 | 406 |
| 763 | A33-M2-B10 | 1A | 2.72 | 358 |
| 764 | A5-M2-B10 | 1A | 2.88 | 412 |
| 765 | A28-M2-B10 | 1A | 2.95 | 396 |
| 766 | A8-M2-B10 | 1A | 2.96 | 396 |
| 767 | A30-M2-B10 | 1A | 3.26 | 410 |
| 768 | A17-M2-B17 | 1A | 3.1 | 422 |
| 769 | A31-M2-B17 | 1A | 2.99 | 435 |
| 770 | A18-M2-B17 | 1A | 3.455 | 426 |

TABLE III-continued

| Entry | Compound | HPLC method | HPLC RT min | [M + H]+ |
|---|---|---|---|---|
| 771 | A3-M2-B17 | 1A | 2.71 | 356 |
| 772 | A32-M2-B17 | 1A | 2.55 | 393 |
| 773 | A11-M2-B17 | 1A | 3.03 | 436 |
| 774 | A21-M2-B17 | 1A | 3.12 | 406 |
| 775 | A22-M2-B17 | 1A | 3.07 | 422 |
| 776 | A4-M2-B17 | 1A | 3.055 | 372 |
| 777 | A6-M2-B17 | 1A | 3.195 | 422 |
| 778 | A24-M2-B17 | 1A | 3.54 | 420 |
| 779 | A26-M2-B17 | 1A | 3.37 | 428 |
| 780 | A35-M2-B17 | 1A | 3.38 | 420 |
| 781 | A36-M2-B17 | 1A | 3.13 | 440 |
| 782 | A5-M2-B17 | 1A | 3.1 | 426 |
| 783 | A27-M2-B17 | 1A | 2.76 | 358 |
| 784 | A28-M2-B17 | 1A | 3.17 | 410 |
| 785 | A8-M2-B17 | 1A | 3.18 | 410 |
| 786 | A30-M2-B17 | 1A | 3.45 | 424 |
| 787 | A17-M2-B30 | 1A | 2.79 | 406 |
| 788 | A31-M2-B30 | 1A | 2.61 | 419 |
| 789 | A18-M2-B30 | 1A | 3.16 | 410 |
| 790 | A19-M2-B30 | 1A | 3.2 | 404 |
| 791 | A32-M2-B30 | 1A | 2.15 | 377 |
| 792 | A11-M2-B30 | 1A | 2.67 | 420 |
| 793 | A4-M2-B30 | 1A | 2.67 | 356 |
| 794 | A6-M2-B30 | 1A | 2.86 | 406 |
| 795 | A24-M2-B30 | 1A | 3.27 | 404 |
| 796 | A25-M2-B30 | 1A | 3.53 | 418 |
| 797 | A26-M2-B30 | 1A | 3.05 | 412 |
| 798 | A35-M2-B30 | 1A | 3.09 | 404 |
| 799 | A33-M2-B30 | 1A | 2.58 | 356 |
| 800 | A27-M2-B30 | 1A | 2.37 | 342 |
| 801 | A28-M2-B30 | 1A | 2.84 | 394 |
| 802 | A30-M2-B30 | 1A | 3.135 | 408 |
| 803 | A17-M2-B3 | 1A | 2.12 | 449 |
| 804 | A31-M2-B3 | 1A | 1.99 | 462 |
| 805 | A18-M2-B3 | 1A | 2.42 | 453 |
| 806 | A3-M2-B3 | 1A | 1.69 | 383 |
| 807 | A37-M2-B3 | 1A | 2.24 | 462 |
| 808 | A19-M2-B3 | 1A | 2.52 | 447 |
| 809 | A32-M2-B3 | 1A | 1.61 | 420 |
| 810 | A11-M2-B3 | 1A | 2.03 | 463 |
| 811 | A21-M2-B3 | 1A | 2.075 | 433 |
| 812 | A24-M2-B3 | 1A | 2.61 | 447 |
| 813 | A25-M2-B3 | 1A | 2.87 | 461 |
| 814 | A26-M2-B3 | 1A | 2.315 | 455 |
| 815 | A33-M2-B3 | 1A | 1.92 | 399 |
| 816 | A5-M2-B3 | 1A | 2.05 | 453 |
| 817 | A34-M2-B3 | 1A | 1.59 | 371 |
| 818 | A27-M2-B3 | 1A | 1.715 | 385 |
| 819 | A28-M2-B3 | 1A | 2.13 | 437 |
| 820 | A29-M2-B3 | 1A | 1.47 | 357 |
| 821 | A1-M2-B3 | 1A | 2.01 | 419 |
| 822 | A8-M2-B3 | 1A | 2.125 | 437 |
| 823 | A17-M2-B7 | 1A | 2.715 | 436 |
| 824 | A31-M2-B7 | 1A | 2.54 | 449 |
| 825 | A18-M2-B7 | 1A | 3.08 | 440 |
| 826 | A19-M2-B7 | 1A | 3.125 | 434 |
| 827 | A11-M2-B7 | 1A | 2.61 | 450 |
| 828 | A21-M2-B7 | 1A | 2.7 | 420 |
| 829 | A24-M2-B7 | 1A | 3.21 | 434 |
| 830 | A25-M2-B7 | 1A | 3.46 | 448 |
| 831 | A26-M2-B7 | 1A | 2.99 | 442 |
| 832 | A35-M2-B7 | 1A | 3.02 | 434 |
| 833 | A36-M2-B7 | 1A | 2.74 | 454 |
| 834 | A33-M2-B7 | 1A | 2.51 | 386 |
| 835 | A5-M2-B7 | 1A | 2.67 | 440 |
| 836 | A34-M2-B7 | 1A | 2.13 | 358 |
| 837 | A27-M2-B7 | 1A | 2.31 | 372 |
| 838 | A28-M2-B7 | 1A | 2.77 | 424 |
| 839 | A29-M2-B7 | 1A | 1.97 | 344 |
| 840 | A8-M2-B7 | 1A | 2.78 | 424 |
| 841 | A30-M2-B7 | 1A | 3.09 | 438 |
| 842 | A17-M2-B31 | 1A | 2.32 | 477 |
| 843 | A31-M2-B31 | 1A | 2.19 | 490 |
| 844 | A18-M2-B31 | 1A | 2.59 | 481 |
| 845 | A3-M2-B31 | 1A | 1.89 | 411 |
| 846 | A19-M2-B31 | 1A | 2.67 | 475 |
| 847 | A20-M2-B31 | 1A | 2.21 | 465 |
| 848 | A32-M2-B31 | 1A | 1.815 | 448 |
| 849 | A11-M2-B31 | 1A | 2.22 | 491 |
| 850 | A4-M2-B31 | 1A | 2.17 | 427 |
| 851 | A6-M2-B31 | 1A | 2.385 | 477 |
| 852 | A23-M2-B31 | 1A | 1.75 | 415 |
| 853 | A24-M2-B31 | 1A | 2.77 | 475 |
| 854 | A26-M2-B31 | 1A | 2.53 | 483 |
| 855 | A5-M2-B31 | 1A | 2.24 | 481 |
| 856 | A34-M2-B31 | 1A | 1.795 | 399 |
| 857 | A28-M2-B31 | 1A | 2.335 | 465 |
| 858 | A8-M2-B31 | 1A | 2.34 | 465 |
| 859 | A17-M2-B32 | 1A | 2.18 | 477 |
| 860 | A31-M2-B32 | 1A | 2.05 | 490 |
| 861 | A18-M2-B32 | 1A | 2.49 | 481 |
| 862 | A3-M2-B32 | 1A | 1.76 | 411 |
| 863 | A37-M2-B32 | 1A | 2.27 | 490 |
| 864 | A19-M2-B32 | 1A | 2.575 | 475 |
| 865 | A32-M2-B32 | 1A | 1.685 | 448 |
| 866 | A11-M2-B32 | 1A | 2.08 | 491 |
| 867 | A21-M2-B32 | 1A | 2.16 | 461 |
| 868 | A4-M2-B32 | 1A | 2.04 | 427 |
| 869 | A6-M2-B32 | 1A | 2.27 | 477 |
| 870 | A23-M2-B32 | 1A | 1.63 | 415 |
| 871 | A24-M2-B32 | 1A | 2.64 | 475 |
| 872 | A25-M2-B32 | 1A | 2.905 | 489 |
| 873 | A26-M2-B32 | 1A | 2.39 | 483 |
| 874 | A35-M2-B32 | 1A | 2.44 | 475 |
| 875 | A36-M2-B32 | 1A | 2.21 | 495 |
| 876 | A5-M2-B32 | 1A | 2.13 | 481 |
| 877 | A28-M2-B32 | 1A | 2.19 | 465 |
| 878 | A1-M2-B32 | 1A | 2.06 | 447 |
| 879 | A8-M2-B32 | 1A | 2.2 | 465 |
| 880 | A17-M2-B33 | 1A | 2.705 | 424 |
| 881 | A31-M2-B33 | 1A | 2.54 | 437 |
| 882 | A3-M2-B33 | 1A | 2.24 | 358 |
| 883 | A19-M2-B33 | 1A | 3.13 | 422 |
| 884 | A20-M2-B33 | 1A | 2.62 | 412 |
| 885 | A32-M2-B33 | 1A | 2.085 | 395 |
| 886 | A11-M2-B33 | 1A | 2.61 | 438 |
| 887 | A21-M2-B33 | 1A | 2.705 | 408 |
| 888 | A22-M2-B33 | 1A | 2.66 | 424 |
| 889 | A4-M2-B33 | 1A | 2.59 | 374 |
| 890 | A6-M2-B33 | 1A | 2.795 | 424 |
| 891 | A24-M2-B33 | 1A | 3.215 | 422 |
| 892 | A25-M2-B33 | 1A | 3.47 | 436 |
| 893 | A26-M2-B33 | 1A | 2.99 | 430 |
| 894 | A35-M2-B33 | 1A | 3.03 | 422 |
| 895 | A36-M2-B33 | 1A | 2.73 | 442 |
| 896 | A33-M2-B33 | 1A | 2.51 | 374 |
| 897 | A5-M2-B33 | 1A | 2.67 | 428 |
| 898 | A27-M2-B33 | 1A | 2.3 | 360 |
| 899 | A1-M2-B33 | 1A | 2.59 | 394 |
| 900 | A8-M2-B33 | 1A | 2.78 | 412 |
| 901 | A30-M2-B33 | 1A | 3.085 | 426 |
| 902 | A17-M2-B34 | 1A | 2.25 | 517 |
| 903 | A31-M2-B34 | 1A | 2.11 | 530 |
| 904 | A18-M2-B34 | 1A | 2.535 | 521 |
| 905 | A3-M2-B34 | 1A | 1.83 | 451 |
| 906 | A19-M2-B34 | 1A | 2.63 | 515 |
| 907 | A20-M2-B34 | 1A | 2.15 | 505 |
| 908 | A32-M2-B34 | 1A | 1.745 | 488 |
| 909 | A11-M2-B34 | 1A | 2.13 | 531 |
| 910 | A21-M2-B34 | 1A | 2.195 | 501 |
| 911 | A22-M2-B34 | 1A | 2.2 | 517 |
| 912 | A4-M2-B34 | 1A | 2.085 | 467 |
| 913 | A6-M2-B34 | 1A | 2.33 | 517 |
| 914 | A24-M2-B34 | 1A | 2.685 | 515 |
| 915 | A26-M2-B34 | 1A | 2.43 | 523 |
| 916 | A35-M2-B34 | 1A | 2.5 | 515 |
| 917 | A36-M2-B34 | 1A | 2.255 | 535 |
| 918 | A33-M2-B34 | 1A | 2.055 | 467 |
| 919 | A27-M2-B34 | 1A | 1.855 | 453 |
| 920 | A28-M2-B34 | 1A | 2.255 | 505 |
| 921 | A1-M2-B34 | 1A | 2.115 | 487 |
| 922 | A8-M2-B34 | 1A | 2.265 | 505 |
| 923 | A30-M2-B34 | 1A | 2.555 | 519 |
| 924 | A17-M2-B35 | 1A | 2.36 | 512 |

TABLE III-continued

| Entry | Compound | HPLC method | HPLC RT min | [M + H]+ |
|---|---|---|---|---|
| 925 | A31-M2-B35 | 1A | 2.25 | 525 |
| 926 | A18-M2-B35 | 1A | 2.68 | 516 |
| 927 | A3-M2-B35 | 1A | 1.95 | 446 |
| 928 | A37-M2-B35 | 1A | 2.44 | 525 |
| 929 | A19-M2-B35 | 1A | 2.73 | 510 |
| 930 | A20-M2-B35 | 1A | 2.27 | 500 |
| 931 | A32-M2-B35 | 1A | 1.875 | 483 |
| 932 | A11-M2-B35 | 1A | 2.27 | 526 |
| 933 | A4-M2-B35 | 1A | 2.235 | 462 |
| 934 | A6-M2-B35 | 1A | 2.435 | 512 |
| 935 | A24-M2-B35 | 1A | 2.81 | 510 |
| 936 | A26-M2-B35 | 1A | 2.57 | 518 |
| 937 | A35-M2-B35 | 1A | 2.63 | 510 |
| 938 | A36-M2-B35 | 1A | 2.395 | 530 |
| 939 | A28-M2-B35 | 1A | 2.39 | 500 |
| 940 | A1-M2-B35 | 1A | 2.265 | 482 |
| 941 | A8-M2-B35 | 1A | 2.39 | 500 |
| 942 | A30-M2-B35 | 1A | 2.69 | 514 |
| 943 | A17-M2-B36 | 1A | 2.83 | 406 |
| 944 | A31-M2-B36 | 1A | 2.67 | 419 |
| 945 | A18-M2-B36 | 1A | 3.205 | 410 |
| 946 | A27-M2-B43 | 1A | 1.87 | 399 |
| 947 | A19-M2-B36 | 1A | 3.245 | 404 |
| 948 | A20-M2-B36 | 1A | 2.755 | 394 |
| 949 | A32-M2-B36 | 1A | 2.215 | 377 |
| 950 | A22-M2-B36 | 1A | 2.8 | 406 |
| 951 | A4-M2-B36 | 1A | 2.74 | 356 |
| 952 | A6-M2-B36 | 1A | 2.925 | 406 |
| 953 | A28-M2-B43 | 1A | 2.27 | 451 |
| 954 | A24-M2-B36 | 1A | 3.33 | 404 |
| 955 | A25-M2-B36 | 1A | 3.565 | 418 |
| 956 | A26-M2-B36 | 1A | 3.115 | 412 |
| 957 | A35-M2-B36 | 1A | 3.14 | 404 |
| 958 | A33-M2-B36 | 1A | 2.63 | 356 |
| 959 | A5-M2-B36 | 1A | 2.82 | 410 |
| 960 | A27-M2-B36 | 1A | 2.44 | 342 |
| 961 | A28-M2-B36 | 1A | 2.89 | 394 |
| 962 | A29-M2-B36 | 1A | 2.07 | 314 |
| 963 | A1-M2-B36 | 1A | 2.73 | 376 |
| 964 | A8-M2-B36 | 1A | 2.895 | 394 |
| 965 | A30-M2-B36 | 1A | 3.2 | 408 |
| 966 | A17-M2-B37 | 1A | 2.15 | 463 |
| 967 | A31-M2-B37 | 1A |  | 476 |
| 968 | A18-M2-B37 | 1A | 2.445 | 467 |
| 969 | A19-M2-B37 | 1A | 2.545 | 461 |
| 970 | A20-M2-B37 | 1A | 2.03 | 451 |
| 971 | A32-M2-B37 | 1A | 1.62 | 434 |
| 972 | A11-M2-B37 | 1A |  | 477 |
| 973 | A21-M2-B37 | 1A | 2.095 | 447 |
| 974 | A4-M2-B37 | 1A | 1.965 | 413 |
| 975 | A6-M2-B37 | 1A | 2.225 | 463 |
| 976 | A24-M2-B37 | 1A | 2.605 | 461 |
| 977 | A25-M2-B37 | 1A | 2.89 | 475 |
| 978 | A26-M2-B37 | 1A | 2.335 | 469 |
| 979 | A35-M2-B37 | 1A | 2.42 | 461 |
| 980 | A36-M2-B37 | 1A | 2.15 | 481 |
| 981 | A33-M2-B37 | 1A | 1.93 | 413 |
| 982 | A5-M2-B37 | 1A | 2.08 | 467 |
| 983 | A27-M2-B37 | 1A | 1.735 | 399 |
| 984 | A28-M2-B37 | 1A | 2.13 | 451 |
| 985 | A29-M2-B37 | 1A | 1.485 | 371 |
| 986 | A1-M2-B37 | 1A | 2.01 | 433 |
| 987 | A8-M2-B37 | 1A | 2.135 | 451 |
| 988 | A17-M2-B38 | 1A | 3.02 | 452 |
| 989 | A31-M2-B38 | 1A | 2.88 | 465 |
| 990 | A18-M2-B38 | 1A | 3.37 | 456 |
| 991 | A32-M2-B38 | 1A | 2.44 | 423 |
| 992 | A11-M2-B38 | 1A | 2.94 | 466 |
| 993 | A21-M2-B38 | 1A | 3.035 | 436 |
| 994 | A22-M2-B38 | 1A | 2.98 | 452 |
| 995 | A4-M2-B38 | 1A | 2.94 | 402 |
| 996 | A26-M2-B38 | 1A | 3.29 | 458 |
| 997 | A35-M2-B38 | 1A | 3.31 | 450 |
| 998 | A36-M2-B38 | 1A | 3.06 | 470 |
| 999 | A5-M2-B38 | 1A | 3.02 | 456 |
| 1000 | A34-M2-B38 | 1A | 2.48 | 374 |
| 1001 | A27-M2-B38 | 1A | 2.66 | 388 |
| 1002 | A28-M2-B38 | 1A | 3.08 | 440 |
| 1003 | A8-M2-B38 | 1A | 3.09 | 440 |
| 1004 | A30-M2-B38 | 1A | 3.37 | 454 |
| 1005 | A17-M2-B39 | 1A | 3.14 | 422 |
| 1006 | A31-M2-B39 | 1A | 3.02 | 435 |
| 1007 | A18-M2-B39 | 1A | 3.49 | 426 |
| 1008 | A3-M2-B39 | 1A | 2.76 | 356 |
| 1009 | A19-M2-B39 | 1A | 3.52 | 420 |
| 1010 | A20-M2-B39 | 1A | 3.09 | 410 |
| 1011 | A32-M2-B39 | 1A | 2.585 | 393 |
| 1012 | A11-M2-B39 | 1A | 3.055 | 436 |
| 1013 | A22-M2-B39 | 1A | 3.115 | 422 |
| 1014 | A4-M2-B39 | 1A | 3.1 | 372 |
| 1015 | A6-M2-B39 | 1A | 3.24 | 422 |
| 1016 | A23-M2-B39 | 1A | 2.53 | 360 |
| 1017 | A24-M2-B39 | 1A | 3.6 | 420 |
| 1018 | A25-M2-B39 | 1A | 3.81 | 434 |
| 1019 | A26-M2-B39 | 1A | 3.41 | 428 |
| 1020 | A35-M2-B39 | 1A | 3.44 | 420 |
| 1021 | A36-M2-B39 | 1A | 3.18 | 440 |
| 1022 | A33-M2-B39 | 1A | 3 | 372 |
| 1023 | A5-M2-B39 | 1A | 3.14 | 426 |
| 1024 | A27-M2-B39 | 1A | 2.82 | 358 |
| 1025 | A28-M2-B39 | 1A | 3.22 | 410 |
| 1026 | A1-M2-B39 | 1A | 3.07 | 392 |
| 1027 | A8-M2-B39 | 1A | 3.22 | 410 |
| 1028 | A30-M2-B39 | 1A | 3.48 | 424 |
| 1029 | A19-M2-B40 | 1A | 2.59 | 475 |
| 1030 | A20-M2-B40 | 1A | 2.08 | 465 |
| 1031 | A32-M2-B40 | 1A | 1.66 | 448 |
| 1032 | A11-M2-B40 | 1A | 2.07 | 491 |
| 1033 | A21-M2-B40 | 1A | 2.12 | 461 |
| 1034 | A4-M2-B40 | 1A | 2.005 | 427 |
| 1035 | A24-M2-B40 | 1A | 2.64 | 475 |
| 1036 | A25-M2-B40 | 1A | 2.89 | 489 |
| 1037 | A26-M2-B40 | 1A | 2.355 | 483 |
| 1038 | A35-M2-B40 | 1A | 2.43 | 475 |
| 1039 | A36-M2-B40 | 1A | 2.18 | 495 |
| 1040 | A5-M2-B40 | 1A | 2.11 | 481 |
| 1041 | A27-M2-B40 | 1A | 1.8 | 413 |
| 1042 | A28-M2-B40 | 1A | 2.165 | 465 |
| 1043 | A1-M2-B40 | 1A | 2.06 | 447 |
| 1044 | A8-M2-B40 | 1A | 2.175 | 465 |
| 1045 | A30-M2-B40 | 1A | 2.49 | 479 |
| 1046 | A17-M2-B41 | 1A | 2.98 | 420 |
| 1047 | A18-M2-B41 | 1A | 3.34 | 424 |
| 1048 | A19-M2-B41 | 1A | 3.38 | 418 |
| 1049 | A32-M2-B41 | 1A | 2.4 | 391 |
| 1050 | A11-M2-B41 | 1A | 2.895 | 434 |
| 1051 | A21-M2-B41 | 1A | 2.995 | 404 |
| 1052 | A24-M2-B41 | 1A | 3.445 | 418 |
| 1053 | A25-M2-B41 | 1A | 3.67 | 432 |
| 1054 | A33-M2-B41 | 1A | 2.81 | 370 |
| 1055 | A5-M2-B41 | 1A | 2.99 | 424 |
| 1056 | A28-M2-B41 | 1A | 3.055 | 408 |
| 1057 | A1-M2-B41 | 1A | 2.89 | 390 |
| 1058 | A17-M2-B42 | 1A | 3.18 | 434 |
| 1059 | A31-M2-B42 | 1A | 3.065 | 447 |
| 1060 | A37-M2-B42 | 1A | 3.24 | 447 |
| 1061 | A19-M2-B42 | 1A | 3.54 | 432 |
| 1062 | A20-M2-B42 | 1A | 3.13 | 422 |
| 1063 | A32-M2-B42 | 1A | 2.63 | 405 |
| 1064 | A11-M2-B42 | 1A | 3.095 | 448 |
| 1065 | A21-M2-B42 | 1A | 3.19 | 418 |
| 1066 | A4-M2-B42 | 1A | 3.13 | 384 |
| 1067 | A6-M2-B42 | 1A | 3.27 | 434 |
| 1068 | A24-M2-B42 | 1A | 3.6 | 432 |
| 1069 | A26-M2-B42 | 1A | 3.44 | 440 |
| 1070 | A34-M2-B42 | 1A | 2.68 | 356 |
| 1071 | A28-M2-B42 | 1A | 3.24 | 422 |
| 1072 | A1-M2-B42 | 1A | 3.09 | 404 |
| 1073 | A8-M2-B42 | 1A | 3.25 | 422 |
| 1074 | A1-M2-B43 | 1A | 2.125 | 433 |
| 1075 | A17-M2-B6 | 1A | 2.75 | 394 |
| 1076 | A3-M2-B6 | 1A | 2.27 | 328 |
| 1077 | A19-M2-B6 | 1A | 3.17 | 392 |
| 1078 | A20-M2-B6 | 1A | 2.67 | 382 |

TABLE III-continued

| Entry | Compound | HPLC method | HPLC RT min | [M + H]+ |
|---|---|---|---|---|
| 1079 | A32-M2-B6 | 1A | 2.11 | 365 |
| 1080 | A11-M2-B6 | 1A | 2.63 | 408 |
| 1081 | A22-M2-B6 | 1A | 2.7 | 394 |
| 1082 | A4-M2-B6 | 1A | 2.63 | 344 |
| 1083 | A6-M2-B6 | 1A | 2.83 | 394 |
| 1084 | A24-M2-B6 | 1A | 3.25 | 392 |
| 1085 | A26-M2-B6 | 1A | 3.02 | 400 |
| 1086 | A33-M2-B6 | 1A | 2.54 | 344 |
| 1087 | A5-M2-B6 | 1A | 2.72 | 398 |
| 1088 | A28-M2-B6 | 1A | 2.8 | 382 |
| 1089 | A8-M2-B43 | 1A | 2.255 | 451 |
| 1090 | A17-M2-B43 | 1A | 2.235 | 463 |
| 1091 | A31-M2-B43 | 1A | 2.115 | 476 |
| 1092 | A18-M2-B43 | 1A | 2.58 | 467 |
| 1093 | A3-M2-B43 | 1A | 1.81 | 397 |
| 1094 | A19-M2-B43 | 1A | 2.625 | 461 |
| 1095 | A20-M2-B43 | 1A | 2.145 | 451 |
| 1096 | A32-M2-B43 | 1A | 1.725 | 434 |
| 1097 | A11-M2-B43 | 1A | 2.14 | 477 |
| 1098 | A6-M2-B43 | 1A | 2.34 | 463 |
| 1099 | A24-M2-B43 | 1A | 2.705 | 461 |
| 1100 | A38-M2-B41 | 3 | 5.02 | 458 |
| 1101 | A39-M2-B8 | 3 | 5.28 | 432 |
| 1102 | A39-M2-B34 | 3 | 4.71 | 529 |
| 1103 | A45-M2-B24 | 1A | 1.51 | 407 |
| 1104 | A41-M2-B24 | 1A | 1.94 | 469 |
| 1105 | A42-M2-B24 | 1A | 1.59 | 421 |
| 1106 | A43-M2-B24 | 1A | 2.31 | 501 |
| 1107 | A45-M2-B26 | 1A | 1.74 | 401 |
| 1108 | A42-M2-B26 | 1A | 1.84 | 415 |
| 1109 | A44-M2-B26 | 1A | 2.43 | 499 |
| 1110 | A45-M2-B27 | 1A | 2.46 | 366 |
| 1111 | A42-M2-B27 | 1A | 2.56 | 380 |
| 1112 | A43-M2-B27 | 1A | 3.33 | 460 |
| 1113 | A44-M2-B27 | 1A | 3.16 | 464 |
| 1114 | A41-M2-B28 | 1A | 3.07 | 440 |
| 1115 | A43-M2-B28 | 1A | 3.43 | 472 |
| 1116 | A44-M2-B28 | 1A | 3.27 | 476 |
| 1117 | A45-M2-B29 | 1A | 1.535 | 381 |
| 1118 | A42-M2-B29 | 1A | 1.64 | 395 |
| 1119 | A44-M2-B29 | 1A | 2.17 | 479 |
| 1120 | A45-M2-B8 | 1A | 2.32 | 364 |
| 1121 | A41-M2-B8 | 1A | 2.805 | 426 |
| 1122 | A42-M2-B8 | 1A | 2.42 | 378 |
| 1123 | A43-M2-B8 | 1A | 3.18 | 458 |
| 1124 | A44-M2-B8 | 1A | 3.01 | 462 |
| 1125 | A45-M2-B10 | 1A | 2.23 | 352 |
| 1126 | A42-M2-B10 | 1A | 2.35 | 366 |
| 1127 | A43-M2-B10 | 1A | 3.13 | 446 |
| 1128 | A44-M2-B10 | 1A | 2.97 | 450 |
| 1129 | A45-M2-B17 | 1A | 2.505 | 366 |
| 1130 | A41-M2-B17 | 1A | 2.98 | 428 |
| 1131 | A42-M2-B17 | 1A | 2.62 | 380 |
| 1132 | A43-M2-B17 | 1A | 3.35 | 460 |
| 1133 | A44-M2-B17 | 1A | 3.195 | 464 |
| 1134 | A45-M2-B30 | 1A | 2.08 | 350 |
| 1135 | A45-M2-B3 | 1A | 1.47 | 393 |
| 1136 | A41-M2-B3 | 1A | 1.91 | 455 |
| 1137 | A42-M2-B3 | 1A | 1.56 | 407 |
| 1138 | A45-M2-B7 | 1A | 2.03 | 380 |
| 1139 | A42-M2-B7 | 1A | 2.13 | 394 |
| 1140 | A43-M2-B7 | 1A | 2.92 | 474 |
| 1141 | A44-M2-B7 | 1A | 2.76 | 478 |
| 1142 | A45-M2-B31 | 1A | 1.69 | 421 |
| 1143 | A44-M2-B31 | 1A | 2.29 | 519 |
| 1144 | A45-M2-B32 | 1A | 1.56 | 421 |
| 1145 | A41-M2-B32 | 1A | 1.98 | 483 |
| 1146 | A42-M2-B32 | 1A | 1.64 | 435 |
| 1147 | A43-M2-B32 | 1A | 2.325 | 515 |
| 1148 | A44-M2-B32 | 1A | 2.16 | 519 |
| 1149 | A45-M2-B33 | 1A | 2.01 | 368 |
| 1150 | A41-M2-B33 | 1A | 2.53 | 430 |
| 1151 | A42-M2-B33 | 1A | 2.125 | 382 |
| 1152 | A44-M2-B33 | 1A | 2.75 | 466 |
| 1153 | A41-M2-B34 | 1A | 2.03 | 523 |
| 1154 | A42-M2-B34 | 1A | 1.705 | 475 |
| 1155 | A44-M2-B34 | 1A | 2.21 | 559 |
| 1156 | A45-M2-B35 | 1A | 1.775 | 456 |
| 1157 | A41-M2-B35 | 1A | 2.205 | 518 |
| 1158 | A42-M2-B35 | 1A | 1.865 | 470 |
| 1159 | A43-M2-B35 | 1A | 2.55 | 550 |
| 1160 | A44-M2-B35 | 1A | 2.385 | 554 |
| 1161 | A45-M2-B36 | 1A | 2.14 | 350 |
| 1162 | A41-M2-B36 | 1A | 2.68 | 412 |
| 1163 | A43-M2-B36 | 1A | 3.08 | 444 |
| 1164 | A44-M2-B36 | 1A | 2.89 | 448 |
| 1165 | A45-M2-B37 | 1A | 1.5 | 407 |
| 1166 | A41-M2-B37 | 1A | 1.93 | 469 |
| 1167 | A42-M2-B37 | 1A | 1.57 | 421 |
| 1168 | A43-M2-B37 | 1A | 2.265 | 501 |
| 1169 | A44-M2-B37 | 1A | 2.1 | 505 |
| 1170 | A45-M2-B38 | 1A | 2.39 | 396 |
| 1171 | A41-M2-B38 | 1A | 2.89 | 458 |
| 1172 | A42-M2-B38 | 1A | 2.505 | 410 |
| 1173 | A43-M2-B38 | 1A | 3.27 | 490 |
| 1174 | A44-M2-B38 | 1A | 3.11 | 494 |
| 1175 | A41-M2-B39 | 1A | 3.035 | 428 |
| 1176 | A42-M2-B39 | 1A | 2.64 | 380 |
| 1177 | A43-M2-B39 | 1A | 3.39 | 460 |
| 1178 | A44-M2-B39 | 1A | 3.23 | 464 |
| 1179 | A45-M2-B40 | 1A | 1.545 | 421 |
| 1180 | A41-M2-B40 | 1A | 1.95 | 483 |
| 1181 | A42-M2-B40 | 1A | 1.63 | 435 |
| 1182 | A43-M2-B40 | 1A | 2.27 | 515 |
| 1183 | A44-M2-B40 | 1A | 2.13 | 519 |
| 1184 | A45-M2-B41 | 1A | 2.35 | 364 |
| 1185 | A41-M2-B41 | 1A | 2.855 | 426 |
| 1186 | A45-M2-B42 | 1A | 2.59 | 378 |
| 1187 | A42-M2-B42 | 1A | 2.68 | 392 |
| 1188 | A44-M2-B42 | 1A | 3.26 | 476 |
| 1189 | A44-M2-B6 | 1A | 2.78 | 436 |
| 1190 | A40-M1-B11 | 2 | 5.73 | 488 |
| 1191 | A41-M1-B24 | 1A | 1.83 | 455 |
| 1192 | A42-M1-B24 | 1A | 1.51 | 407 |
| 1193 | A43-M1-B24 | 1A | 2.165 | 487 |
| 1194 | A44-M1-B24 | 1A | 1.98 | 491 |
| 1195 | A45-M1-B25 | 1A | 1.51 | 387 |
| 1196 | A42-M1-B25 | 1A | 1.605 | 401 |
| 1197 | A45-M1-B26 | 1A | 1.63 | 387 |
| 1198 | A42-M1-B26 | 1A | 1.73 | 401 |
| 1199 | A44-M1-B26 | 1A | 2.3 | 485 |
| 1200 | A45-M1-B27 | 1A | 2.33 | 352 |
| 1201 | A41-M1-B27 | 1A | 2.87 | 414 |
| 1202 | A42-M1-B27 | 1A | 2.46 | 366 |
| 1203 | A43-M1-B27 | 1A | 3.24 | 446 |
| 1204 | A44-M1-B27 | 1A | 3.05 | 450 |
| 1205 | A45-M1-B28 | 1A | 2.47 | 364 |
| 1206 | A41-M1-B28 | 1A | 2.985 | 426 |
| 1207 | A42-M1-B28 | 1A | 2.6 | 378 |
| 1208 | A43-M1-B28 | 1A | 3.34 | 458 |
| 1209 | A44-M1-B28 | 1A | 3.155 | 462 |
| 1210 | A42-M1-B29 | 1A | 1.55 | 381 |
| 1211 | A44-M1-B29 | 1A | 2.05 | 465 |
| 1212 | A45-M1-B8 | 1A | 2.185 | 350 |
| 1213 | A41-M1-B8 | 1A | 2.71 | 412 |
| 1214 | A42-M1-B8 | 1A | 2.32 | 364 |
| 1215 | A43-M1-B8 | 1A | 3.09 | 444 |
| 1216 | A44-M1-B8 | 1A | 2.9 | 448 |
| 1217 | A45-M1-B10 | 1A | 2.1 | 338 |
| 1218 | A41-M1-B10 | 1A | 2.66 | 400 |
| 1219 | A42-M1-B10 | 1A | 2.225 | 352 |
| 1220 | A43-M1-B10 | 1A | 3.045 | 432 |
| 1221 | A44-M1-B10 | 1A | 2.85 | 436 |
| 1222 | A45-M1-B17 | 1A | 2.395 | 352 |
| 1223 | A41-M1-B17 | 1A | 2.9 | 414 |
| 1224 | A42-M1-B17 | 1A | 2.515 | 366 |
| 1225 | A43-M1-B17 | 1A | 3.275 | 446 |
| 1226 | A44-M1-B17 | 1A | 3.1 | 450 |
| 1227 | A45-M1-B30 | 1A | 1.955 | 336 |
| 1228 | A42-M1-B30 | 1A | 2.09 | 350 |
| 1229 | A43-M1-B30 | 1A | 2.9 | 430 |
| 1230 | A44-M1-B30 | 1A | 2.7 | 434 |
| 1231 | A41-M1-B3 | 1A | 1.8 | 441 |
| 1232 | A42-M1-B3 | 1A | 1.465 | 393 |

TABLE III-continued

| Entry | Compound | HPLC method | HPLC RT min | [M + H]+ |
|---|---|---|---|---|
| 1233 | A43-M1-B3 | 1A | 2.135 | 473 |
| 1234 | A44-M1-B3 | 1A | 1.94 | 477 |
| 1235 | A45-M1-B7 | 1A | 1.91 | 366 |
| 1236 | A41-M1-B7 | 1A | 2.45 | 428 |
| 1237 | A42-M1-B7 | 1A | 2.03 | 380 |
| 1238 | A43-M1-B7 | 1A | 2.835 | 460 |
| 1239 | A44-M1-B7 | 1A | 2.63 | 464 |
| 1240 | A44-M1-B31 | 1A | 2.18 | 505 |
| 1241 | A45-M1-B32 | 1A | 1.485 | 407 |
| 1242 | A41-M1-B32 | 1A | 1.89 | 469 |
| 1243 | A42-M1-B32 | 1A | 1.56 | 421 |
| 1244 | A43-M1-B32 | 1A | 2.21 | 501 |
| 1245 | A44-M1-B32 | 1A | 2.045 | 505 |
| 1246 | A41-M1-B33 | 1A | 2.425 | 416 |
| 1247 | A42-M1-B33 | 1A | 2.02 | 368 |
| 1248 | A43-M1-B33 | 1A | 2.82 | 448 |
| 1249 | A44-M1-B33 | 1A | 2.62 | 452 |
| 1250 | A41-M1-B34 | 1A | 1.96 | 509 |
| 1251 | A43-M1-B34 | 1A | 2.29 | 541 |
| 1252 | A44-M1-B34 | 1A | 2.11 | 545 |
| 1253 | A45-M1-B35 | 1A | 1.7 | 442 |
| 1254 | A41-M1-B35 | 1A | 2.12 | 504 |
| 1255 | A42-M1-B35 | 1A | 1.785 | 456 |
| 1256 | A43-M1-B35 | 1A | 2.46 | 536 |
| 1257 | A44-M1-B35 | 1A | 2.28 | 540 |
| 1258 | A45-M1-B36 | 1A | 2.01 | 336 |
| 1259 | A41-M1-B36 | 1A | 2.595 | 398 |
| 1260 | A42-M1-B36 | 1A | 2.15 | 350 |
| 1261 | A43-M1-B36 | 1A | 2.98 | 430 |
| 1262 | A44-M1-B36 | 1A | 2.77 | 434 |
| 1263 | A41-M1-B37 | 1A | 1.82 | 455 |
| 1264 | A42-M1-B37 | 1A | 1.5 | 407 |
| 1265 | A43-M1-B37 | 1A | 2.18 | 487 |
| 1266 | A44-M1-B37 | 1A | 1.965 | 491 |
| 1267 | A45-M1-B38 | 1A | 2.29 | 382 |
| 1268 | A41-M1-B38 | 1A | 2.83 | 444 |
| 1269 | A42-M1-B38 | 1A | 2.41 | 396 |
| 1270 | A43-M1-B38 | 1A | 3.2 | 476 |
| 1271 | A44-M1-B38 | 1A | 3.01 | 480 |
| 1272 | A45-M1-B39 | 1A | 2.42 | 352 |
| 1273 | A41-M1-B39 | 1A | 2.95 | 414 |
| 1274 | A42-M1-B39 | 1A | 2.56 | 366 |
| 1275 | A43-M1-B39 | 1A | 3.315 | 446 |
| 1276 | A44-M1-B39 | 1A | 3.13 | 450 |
| 1277 | A45-M1-B40 | 1A | 1.47 | 407 |
| 1278 | A41-M1-B40 | 1A | 1.865 | 469 |
| 1279 | A42-M1-B40 | 1A | 1.55 | 421 |
| 1280 | A43-M1-B40 | 1A | 2.2 | 501 |
| 1281 | A44-M1-B40 | 1A | 2.005 | 505 |
| 1282 | A45-M1-B41 | 1A | 2.225 | 350 |
| 1283 | A41-M1-B41 | 1A | 2.765 | 412 |
| 1284 | A42-M1-B41 | 1A | 2.355 | 364 |
| 1285 | A43-M1-B41 | 1A | 3.135 | 444 |
| 1286 | A44-M1-B41 | 1A | 2.955 | 448 |
| 1287 | A45-M1-B42 | 1A | 2.49 | 364 |
| 1288 | A41-M1-B42 | 1A | 3 | 426 |
| 1289 | A42-M1-B42 | 1A | 2.6 | 378 |
| 1290 | A44-M1-B42 | 1A | 3.19 | 462 |
| 1291 | A41-M1-B6 | 1A | 2.48 | 386 |
| 1292 | A42-M1-B6 | 1A | 2.04 | 338 |
| 1293 | A43-M1-B6 | 1A | 2.88 | 418 |
| 1294 | A44-M1-B6 | 1A | 2.67 | 422 |
| 1295 | A42-M1-B43 | 1A | 1.61 | 407 |
| 1296 | A44-M1-B43 | 1A | 2.09 | 491 |
| 1297 | A46-M1-B24 | 1A | 2.085 | 434 |
| 1298 | A47-M1-B24 | 1A | 2.27 | 464 |
| 1299 | A48-M1-B24 | 1A | 2.365 | 448 |
| 1300 | A49-M1-B24 | 1A | 2.165 | 466 |
| 1301 | A50-M1-B24 | 1A | 1.715 | 442 |
| 1302 | A51-M1-B24 | 1A | 1.985 | 414 |
| 1303 | A52-M1-B24 | 1A | 1.465 | 372 |
| 1304 | A53-M1-B24 | 1A | 1.58 | 416 |
| 1305 | A54-M1-B25 | 1A | 2.445 | 434 |
| 1306 | A48-M1-B25 | 1A | 2.495 | 442 |
| 1307 | A49-M1-B25 | 1A | 2.285 | 460 |
| 1308 | A50-M1-B25 | 1A | 1.815 | 436 |
| 1309 | A51-M1-B25 | 1A | 2.12 | 408 |
| 1310 | A52-M1-B25 | 1A | 1.535 | 366 |
| 1311 | A53-M1-B25 | 1A | 1.66 | 410 |
| 1312 | A54-M1-B26 | 1A | 2.655 | 434 |
| 1313 | A46-M1-B26 | 1A | 2.4 | 428 |
| 1314 | A47-M1-B26 | 1A | 2.57 | 458 |
| 1315 | A48-M1-B26 | 1A | 2.7 | 442 |
| 1316 | A49-M1-B26 | 1A | 2.495 | 460 |
| 1317 | A50-M1-B26 | 1A | 1.96 | 436 |
| 1318 | A51-M1-B26 | 1A | 2.3 | 408 |
| 1319 | A52-M1-B26 | 1A | 1.66 | 366 |
| 1320 | A53-M1-B26 | 1A | 1.79 | 410 |
| 1321 | A54-M1-B27 | 1A | 3.43 | 399 |
| 1322 | A46-M1-B27 | 1A | 3.19 | 393 |
| 1323 | A47-M1-B27 | 1A | 3.295 | 423 |
| 1324 | A48-M1-B27 | 1A | 3.455 | 407 |
| 1325 | A49-M1-B27 | 1A | 3.295 | 425 |
| 1326 | A50-M1-B27 | 1A | 2.68 | 401 |
| 1327 | A51-M1-B27 | 1A | 3.125 | 373 |
| 1328 | A52-M1-B27 | 1A | 2.345 | 331 |
| 1329 | A53-M1-B27 | 1A | 2.485 | 375 |
| 1330 | A54-M1-B28 | 1A | 3.53 | 411 |
| 1331 | A46-M1-B28 | 1A | 3.3 | 405 |
| 1332 | A47-M1-B28 | 1A | 3.38 | 435 |
| 1333 | A48-M1-B28 | 1A | 3.55 | 419 |
| 1334 | A49-M1-B28 | 1A | 3.39 | 437 |
| 1335 | A50-M1-B28 | 1A | 2.805 | 413 |
| 1336 | A51-M1-B28 | 1A | 3.24 | 385 |
| 1337 | A52-M1-B28 | 1A | 2.475 | 343 |
| 1338 | A53-M1-B28 | 1A | 2.625 | 387 |
| 1339 | A54-M1-B29 | 1A | 2.39 | 414 |
| 1340 | A47-M1-B29 | 1A | 2.295 | 438 |
| 1341 | A48-M1-B29 | 1A | 2.415 | 422 |
| 1342 | A49-M1-B29 | 1A | 2.225 | 440 |
| 1343 | A50-M1-B29 | 1A | 1.76 | 416 |
| 1344 | A51-M1-B29 | 1A | 2.045 | 388 |
| 1345 | A53-M1-B29 | 1A | 1.62 | 390 |
| 1346 | A54-M1-B8 | 1A | 3.27 | 397 |
| 1347 | A46-M1-B8 | 1A | 3.05 | 391 |
| 1348 | A48-M1-B8 | 1A | 3.305 | 405 |
| 1349 | A49-M1-B8 | 1A | 3.125 | 423 |
| 1350 | A50-M1-B8 | 1A | 2.52 | 399 |
| 1351 | A51-M1-B8 | 1A | 2.95 | 371 |
| 1352 | A52-M1-B8 | 1A | 2.185 | 329 |
| 1353 | A53-M1-B8 | 1A | 2.33 | 373 |
| 1354 | A46-M1-B10 | 1A | 2.98 | 379 |
| 1355 | A47-M1-B10 | 1A | 3.15 | 409 |
| 1356 | A48-M1-B10 | 1A | 3.26 | 393 |
| 1357 | A49-M1-B10 | 1A | 3.1 | 411 |
| 1358 | A50-M1-B10 | 1A | 2.46 | 387 |
| 1359 | A51-M1-B10 | 1A | 2.905 | 359 |
| 1360 | A52-M1-B10 | 1A | 2.11 | 317 |
| 1361 | A53-M1-B10 | 1A | 2.265 | 361 |
| 1362 | A54-M1-B17 | 1A | 3.45 | 399 |
| 1363 | A46-M1-B17 | 1A | 3.23 | 393 |
| 1364 | A47-M1-B17 | 1A | 3.32 | 423 |
| 1365 | A48-M1-B17 | 1A | 3.475 | 407 |
| 1366 | A49-M1-B17 | 1A | 3.305 | 425 |
| 1367 | A50-M1-B17 | 1A | 2.72 | 401 |
| 1368 | A51-M1-B17 | 1A | 3.15 | 373 |
| 1369 | A53-M1-B17 | 1A | 2.53 | 375 |
| 1370 | A47-M1-B30 | 1A | 2.97 | 407 |
| 1371 | A48-M1-B30 | 1A | 3.135 | 391 |
| 1372 | A49-M1-B30 | 1A | 2.945 | 409 |
| 1373 | A50-M1-B30 | 1A | 2.315 | 385 |
| 1374 | A51-M1-B30 | 1A | 2.75 | 357 |
| 1375 | A52-M1-B30 | 1A | 1.97 | 315 |
| 1376 | A53-M1-B30 | 1A | 2.125 | 359 |
| 1377 | A54-M1-B3 | 1A | 2.29 | 426 |
| 1378 | A46-M1-B3 | 1A | 2.06 | 420 |
| 1379 | A47-M1-B3 | 1A | 2.205 | 450 |
| 1380 | A48-M1-B3 | 1A | 2.345 | 434 |
| 1381 | A49-M1-B3 | 1A | 2.13 | 452 |
| 1382 | A50-M1-B3 | 1A | 1.68 | 428 |
| 1383 | A51-M1-B3 | 1A | 1.95 | 400 |
| 1384 | A52-M1-B3 | 1A | 1.415 | 358 |
| 1385 | A53-M1-B3 | 1A | 1.54 | 402 |
| 1386 | A54-M1-B7 | 1A | 3.02 | 413 |

TABLE III-continued

| Entry | Compound | HPLC method | HPLC RT min | [M + H]+ |
|---|---|---|---|---|
| 1387 | A46-M1-B7 | 1A | 2.79 | 407 |
| 1388 | A48-M1-B7 | 1A | 3.065 | 421 |
| 1389 | A49-M1-B7 | 1A | 2.87 | 439 |
| 1390 | A50-M1-B7 | 1A | 2.25 | 415 |
| 1391 | A51-M1-B7 | 1A | 2.67 | 387 |
| 1392 | A52-M1-B7 | 1A | 1.92 | 345 |
| 1393 | A53-M1-B7 | 1A | 2.07 | 389 |
| 1394 | A54-M1-B31 | 1A | 2.52 | 454 |
| 1395 | A46-M1-B31 | 1A | 2.28 | 448 |
| 1396 | A47-M1-B31 | 1A | 2.43 | 478 |
| 1397 | A48-M1-B31 | 1A | 2.525 | 462 |
| 1398 | A49-M1-B31 | 1A | 2.345 | 480 |
| 1399 | A50-M1-B31 | 1A | 1.89 | 456 |
| 1400 | A51-M1-B31 | 1A | 2.2 | 428 |
| 1401 | A52-M1-B31 | 1A | 1.63 | 386 |
| 1402 | A53-M1-B31 | 1A | 1.74 | 430 |
| 1403 | A54-M1-B32 | 1A | 2.38 | 454 |
| 1404 | A46-M1-B32 | 1A | 2.14 | 448 |
| 1405 | A47-M1-B32 | 1A | 2.31 | 478 |
| 1406 | A48-M1-B32 | 1A | 2.415 | 462 |
| 1407 | A52-M1-B32 | 1A | 1.515 | 386 |
| 1408 | A53-M1-B32 | 1A | 1.635 | 430 |
| 1409 | A54-M1-B33 | 1A | 3.03 | 401 |
| 1410 | A47-M1-B33 | 1A | 2.89 | 425 |
| 1411 | A48-M1-B33 | 1A | 3.06 | 409 |
| 1412 | A49-M1-B33 | 1A | 2.86 | 427 |
| 1413 | A50-M1-B33 | 1A | 2.24 | 403 |
| 1414 | A51-M1-B33 | 1A | 2.67 | 375 |
| 1415 | A52-M1-B33 | 1A | 1.91 | 333 |
| 1416 | A53-M1-B33 | 1A | 2.06 | 377 |
| 1417 | A54-M1-B34 | 1A | 2.405 | 494 |
| 1418 | A47-M1-B34 | 1A | 2.34 | 518 |
| 1419 | A48-M1-B34 | 1A | 2.47 | 502 |
| 1420 | A49-M1-B34 | 1A | 2.28 | 520 |
| 1421 | A50-M1-B34 | 1A | 1.84 | 496 |
| 1422 | A51-M1-B34 | 1A | 2.1 | 468 |
| 1423 | A52-M1-B34 | 1A | 1.58 | 426 |
| 1424 | A53-M1-B34 | 1A | 1.69 | 470 |
| 1425 | A54-M1-B35 | 1A | 2.61 | 489 |
| 1426 | A48-M1-B35 | 1A | 2.625 | 497 |
| 1427 | A49-M1-B35 | 1A | 2.46 | 515 |
| 1428 | A50-M1-B35 | 1A | 1.97 | 491 |
| 1429 | A51-M1-B35 | 1A | 2.285 | 463 |
| 1430 | A52-M1-B35 | 1A | 1.705 | 421 |
| 1431 | A53-M1-B35 | 1A | 1.82 | 465 |
| 1432 | A47-M1-B36 | 1A | 3.06 | 407 |
| 1433 | A48-M1-B36 | 1A | 3.21 | 391 |
| 1434 | A49-M1-B36 | 1A | 3.03 | 409 |
| 1435 | A50-M1-B36 | 1A | 2.39 | 385 |
| 1436 | A51-M1-B36 | 1A | 2.85 | 357 |
| 1437 | A52-M1-B36 | 1A | 2.03 | 315 |
| 1438 | A53-M1-B36 | 1A | 2.18 | 359 |
| 1439 | A54-M1-B37 | 1A | 2.305 | 440 |
| 1440 | A47-M1-B37 | 1A | 2.26 | 464 |
| 1441 | A48-M1-B37 | 1A | 2.35 | 448 |
| 1442 | A49-M1-B37 | 1A | 2.17 | 466 |
| 1443 | A50-M1-B37 | 1A | 1.705 | 442 |
| 1444 | A51-M1-B37 | 1A | 1.975 | 414 |
| 1445 | A52-M1-B37 | 1A | 1.45 | 372 |
| 1446 | A53-M1-B37 | 1A | 1.57 | 416 |
| 1447 | A54-M1-B38 | 1A | 3.39 | 429 |
| 1448 | A46-M1-B38 | 1A | 3.14 | 423 |
| 1449 | A48-M1-B38 | 1A | 3.4 | 437 |
| 1450 | A49-M1-B38 | 1A | 3.24 | 455 |
| 1451 | A50-M1-B38 | 1A | 2.615 | 431 |
| 1452 | A51-M1-B38 | 1A | 3.065 | 403 |
| 1453 | A52-M1-B38 | 1A | 2.29 | 361 |
| 1454 | A53-M1-B38 | 1A | 2.425 | 405 |
| 1455 | A54-M1-B39 | 1A | 3.51 | 399 |
| 1456 | A46-M1-B39 | 1A | 3.27 | 393 |
| 1457 | A47-M1-B39 | 1A | 3.365 | 423 |
| 1458 | A48-M1-B39 | 1A | 3.53 | 407 |
| 1459 | A49-M1-B39 | 1A | 3.36 | 425 |
| 1460 | A50-M1-B39 | 1A | 2.78 | 401 |
| 1461 | A51-M1-B39 | 1A | 3.22 | 373 |
| 1462 | A52-M1-B39 | 1A | 2.43 | 331 |
| 1463 | A53-M1-B39 | 1A | 2.57 | 375 |
| 1464 | A54-M1-B40 | 1A | 2.34 | 454 |
| 1465 | A47-M1-B40 | 1A | 2.27 | 478 |
| 1466 | A48-M1-B40 | 1A | 2.41 | 462 |
| 1467 | A49-M1-B40 | 1A | 2.185 | 480 |
| 1468 | A50-M1-B40 | 1A | 1.74 | 456 |
| 1469 | A51-M1-B40 | 1A | 2.015 | 428 |
| 1470 | A52-M1-B40 | 1A | 1.495 | 386 |
| 1471 | A53-M1-B40 | 1A | 1.605 | 430 |
| 1472 | A54-M1-B41 | 1A | 3.335 | 397 |
| 1473 | A46-M1-B41 | 1A | 3.095 | 391 |
| 1474 | A47-M1-B41 | 1A | 3.195 | 421 |
| 1475 | A48-M1-B41 | 1A | 3.36 | 405 |
| 1476 | A49-M1-B41 | 1A | 3.19 | 423 |
| 1477 | A50-M1-B41 | 1A | 2.575 | 399 |
| 1478 | A51-M1-B41 | 1A | 3.025 | 371 |
| 1479 | A52-M1-B41 | 1A | 2.23 | 329 |
| 1480 | A53-M1-B41 | 1A | 2.38 | 373 |
| 1481 | A54-M1-B42 | 1A | 3.53 | 411 |
| 1482 | A46-M1-B42 | 1A | 3.32 | 405 |
| 1483 | A48-M1-B42 | 1A | 3.56 | 419 |
| 1484 | A49-M1-B42 | 1A | 3.39 | 437 |
| 1485 | A50-M1-B42 | 1A | 2.8 | 413 |
| 1486 | A51-M1-B42 | 1A | 3.25 | 385 |
| 1487 | A52-M1-B42 | 1A | 2.485 | 343 |
| 1488 | A53-M1-B42 | 1A | 2.62 | 387 |
| 1489 | A46-M1-B6 | 1A | 2.81 | 365 |
| 1490 | A47-M1-B6 | 1A | 2.94 | 395 |
| 1491 | A48-M1-B6 | 1A | 3.1 | 379 |
| 1492 | A49-M1-B6 | 1A | 2.91 | 397 |
| 1493 | A50-M1-B6 | 1A | 2.29 | 373 |
| 1494 | A51-M1-B6 | 1A | 2.72 | 345 |
| 1495 | A52-M1-B6 | 1A | 1.93 | 303 |
| 1496 | A53-M1-B6 | 1A | 2.08 | 347 |
| 1497 | A54-M1-B43 | 1A | 2.415 | 440 |
| 1498 | A48-M1-B43 | 1A | 2.475 | 448 |
| 1499 | A49-M1-B43 | 1A | 2.275 | 466 |
| 1500 | A51-M1-B43 | 1A | 2.095 | 414 |
| 1501 | A53-M1-B43 | 1A | 1.665 | 416 |
| 1502 | A54-M2-B24 | 1A | 2.405 | 454 |
| 1503 | A46-M2-B24 | 1A | 2.21 | 448 |
| 1504 | A47-M2-B24 | 1A | 2.36 | 478 |
| 1505 | A48-M2-B24 | 1A | 2.48 | 462 |
| 1506 | A49-M2-B24 | 1A | 2.265 | 480 |
| 1507 | A50-M2-B24 | 1A | 1.81 | 456 |
| 1508 | A51-M2-B24 | 1A | 2.095 | 428 |
| 1509 | A52-M2-B24 | 1A | 1.54 | 386 |
| 1510 | A53-M2-B24 | 1A | 1.66 | 430 |
| 1511 | A54-M2-B25 | 1A | 2.545 | 448 |
| 1512 | A48-M2-B25 | 1A | 2.61 | 456 |
| 1513 | A49-M2-B25 | 1A | 2.4 | 474 |
| 1514 | A51-M2-B25 | 1A | 2.23 | 422 |
| 1515 | A52-M2-B25 | 1A | 1.62 | 380 |
| 1516 | A54-M2-B26 | 1A | 2.825 | 448 |
| 1517 | A46-M2-B26 | 1A | 2.56 | 442 |
| 1518 | A47-M2-B26 | 1A | 2.68 | 472 |
| 1519 | A48-M2-B26 | 1A | 2.85 | 456 |
| 1520 | A49-M2-B26 | 1A | 2.65 | 474 |
| 1521 | A50-M2-B26 | 1A | 2.07 | 450 |
| 1522 | A51-M2-B26 | 1A | 2.46 | 422 |
| 1523 | A52-M2-B26 | 1A | 1.76 | 380 |
| 1524 | A54-M2-B27 | 1A | 3.6 | 413 |
| 1525 | A46-M2-B27 | 1A | 3.34 | 407 |
| 1526 | A47-M2-B27 | 1A | 3.42 | 437 |
| 1527 | A48-M2-B27 | 1A | 3.59 | 421 |
| 1528 | A49-M2-B27 | 1A | 3.44 | 439 |
| 1529 | A50-M2-B27 | 1A | 2.82 | 415 |
| 1530 | A51-M2-B27 | 1A | 3.31 | 387 |
| 1531 | A52-M2-B27 | 1A | 2.49 | 345 |
| 1532 | A53-M2-B27 | 1A | 2.625 | 389 |
| 1533 | A54-M2-B28 | 1A | 3.71 | 425 |
| 1534 | A46-M2-B28 | 1A | 3.44 | 419 |
| 1535 | A47-M2-B28 | 1A | 3.51 | 449 |
| 1536 | A48-M2-B28 | 1A | 3.69 | 433 |
| 1537 | A49-M2-B28 | 1A | 3.54 | 451 |
| 1538 | A50-M2-B28 | 1A | 2.94 | 427 |
| 1539 | A51-M2-B28 | 1A | 3.42 | 399 |
| 1540 | A52-M2-B28 | 1A | 2.63 | 357 |

TABLE III-continued

| Entry | Compound | HPLC method | HPLC RT min | [M + H]+ |
|---|---|---|---|---|
| 1541 | A54-M2-B29 | 1A | 2.45 | 428 |
| 1542 | A46-M2-B29 | 1A | 2.25 | 422 |
| 1543 | A47-M2-B29 | 1A | 2.4 | 452 |
| 1544 | A48-M2-B29 | 1A | 2.53 | 436 |
| 1545 | A50-M2-B29 | 1A | 1.86 | 430 |
| 1546 | A51-M2-B29 | 1A | 2.145 | 402 |
| 1547 | A53-M2-B29 | 1A | 1.71 | 404 |
| 1548 | A54-M2-B8 | 1A | 3.43 | 411 |
| 1549 | A46-M2-B8 | 1A | 3.185 | 405 |
| 1550 | A47-M2-B8 | 1A | 3.26 | 435 |
| 1551 | A48-M2-B8 | 1A | 3.425 | 419 |
| 1552 | A49-M2-B8 | 1A | 3.25 | 437 |
| 1553 | A50-M2-B8 | 1A | 2.645 | 413 |
| 1554 | A51-M2-B8 | 1A | 3.11 | 385 |
| 1555 | A52-M2-B8 | 1A | 2.33 | 343 |
| 1556 | A53-M2-B8 | 1A | 2.47 | 387 |
| 1557 | A54-M2-B10 | 1A | 3.4 | 399 |
| 1558 | A46-M2-B10 | 1A | 3.13 | 393 |
| 1559 | A47-M2-B10 | 1A | 3.22 | 423 |
| 1560 | A48-M2-B10 | 1A | 3.41 | 407 |
| 1561 | A49-M2-B10 | 1A | 3.225 | 425 |
| 1562 | A50-M2-B10 | 1A | 2.6 | 401 |
| 1563 | A51-M2-B10 | 1A | 3.08 | 373 |
| 1564 | A52-M2-B10 | 1A | 2.25 | 331 |
| 1565 | A53-M2-B10 | 1A | 2.4 | 375 |
| 1566 | A54-M2-B17 | 1A | 3.61 | 413 |
| 1567 | A46-M2-B17 | 1A | 3.355 | 407 |
| 1568 | A47-M2-B17 | 1A | 3.415 | 437 |
| 1569 | A48-M2-B17 | 1A | 3.605 | 421 |
| 1570 | A49-M2-B17 | 1A | 3.435 | 439 |
| 1571 | A50-M2-B17 | 1A | 2.83 | 415 |
| 1572 | A51-M2-B17 | 1A | 3.32 | 387 |
| 1573 | A52-M2-B17 | 1A | 2.52 | 345 |
| 1574 | A53-M2-B17 | 1A | 2.65 | 389 |
| 1575 | A46-M2-B30 | 1A | 3 | 391 |
| 1576 | A47-M2-B30 | 1A | 3.08 | 421 |
| 1577 | A48-M2-B30 | 1A | 3.27 | 405 |
| 1578 | A49-M2-B30 | 1A | 3.08 | 423 |
| 1579 | A50-M2-B30 | 1A | 2.445 | 399 |
| 1580 | A51-M2-B30 | 1A | 2.92 | 371 |
| 1581 | A46-M2-B3 | 1A | 2.14 | 434 |
| 1582 | A48-M2-B3 | 1A | 2.46 | 448 |
| 1583 | A49-M2-B3 | 1A | 2.22 | 466 |
| 1584 | A50-M2-B3 | 1A | 1.77 | 442 |
| 1585 | A51-M2-B3 | 1A | 2.07 | 414 |
| 1586 | A52-M2-B3 | 1A | 1.495 | 372 |
| 1587 | A53-M2-B3 | 1A | 1.62 | 416 |
| 1588 | A54-M2-B7 | 1A | 3.16 | 427 |
| 1589 | A46-M2-B7 | 1A | 2.9 | 421 |
| 1590 | A47-M2-B7 | 1A | 3 | 451 |
| 1591 | A48-M2-B7 | 1A | 3.19 | 435 |
| 1592 | A49-M2-B7 | 1A | 2.985 | 453 |
| 1593 | A50-M2-B7 | 1A | 2.36 | 429 |
| 1594 | A51-M2-B7 | 1A | 2.83 | 401 |
| 1595 | A53-M2-B7 | 1A | 2.18 | 403 |
| 1596 | A47-M2-B31 | 1A | 2.49 | 492 |
| 1597 | A49-M2-B31 | 1A | 2.445 | 494 |
| 1598 | A50-M2-B31 | 1A | 1.97 | 470 |
| 1599 | A51-M2-B31 | 1A | 2.28 | 442 |
| 1600 | A52-M2-B31 | 1A | 1.7 | 400 |
| 1601 | A53-M2-B31 | 1A | 1.83 | 444 |
| 1602 | A54-M2-B32 | 1A | 2.48 | 468 |
| 1603 | A51-M2-B32 | 1A | 2.16 | 442 |
| 1604 | A54-M2-B33 | 1A | 3.16 | 415 |
| 1605 | A46-M2-B33 | 1A | 2.9 | 409 |
| 1606 | A47-M2-B33 | 1A | 3 | 439 |
| 1607 | A48-M2-B33 | 1A | 3.19 | 423 |
| 1608 | A49-M2-B33 | 1A | 3 | 441 |
| 1609 | A50-M2-B33 | 1A | 2.37 | 417 |
| 1610 | A51-M2-B33 | 1A | 2.82 | 389 |
| 1611 | A52-M2-B33 | 1A | 2.025 | 347 |
| 1612 | A53-M2-B33 | 1A | 2.17 | 391 |
| 1613 | A54-M2-B34 | 1A | 2.495 | 508 |
| 1614 | A46-M2-B34 | 1A | 2.29 | 502 |
| 1615 | A47-M2-B34 | 1A | 2.42 | 532 |
| 1616 | A48-M2-B34 | 1A | 2.57 | 516 |
| 1617 | A49-M2-B34 | 1A | 2.355 | 534 |
| 1618 | A50-M2-B34 | 1A | 1.9 | 510 |
| 1619 | A51-M2-B34 | 1A | 2.2 | 482 |
| 1620 | A52-M2-B34 | 1A | 1.645 | 440 |
| 1621 | A53-M2-B34 | 1A | 1.755 | 484 |
| 1622 | A54-M2-B35 | 1A | 2.73 | 503 |
| 1623 | A46-M2-B35 | 1A | 2.49 | 497 |
| 1624 | A47-M2-B35 | 1A | 2.61 | 527 |
| 1625 | A48-M2-B35 | 1A | 2.765 | 511 |
| 1626 | A49-M2-B35 | 1A | 2.58 | 529 |
| 1627 | A50-M2-B35 | 1A | 2.07 | 505 |
| 1628 | A51-M2-B35 | 1A | 2.415 | 477 |
| 1629 | A52-M2-B35 | 1A | 1.8 | 435 |
| 1630 | A53-M2-B35 | 1A | 1.91 | 479 |
| 1631 | A47-M2-B36 | 1A | 3.155 | 421 |
| 1632 | A48-M2-B36 | 1A | 3.35 | 405 |
| 1633 | A49-M2-B36 | 1A | 3.15 | 423 |
| 1634 | A50-M2-B36 | 1A | 2.515 | 399 |
| 1635 | A51-M2-B36 | 1A | 3 | 371 |
| 1636 | A52-M2-B36 | 1A | 2.17 | 329 |
| 1637 | A53-M2-B36 | 1A | 2.315 | 373 |
| 1638 | A46-M2-B37 | 1A | 2.17 | 448 |
| 1639 | A47-M2-B37 | 1A | 2.33 | 478 |
| 1640 | A48-M2-B37 | 1A | 2.445 | 462 |
| 1641 | A49-M2-B37 | 1A | 2.27 | 480 |
| 1642 | A50-M2-B37 | 1A | 1.785 | 456 |
| 1643 | A51-M2-B37 | 1A | 2.07 | 428 |
| 1644 | A52-M2-B37 | 1A | 1.525 | 386 |
| 1645 | A53-M2-B37 | 1A | 1.64 | 430 |
| 1646 | A54-M2-B38 | 1A | 3.54 | 443 |
| 1647 | A46-M2-B38 | 1A | 3.27 | 437 |
| 1648 | A47-M2-B38 | 1A | 3.35 | 467 |
| 1649 | A48-M2-B38 | 1A | 3.53 | 451 |
| 1650 | A49-M2-B38 | 1A | 3.36 | 469 |
| 1651 | A50-M2-B38 | 1A | 2.73 | 445 |
| 1652 | A51-M2-B38 | 1A | 3.23 | 417 |
| 1653 | A52-M2-B38 | 1A | 2.42 | 375 |
| 1654 | A53-M2-B38 | 1A | 2.56 | 419 |
| 1655 | A54-M2-B39 | 1A | 3.66 | 413 |
| 1656 | A46-M2-B39 | 1A | 3.41 | 407 |
| 1657 | A47-M2-B39 | 1A | 3.47 | 437 |
| 1658 | A48-M2-B39 | 1A | 3.66 | 421 |
| 1659 | A49-M2-B39 | 1A | 3.5 | 439 |
| 1660 | A50-M2-B39 | 1A | 2.895 | 415 |
| 1661 | A51-M2-B39 | 1A | 3.38 | 387 |
| 1662 | A52-M2-B39 | 1A | 2.57 | 345 |
| 1663 | A53-M2-B39 | 1A | 2.71 | 389 |
| 1664 | A54-M2-B40 | 1A | 2.45 | 468 |
| 1665 | A46-M2-B40 | 1A | 2.21 | 462 |
| 1666 | A47-M2-B40 | 1A | 2.35 | 492 |
| 1667 | A48-M2-B40 | 1A | 2.51 | 476 |
| 1668 | A49-M2-B40 | 1A | 2.32 | 494 |
| 1669 | A50-M2-B40 | 1A | 1.83 | 470 |
| 1670 | A51-M2-B40 | 1A | 2.13 | 442 |
| 1671 | A52-M2-B40 | 1A | 1.57 | 400 |
| 1672 | A53-M2-B40 | 1A | 1.685 | 444 |
| 1673 | A54-M2-B41 | 1A | 3.5 | 411 |
| 1674 | A46-M2-B41 | 1A | 3.245 | 405 |
| 1675 | A47-M2-B41 | 1A | 3.31 | 435 |
| 1676 | A49-M2-B41 | 1A | 3.325 | 437 |
| 1677 | A50-M2-B41 | 1A | 2.7 | 413 |
| 1678 | A51-M2-B41 | 1A | 3.19 | 385 |
| 1679 | A52-M2-B41 | 1A | 2.375 | 343 |
| 1680 | A53-M2-B41 | 1A | 2.51 | 387 |
| 1681 | A54-M2-B42 | 1A | 3.68 | 425 |
| 1682 | A46-M2-B42 | 1A | 3.43 | 419 |
| 1683 | A47-M2-B42 | 1A | 3.49 | 449 |
| 1684 | A48-M2-B42 | 1A | 3.67 | 433 |
| 1685 | A49-M2-B42 | 1A | 3.5 | 451 |
| 1686 | A50-M2-B42 | 1A | 2.905 | 427 |
| 1687 | A52-M2-B42 | 1A | 2.605 | 357 |
| 1688 | A53-M2-B42 | 1A | 2.73 | 401 |
| 1689 | A54-M2-B6 | 1A | 3.22 | 385 |
| 1690 | A47-M2-B6 | 1A | 3.06 | 409 |
| 1691 | A48-M2-B43 | 1A | 2.56 | 462 |
| 1692 | A48-M2-B6 | 1A | 3.25 | 393 |
| 1693 | A49-M2-B6 | 1A | 3.045 | 411 |
| 1694 | A49-M2-B43 | 1A | 2.37 | 480 |

TABLE III-continued

| Entry | Compound | HPLC method | HPLC RT min | [M + H]+ |
|---|---|---|---|---|
| 1695 | A51-M2-B6 | 1A | 2.88 | 359 |
| 1696 | A52-M2-B43 | 1A | 1.63 | 386 |
| 1697 | A53-M2-B6 | 1A | 2.21 | 361 |
| 1698 | A47-M2-B43 | 1A | 2.44 | 478 |

Example 10

Preparation of the 2,4-dimethyl-N-[1-methyl-8-(pyrrolidin-1-ylcarbonyl)-4,5-dihydro-1H-pyrazolo[4,3-g]indolizin-3-yl]benzamide (I)

After dissolving the compound 2,4-dimethyl-N-[8-(pyrrolidin-1-ylcarbonyl)-4,5-dihydro-1H-pyrazolo[4,3-g]indolizin-3-yl]benzamide (A35-M1-B8, Entry 200, Table III), obtained as described in the example 9, in dichloromethane 2 equivalent of methyl iodide were added. After four hours of stirring at room temperature, water was added and the phases were separated. The organic layer was Dried over $Na_2SO_4$ and the crude was purified through preparative HPLC. LCMS m/z 418 [M+H]+@ Rt2.87 min.

1H NMR (DMSO-d6, 401 MHz): δ ppm=1.76-1.96 (m, 4 H), 2.32 (s, 3 H), 2.39 (s, 3 H), 2.86 (t, J=6.6 Hz, 2 H), 3.40-3.72 (m, 4 H), 4.09 (t, J=6.4 Hz, 2 H), 4.19 (s, 3H), 6.65 (br. s., 1 H), 7.04-7.14 (m, 2 H), 7.39 (br. s., 1 H), 7.40 (br. s., 1 H), 10.54 (br. s., 1 H).

The two possible tautomers were not isolated.

The invention claimed is:

1. A compound of formula (I):

(I)

wherein
n is 0;
R1, R2 and R4, each independently one from the other, are selected from the group consisting of —$R^a$, —$COR^a$, —$CONHR^a$, —$SO_2R^a$ and —$COOR^a$;
R3 is a group —$NR^aR^b$ or —$OR^a$;
wherein $R^a$ and $R^b$, the same or different, are each independently hydrogen or a group optionally substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl or, taken together with the nitrogen atom to which they are bonded, either $R^a$ and $R^b$, may form an optionally substituted 3 to 8 membered heterocycle, optionally containing one additional heteroatom or heteroatomic group selected from S, O, N or NH,
and pharmaceutically acceptable salts thereof.

2. A compound of formula (I) according to claim 1, wherein:
R1 is a group —$CONHR^a$ wherein $R^a$ is hydrogen or a group optionally substituted selected from straight or branched $C_1$-$C_6$ alkyl, straight or branched $C_2$-$C_6$ alkenyl, aryl and aryl $C_1$-$C_6$ alkyl.

3. A compound of formula (I) according to claim 1, wherein:
R1 is a group —$COR^a$ wherein $R^a$ is hydrogen or a group optionally substituted selected from straight or branched $C_1$-$C_6$ alkyl, straight or branched $C_2$-$C_6$ alkenyl, aryl and aryl $C_1$-$C_6$ alkyl.

4. A compound of formula (I) according to claim 1, wherein:
R1 is a group —$SO_2R^a$ wherein $R^a$ is hydrogen or a group optionally substituted selected from straight or branched $C_1$-$C_6$ alkyl, straight or branched $C_2$-$C_6$ alkenyl, aryl and aryl $C_1$-$C_6$ alkyl.

5. A compound of formula (I) according to any one of claims 1 to 4 wherein:
R2 is hydrogen.

6. A compound of formula (I) according to claim 1, wherein:
R3 is a group —$NR^aR^b$ wherein both of $R^a$ and $R^b$ are hydrogen or one of them is a hydrogen and the remaining one of $R^a$ or $R^b$ is a group optionally substituted selected from straight or branched $C_1$-$C_6$ alkyl, straight or branched $C_2$-$C_6$ alkenyl, aryl and aryl $C_1$-$C_6$ alkyl.

7. A compound of formula (I) according to claim 1, wherein: R4 is hydrogen.

8. A compound of formula (I) according to claim 1, wherein R1 and R2, each independently one from the other, are a substituent denoted by any of codes A1-A54 and R3 is a substituent denoted by any of codes B1-B43 listed below, wherein the compounds have the formula:

(I)

wherein substituents A and B are:

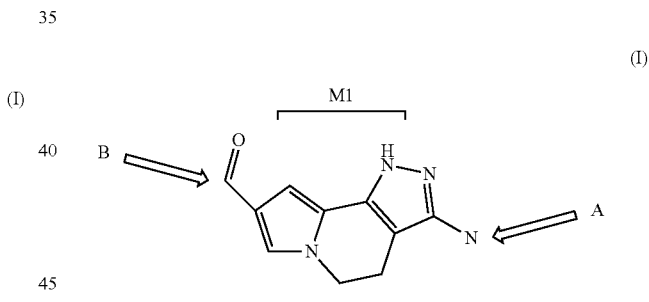

| FRAGMENT | CODE |
|---|---|
| M1 | A1 |
| M1 | A2 |
| M1 | A3 |

-continued

| FRAGMENT | CODE |
|---|---|
| (isobutyl-C(=O)-M1) | A4 |
| (2-chlorobenzoyl-M1) | A5 |
| (2-methoxybenzoyl-M1) | A6 |
| (2-thienyl-CH2-C(=O)-M1) | A7 |
| (3-fluorobenzoyl-M1) | A8 |
| (2-furoyl-M1) | A9 |
| (cyclopentyl-CH2CH2-C(=O)-M1) | A10 |
| (1,3-benzodioxol-5-yl-C(=O)-M1) | A11 |
| (4-methoxyphenyl-CH2-C(=O)-M1) | A12 |
| (2-methylpentanoyl-M1) | A13 |

-continued

| FRAGMENT | CODE |
|---|---|
| (4-methylbenzoyl-M1) | A14 |
| (phenyl-CH2CH2-C(=O)-M1) | A15 |
| (4-(4-methylpiperazin-1-yl)benzoyl-M1) | A16 |
| (3-methoxybenzoyl-M1) | A17 |
| (3-chlorobenzoyl-M1) | A18 |
| (3,4-dimethylbenzoyl-M1) | A19 |
| (2-fluorobenzoyl-M1) | A20 |
| (2-methylbenzoyl-M1) | A21 |
| (4-methoxybenzoyl-M1) | A22 |

| FRAGMENT | CODE |
|----------|------|
| methoxyacetyl | A23 |
| 3,5-dimethylbenzoyl | A24 |
| 4-isopropylbenzoyl | A25 |
| 3,4-difluorobenzoyl | A26 |
| isobutyryl | A27 |
| 4-fluorobenzoyl | A28 |
| acetyl | A29 |
| 3-fluoro-4-methylbenzoyl | A30 |
| 3-(dimethylamino)benzoyl | A31 |
| nicotinoyl (pyridine-3-carbonyl) | A32 |

| FRAGMENT | CODE |
|----------|------|
| pivaloyl | A33 |
| propionyl | A34 |
| 2,4-dimethylbenzoyl | A35 |
| 3-fluoro-4-methoxybenzoyl | A36 |
| 4-(dimethylamino)benzoyl | A37 |
| 2,6-dichlorobenzoyl | A38 |
| 2,4,6-trimethylbenzoyl | A39 |
| 4-fluorophenylsulfonyl | A40 |
| phenylsulfonyl | A41 |
| ethylsulfonyl | A42 |

| FRAGMENT | CODE |
|---|---|
| 4-fluoro-2-methylphenyl sulfonyl-M1 | A43 |
| 2,5-difluorophenyl sulfonyl-M1 | A44 |
| methylsulfonyl-M1 | A45 |
| N-phenyl acetamide-M1 | A46 |
| N-(2-methoxyphenyl) acetamide-M1 | A47 |
| N-(4-methylphenyl) acetamide-M1 | A48 |
| N-(4-fluorobenzyl) acetamide-M1 | A49 |
| N-(tetrahydrofuran-2-ylmethyl) acetamide-M1 | A50 |
| N-isobutyl acetamide-M1 | A51 |
| N-methyl acetamide-M1 | A52 |
| N-(2-methoxyethyl) acetamide-M1 | A53 |

| FRAGMENT | CODE |
|---|---|
| N-cyclohexyl acetamide-M1 | A54 |
| H$_2$N-M1 | B1 |
| (dimethylamino)propylamino-M1 | B2 |
| 4-methylpiperazin-1-yl-M1 | B3 |
| N-phenethyl amino-M1 | B4 |
| N-cyclohexyl amino-M1 | B5 |
| N-ethyl amino-M1 | B6 |
| morpholin-4-yl-M1 | B7 |
| pyrrolidin-1-yl-M1 | B8 |
| N-(furan-2-ylmethyl) amino-M1 | B9 |
| N-isopropyl amino-M1 | B10 |
| N,N-dibutyl amino-M1 | B11 |
| N-(1-phenylethyl) amino-M1 | B12 |
| N-[2-(4-chlorophenyl)ethyl] amino-M1 | B13 |

| FRAGMENT | CODE |
|---|---|
| 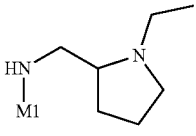 | B14 |
| 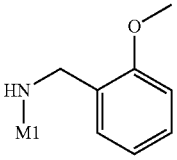 | B15 |
| 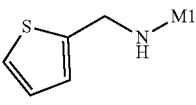 | B16 |
| 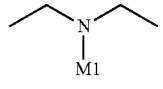 | B17 |
| 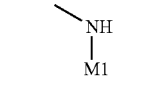 | B18 |
|  | B19 |
| 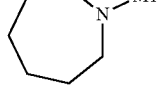 | B20 |
| 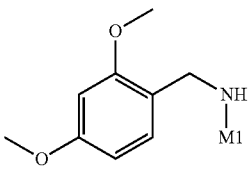 | B21 |
| 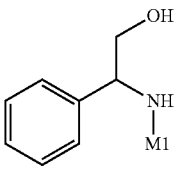 | B22 |
| 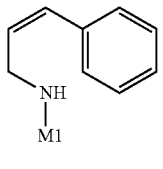 | B23 |
| 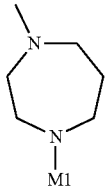 | B24 |
| FRAGMENT | CODE |
|---|---|
| 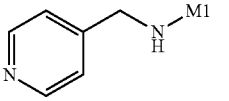 | B25 |
| 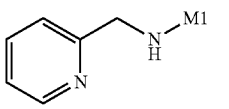 | B26 |
| 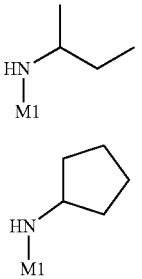 | B27 |
| 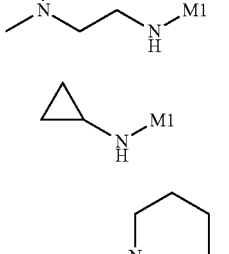 | B28 |
| 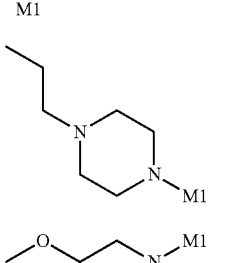 | B29 |
| 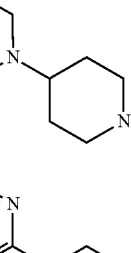 | B30 |
| 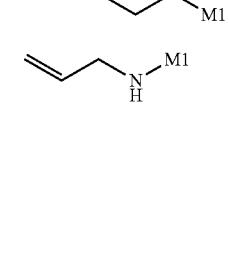 | B31 |
| 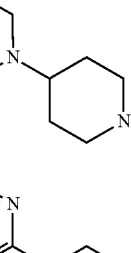 | B32 |
| 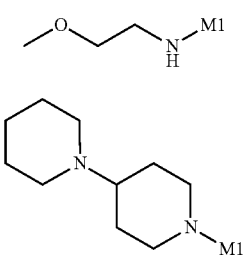 | B33 |
| 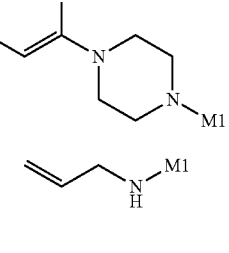 | B34 |
| 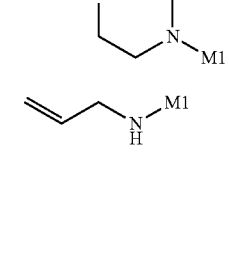 | B35 |
| 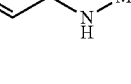 | B36 |

| FRAGMENT | CODE |
|---|---|
| 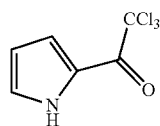 | B37 |
| 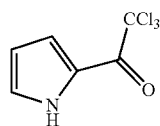 | B38 |
| 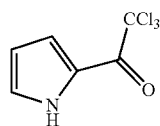 | B39 |
| 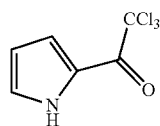 | B40 |
| 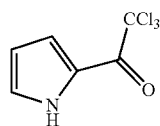 | B41 |
| 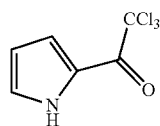 | B42 |
| 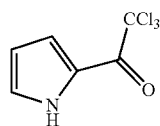 | B43. |

9. A process for preparing a compound of formula (I) as defined in claim 1, characterized in that the process comprises the following steps:

a) reaction of the compound of formula (II):

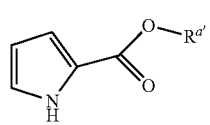

(II)

with an alcohol of formula (III):

$R^{a'}$—OH     (III)

wherein $R^{a'}$ is straight or branched $C_1$-$C_6$ alkyl group;

b) acylation by Friedel-Craft reaction of the resultant compound of formula (IV):

(IV)

wherein $R^{a'}$ is as defined above;

c) reaction of the resultant compound of formula (V):

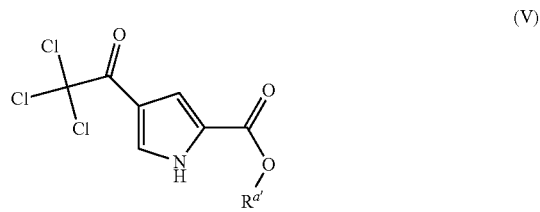

(V)

wherein $R^{a'}$ is as defined above, with a suitable alcohol of formula (III) as defined above;

d) alkylation of the resultant compound of formula (VI):

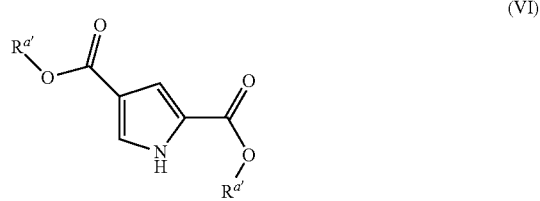

(VI)

wherein both $R^{a'}$, each independently one from the other, are as defined above, with a suitable halo-cyanoalkane of formula (XXI):

(XXI)

wherein n is 0;

e) intramolecular condensation of the resultant compound of formula (VII):

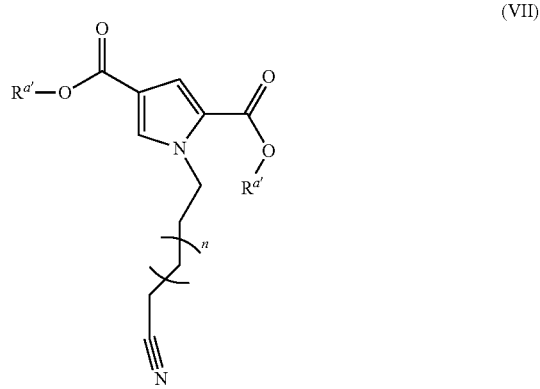

(VII)

wherein n is as defined above and both $R^{a'}$, each independently one from the other, are as defined above;

f) treatment with hydrazine or an hydrazine salt thereof, of the resultant compound of formula (VIII):

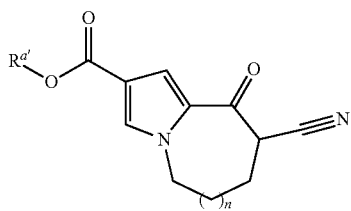

wherein n and $R^{a'}$ are as defined above, to give the compound of formula (I):

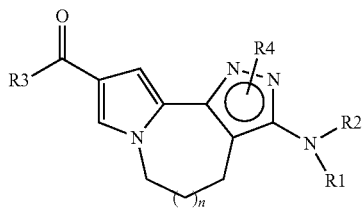

wherein n is 0; R1, R2 and R4 are hydrogen and R3 is —$OR^{a'}$, wherein $R^{a'}$ is a straight or branched $C_1$-$C_6$ alkyl group; optionally separating the resultant compound of formula (I) into the single isomers; and/or converting the resultant compound of formula (I) into a different compound of formula (I) by replacing the group —$OR^{a'}$ with a different group which R3 represents, and/or by introducing the R4 group, and/or by derivatizing the amino moiety, and/or by removing the R4 group, and/or converting it into a pharmaceutically acceptable salt if desired.

10. A process according to claim 9, characterized in that the compound of formula (I)

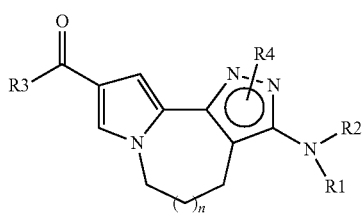

wherein n is 0; R1, R2 and R4 are hydrogen, and R3 is $OR^{a'}$ wherein $R^{a'}$ is straight or branched $C_1$-$C_6$ alkyl group, is optionally converted into a different compound of formula (I) according to one or more of the following reactions:

g) replacing the group —$OR^{a'}$ with a different group which R3 represents, according to any one of the following reactions:

g.1) hydrolysis under basic condition to give the corresponding compound of formula (I) wherein R3 is OH, optionally followed by the coupling of the resultant compound with an amine of formula (IX):

$HNR^aR^b$ (IX)

wherein $R^a$ and $R^b$, the same or different, are each independently hydrogen or a group optionally substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl or, taken together with the nitrogen atom to which they are bonded, either $R^a$ and $R^b$, may form an optionally substituted 3 to 8 membered heterocycle, optionally containing one additional heteroatom or heteroatomic group selected from S, O, N or NH, to give the corresponding compound of formula (I) wherein R3 is —$NR^aR^b$, and $R^a$ and $R^b$ are as defined above, or g.2) transesterification by reactions with a compound of formula (III) as defined above, to give the corresponding compound of formula (I) wherein R3 is $OR^{a'}$ and $R^{a'}$ is a different $C_1$-$C_6$ alkyl, or g.3) coupling with an amine of formula (IX):

$HNR^aR^b$ (IX)

wherein $R^a$ and $R^b$ are as defined above, to give the corresponding compound of formula (I) wherein R3 is —$NR^aR^b$, and $R^a$ and $R^b$ are as defined above; or h) introducing the group R4 into the resultant compound of formula (I):

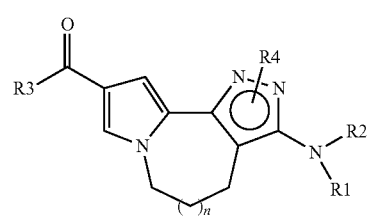

wherein n is defined above and R3 is a group —$NR^aR^b$ or —$OR^a$, and R1, R2 and R4 are hydrogen, according to any one of the following reactions:

h.1) coupling with an equivalent of an halide of formula (X):

$R^aZ$ (X)

wherein $R^a$ is as defined above but not hydrogen and Z is a halogen, to give the corresponding compound of formula (I) wherein R4 is $R^a$, and $R^a$ is as defined above but not hydrogen, or h.2) coupling with an equivalent of an acyl halide of formula (XI):

$R^aCOZ$ (XI)

wherein $R^a$ and Z are as defined above, to give the corresponding compound of formula (I) wherein R4 is —$COR^a$ and $R^a$ is as defined above, or h.3) coupling with an equivalent of an alkoxycarbonyl halide of formula (XII):

$R^aOCOZ$ (XII)

wherein $R^a$ and Z are as defined above, to give the corresponding compound of formula (I) wherein R4 is —$OCOR^a$ and $R^a$ is as defined above, or h.4) coupling with an equivalent of a sulfonyl halide of formula (XIII):

$R^aSO_2Z$ (XIII)

wherein $R^a$ and Z are as defined above, to give the corresponding compound of formula (I) wherein R4 is —SO₂Rᵃ and Rᵃ is as defined above, or h.5) coupling with an equivalent of an isocyanate of formula (XIV):

RᵃNCO (XIV)

wherein Rᵃ is as defined above, to give the corresponding compound of formula (I) wherein R4 is —CONHRᵃ and Rᵃ is as defined above; or i) derivatizing the amino moiety of the resultant compound of formula (I):

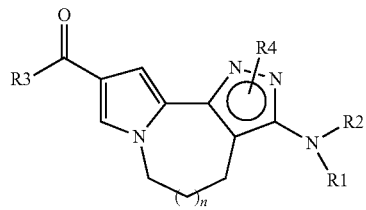

(I)

wherein n and R3 are as defined in formula (I), and R1, R2 and R4 are hydrogen, according to any one of the following reactions:

i.1) coupling with an equivalent of an acyl halide of formula (XI):

RᵃCOZ (XI)

wherein Rᵃ is as defined above and Z is a halogen, to give the corresponding compound of formula (I) wherein one of R1 or R2 is hydrogen and the other one is —CORᵃ and Rᵃ is as defined above, or i.2) coupling with an equivalent of an alkoxycarbonyl halide of formula (XII):

RᵃOCOZ (XII)

wherein Rᵃ and Z are as defined above, to give the corresponding compound of formula (I) wherein one of R1 or R2 is hydrogen and the other one is —OCORᵃ and Rᵃ is as as defined above, or i.3) coupling with an equivalent of a sulfonyl halide of formula (XIII):

RᵃSO₂Z (XIII)

wherein Rᵃ and Z are as defined above, to give the corresponding compound of formula (I) wherein one of R1 or R2 is hydrogen and the other one is —SO₂Rᵃ is as defined above, or i.4) coupling with an equivalent of an isocyanate of formula (XIV):

RᵃNCO (XIV)

wherein Rᵃ is as defined above, to give the corresponding compound of formula (I) wherein one of R1 or R2 is hydrogen and the other one is —CONHRᵃ and Rᵃ is as defined above, or i.5) coupling with an equivalent of a carbonyl compound of formula (XV):

RᵃCORᵇᵉ (XV)

wherein Rᵃ and Rᵇ are as defined above, to give the corresponding compound of formula (I) wherein one of R1 or R2 is hydrogen and the other one is —CORᵃ and Rᵃ is as defined above; or j) further derivatizing the amino moiety of the resultant compound of formula (I):

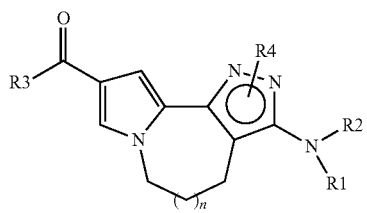

(I)

wherein n and R3 are as defined above; one of R1 and R2 is hydrogen and the other is selected from the group consisting of —Rᵃ, —CORᵃ, —CONHRᵃ, —SO₂Rᵃ and —COORᵃ, but not hydrogen, and R4 is selected from the group consisting of —Rᵃ, —CORᵃ, —CONHRᵃ, —SO₂Rᵃ and —COORᵃ, but not hydrogen, according to any one of the reactions described under steps 1.1) to i.5) above; or k) removing the group R4 from the resultant compound of formula (I):

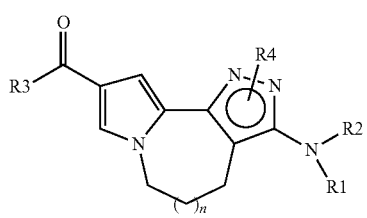

(I)

wherein n, R1, R2 and R3 are as defined above and R4 is as defined above but not hydrogen, by treatment with a basic solution, to obtain the corresponding compound wherein R4 is hydrogen;

optionally separating the resultant compound of formula (I) into the single isomers, and/or converting the resultant compound of formula (I) into a pharmaceutically acceptable salt.

11. A process for preparing a compound of formula (I) as defined in claim 1, or a pharmaceutically acceptable salt thereof, which process comprises the following steps:

l) acylation of the alkoxycarbonyl derivative of formula (I) wherein n is as defined in claim 1;

R1, R2 and R4 are hydrogen, and Rᵃ′ is straight or branched C₁-C₆ alkyl group, with trifluoroacetic anhydride;

m) removal from the resultant compound of formula (I) of the trifluoroacetyl group in position 1 or 2 of the pyrazolo ring;

n) loading of the resultant compound of formula (I) trifluoroacetylated in position 3 onto a resin as suitable solid support;

o) hydrolyzing under acid or basic conditions the resultant compound of formula (XVI)

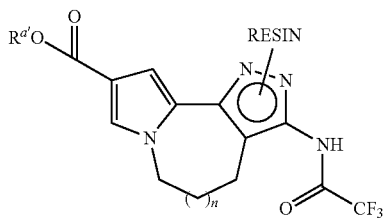

(XVI)

wherein n is as defined in claim 1, $R^{a'}$ is as defined above and the resin is a polystyrenic resin selected from the group consisting of Br-Wang resin, Trityl resin, Cl-trityl resin, Merriefield resin, MAMP resin, isocianate resin and derivatives thereof;

p) coupling the carboxyl group of the resultant compound of formula (XVII):

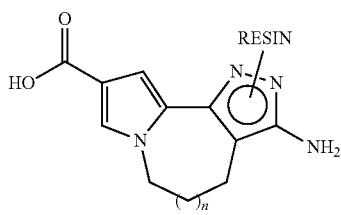

(XVII)

wherein n and the resin are as defined above, with an amine of formula (IX);

$HNR^aR^b$ (IX)

q) derivatizing the amino moiety in position 3 of resultant compound of formula (XVIII):

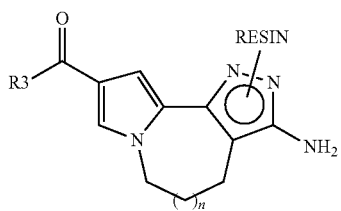

(XVIII)

wherein n and the resin are as defined above, with an amine of formula (IX) as defined above;

r) cleaving the resin from the resultant compound of formula (XIX):

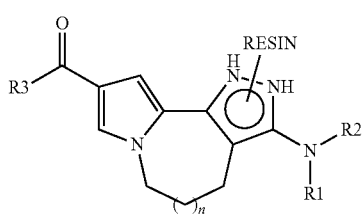

(XIX)

so as to obtain the desired compounds of formula I, optionally converting the resultant compound of formula (I) into a different compound of formula (I) and/or converting it into a pharmaceutically acceptable salt if desired.

12. Two or more compounds of formula (I):

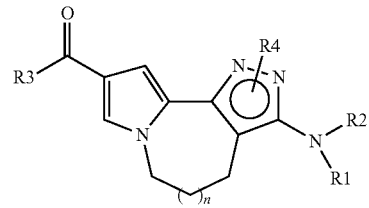

(I)

wherein n is 0;

R1, R2 and R4, each independently one from the other, are selected from the group consisting of —$R^a$, —$COR^a$, —$CONHR^a$, —$SO_2R^a$ and —$COOR^a$;

R3 is a group —$NR^aR^b$ or —$OR^a$;

wherein $R^a$ and $R^b$, the same or different, are each independently hydrogen or a group optionally substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl or, taken together with the nitrogen atom to which they are bonded, either $R^a$ and $R^b$, may form an optionally substituted 3 to 8 membered heterocycle, optionally containing one additional heteroatom or heteroatomic group selected from S, O, N or NH, and pharmaceutically acceptable salts thereof.

13. Two or more compounds according to claim 12, wherein the compounds have the formula:

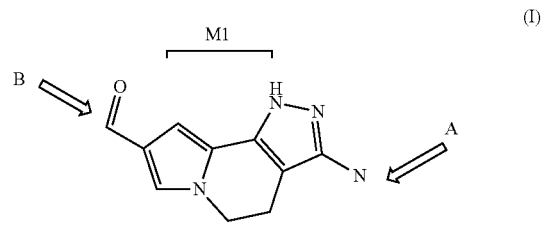

(I)

wherein substituents A and B are:

| FRAGMENT | CODE |
|---|---|
| M1 (benzoyl) | A1 |
| M1 (phenylacetyl) | A2 |

-continued

| FRAGMENT | CODE |
|---|---|
| (cyclopropyl ketone, M1) | A3 |
| (isobutyl ketone, M1) | A4 |
| (2-chlorobenzoyl, M1) | A5 |
| (2-methoxybenzoyl, M1) | A6 |
| (2-thienylacetyl, M1) | A7 |
| (3-fluorobenzoyl, M1) | A8 |
| (2-furoyl, M1) | A9 |
| (3-cyclopentylpropanoyl, M1) | A10 |
| (1,3-benzodioxole-5-carbonyl, M1) | A11 |
| (4-methoxyphenylacetyl, M1) | A12 |

-continued

| FRAGMENT | CODE |
|---|---|
| (2-methylbutanoyl, M1) | A13 |
| (4-methylbenzoyl, M1) | A14 |
| (3-phenylpropanoyl, M1) | A15 |
| (4-(4-methylpiperazin-1-yl)benzoyl, M1) | A16 |
| (3-methoxybenzoyl, M1) | A17 |
| (3-chlorobenzoyl, M1) | A18 |
| (3,4-dimethylbenzoyl, M1) | A19 |
| (2-fluorobenzoyl, M1) | A20 |
| (2-methylbenzoyl, M1) | A21 |

| FRAGMENT | CODE |
|---|---|
| 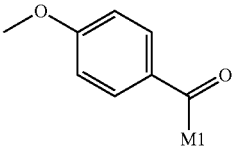 | A22 |
| 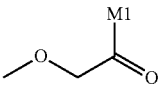 | A23 |
| 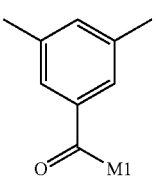 | A24 |
| 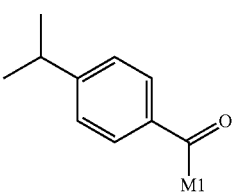 | A25 |
| 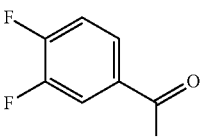 | A26 |
| 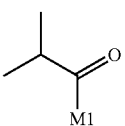 | A27 |
|  | A28 |
|  | A29 |
| 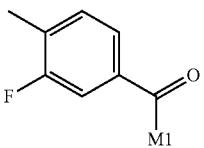 | A30 |
| 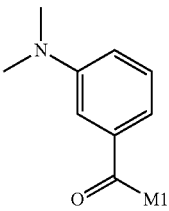 | A31 |
| FRAGMENT | CODE |
|---|---|
| 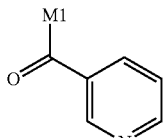 | A32 |
| 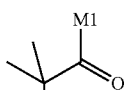 | A33 |
| 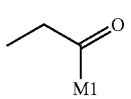 | A34 |
| 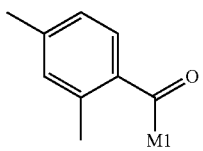 | A35 |
| 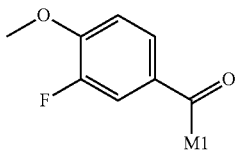 | A36 |
| 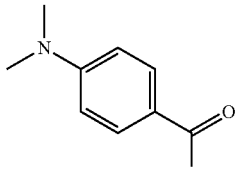 | A37 |
| 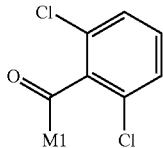 | A38 |
| 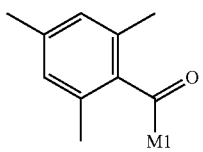 | A39 |
| 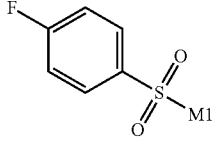 | A40 |
| 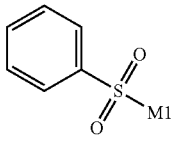 | A41 |

| FRAGMENT | CODE |
|---|---|
| ethylsulfonyl-M1 | A42 |
| 5-fluoro-2-methylphenylsulfonyl-M1 | A43 |
| 2,5-difluorophenylsulfonyl-M1 | A44 |
| methylsulfonyl-M1 | A45 |
| N-phenyl carboxamide-M1 | A46 |
| N-(2-methoxyphenyl) carboxamide-M1 | A47 |
| N-(4-methylphenyl) carboxamide-M1 | A48 |
| N-(4-fluorobenzyl) carboxamide-M1 | A49 |
| N-(tetrahydrofuran-2-ylmethyl) carboxamide-M1 | A50 |
| N-isobutyl carboxamide-M1 | A51 |
| N-methyl carboxamide-M1 | A52 |

| FRAGMENT | CODE |
|---|---|
| N-(2-methoxyethyl) carboxamide-M1 | A53 |
| N-cyclohexyl carboxamide-M1 | A54 |
| H2N-M1 | B1 |
| (CH3)2N-CH2CH2CH2-NH-M1 | B2 |
| 4-methylpiperazin-1-yl-M1 | B3 |
| phenethylamino-M1 | B4 |
| cyclohexylamino-M1 | B5 |
| ethylamino-M1 | B6 |
| morpholin-4-yl-M1 | B7 |
| pyrrolidin-1-yl-M1 | B8 |
| (furan-2-ylmethyl)amino-M1 | B9 |
| isopropylamino-M1 | B10 |
| dibutylamino-M1 | B11 |
| (1-phenylethyl)amino-M1 | B12 |

| FRAGMENT | CODE |
|---|---|
| 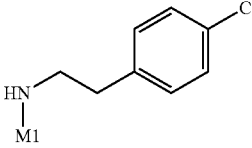 | B13 |
| 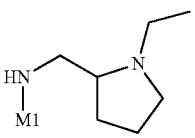 | B14 |
| 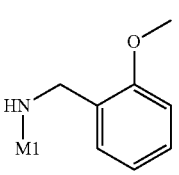 | B15 |
| 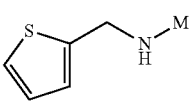 | B16 |
| 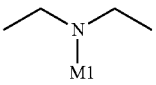 | B17 |
|  | B18 |
|  | B19 |
| 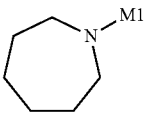 | B20 |
| 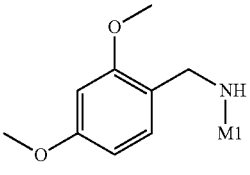 | B21 |
| 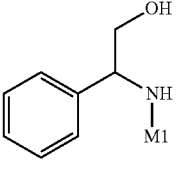 | B22 |
| 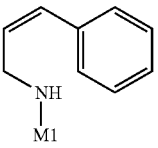 | B23 |
| FRAGMENT | CODE |
|---|---|
| 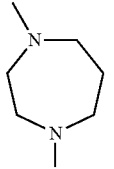 | B24 |
| 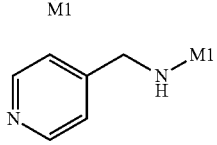 | B25 |
| 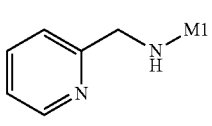 | B26 |
| 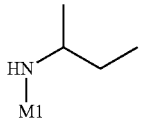 | B27 |
| 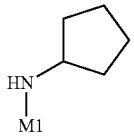 | B28 |
| 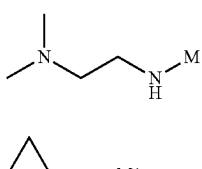 | B29 |
| 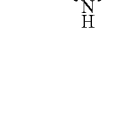 | B30 |
|  | B31 |
| 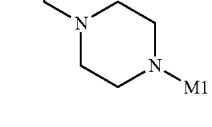 | B32 |
| 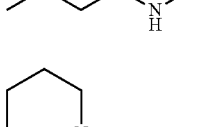 | B33 |
| 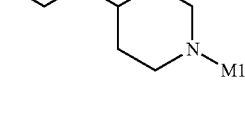 | B34 |

| FRAGMENT | CODE |
|---|---|
| pyridine-piperazine-M1 | B35 |
| allyl-NH-M1 | B36 |
| ethyl-piperazine-M1 | B37 |
| thiomorpholine-M1 | B38 |
| isobutyl-NH-M1 | B39 |
| isopropyl-piperazine-M1 | B40 |
| cyclopropylmethyl-NH-M1 | B41 |
| piperidine-M1 | B42 |
| pyrrolidine-ethyl-NH-M1 | B43, | and wherein the compounds are among those listed herein below:

| Entry | Compound |
|---|---|
| 1 | A1-M1-B1 |
| 2 | A2-M1-B1 |
| 3 | A3-M1-B1 |
| 4 | A1-M1-B2 |
| 5 | A1-M1-B3 |
| 6 | A1-M1-B4 |
| 7 | A1-M1-B5 |
| 8 | A1-M1-B6 |
| 9 | A4-M1-B7 |
| 10 | A5-M1-B8 |
| 11 | A6-M1-B9 |
| 12 | A7-M1-B10 |
| 13 | A8-M1-B11 |
| 14 | A9-M1-B11 |
| 15 | A10-M1-B11 |
| 16 | A11-M1-B11 |
| 17 | A12-M1-B11 |
| 18 | A13-M1-B11 |
| 19 | A14-M1-B12 |
| 20 | A15-M1-B12 |
| 21 | A12-M1-B12 |
| 22 | A13-M1-B12 |
| 23 | A14-M1-B13 |
| 24 | A15-M1-B13 |
| 25 | A8-M1-B13 |
| 26 | A9-M1-B13 |
| 27 | A15-M1-B11 |
| 28 | A8-M1-B12 |
| 29 | A9-M1-B12 |
| 30 | A10-M1-B12 |
| 31 | A11-M1-B12 |
| 32 | A10-M1-B13 |
| 33 | A11-M1-B13 |
| 34 | A12-M1-B13 |
| 35 | A13-M1-B13 |
| 36 | A14-M1-B14 |
| 37 | A15-M1-B14 |
| 38 | A8-M1-B14 |
| 39 | A9-M1-B14 |
| 40 | A10-M1-B14 |
| 41 | A11-M1-B14 |
| 42 | A12-M1-B14 |
| 43 | A13-M1-B14 |
| 44 | A14-M1-B15 |
| 45 | A15-M1-B15 |
| 46 | A8-M1-B15 |
| 47 | A9-M1-B15 |
| 48 | A10-M1-B15 |
| 49 | A11-M1-B15 |
| 50 | A12-M1-B15 |
| 51 | A13-M1-B15 |
| 52 | A14-M1-B16 |
| 53 | A15-M1-B16 |
| 54 | A8-M1-B16 |
| 55 | A13-M1-B16 |
| 56 | A9-M1-B16 |
| 57 | A10-M1-B16 |
| 58 | A11-M1-B16 |
| 59 | A12-M1-B16 |
| 60 | A14-M1-B11 |
| 61 | A16-M1-B10 |
| 62 | A16-M1-B17 |
| 63 | A16-M1-B18 |
| 64 | A16-M1-B19 |
| 65 | A1-M1-B20 |
| 66 | A1-M1-B21 |
| 67 | A1-M1-B22 |
| 68 | A1-M1-B23 |
| 69 | A17-M1-B24 |
| 70 | A18-M1-B24 |
| 71 | A3-M1-B24 |
| 72 | A19-M1-B24 |
| 73 | A20-M1-B24 |
| 74 | A11-M1-B24 |
| 75 | A21-M1-B24 |
| 76 | A22-M1-B24 |
| 77 | A4-M1-B24 |
| 78 | A6-M1-B24 |
| 79 | A23-M1-B24 |
| 80 | A24-M1-B24 |
| 81 | A25-M1-B24 |
| 82 | A26-M1-B24 |
| 83 | A27-M1-B24 |
| 84 | A28-M1-B24 |
| 85 | A29-M1-B24 |
| 86 | A8-M1-B24 |
| 87 | A30-M1-B24 |
| 88 | A17-M1-B25 |
| 89 | A31-M1-B25 |
| 90 | A18-M1-B25 |
| 91 | A3-M1-B25 |
| 92 | A19-M1-B25 |
| 93 | A20-M1-B25 |
| 94 | A32-M1-B25 |
| 95 | A11-M1-B25 |

-continued

| Entry | Compound |
|---|---|
| 96 | A21-M1-B25 |
| 97 | A24-M1-B25 |
| 98 | A26-M1-B25 |
| 99 | A33-M1-B25 |
| 100 | A5-M1-B25 |
| 101 | A27-M1-B25 |
| 102 | A28-M1-B25 |
| 103 | A29-M1-B25 |
| 104 | A1-M1-B25 |
| 105 | A8-M1-B25 |
| 106 | A17-M1-B26 |
| 107 | A31-M1-B26 |
| 108 | A18-M1-B26 |
| 109 | A3-M1-B26 |
| 110 | A19-M1-B26 |
| 111 | A20-M1-B26 |
| 112 | A32-M1-B26 |
| 113 | A11-M1-B26 |
| 114 | A21-M1-B26 |
| 115 | A22-M1-B26 |
| 116 | A6-M1-B26 |
| 117 | A24-M1-B26 |
| 118 | A26-M1-B26 |
| 119 | A33-M1-B26 |
| 120 | A5-M1-B26 |
| 121 | A34-M1-B26 |
| 122 | A27-M1-B26 |
| 123 | A28-M1-B26 |
| 124 | A1-M1-B26 |
| 125 | A8-M1-B26 |
| 126 | A17-M1-B27 |
| 127 | A31-M1-B27 |
| 128 | A18-M1-B27 |
| 129 | A3-M1-B27 |
| 130 | A19-M1-B27 |
| 131 | A20-M1-B27 |
| 132 | A32-M1-B27 |
| 133 | A21-M1-B27 |
| 134 | A6-M1-B27 |
| 135 | A23-M1-B27 |
| 136 | A24-M1-B27 |
| 137 | A25-M1-B27 |
| 138 | A26-M1-B27 |
| 139 | A35-M1-B27 |
| 140 | A33-M1-B27 |
| 141 | A5-M1-B27 |
| 142 | A28-M1-B27 |
| 143 | A1-M1-B27 |
| 144 | A8-M1-B27 |
| 145 | A30-M1-B27 |
| 146 | A17-M1-B28 |
| 147 | A31-M1-B28 |
| 148 | A18-M1-B28 |
| 149 | A3-M1-B28 |
| 150 | A19-M1-B28 |
| 151 | A20-M1-B28 |
| 152 | A32-M1-B28 |
| 153 | A11-M1-B28 |
| 154 | A21-M1-B28 |
| 155 | A4-M1-B28 |
| 156 | A6-M1-B28 |
| 157 | A23-M1-B28 |
| 158 | A24-M1-B28 |
| 159 | A26-M1-B28 |
| 160 | A35-M1-B28 |
| 161 | A36-M1-B28 |
| 162 | A33-M1-B28 |
| 163 | A5-M1-B28 |
| 164 | A28-M1-B28 |
| 165 | A29-M1-B28 |
| 166 | A1-M1-B28 |
| 167 | A8-M1-B28 |
| 168 | A30-M1-B28 |
| 169 | A17-M1-B29 |
| 170 | A18-M1-B29 |
| 171 | A3-M1-B29 |
| 172 | A20-M1-B29 |

-continued

| Entry | Compound |
|---|---|
| 173 | A32-M1-B29 |
| 174 | A11-M1-B29 |
| 175 | A21-M1-B29 |
| 176 | A22-M1-B29 |
| 177 | A4-M1-B29 |
| 178 | A6-M1-B29 |
| 179 | A24-M1-B29 |
| 180 | A26-M1-B29 |
| 181 | A33-M1-B29 |
| 182 | A27-M1-B29 |
| 183 | A28-M1-B29 |
| 184 | A1-M1-B29 |
| 185 | A8-M1-B29 |
| 186 | A17-M1-B8 |
| 187 | A18-M1-B8 |
| 188 | A3-M1-B8 |
| 189 | A19-M1-B8 |
| 190 | A20-M1-B8 |
| 191 | A32-M1-B8 |
| 192 | A11-M1-B8 |
| 193 | A21-M1-B8 |
| 194 | A22-M1-B8 |
| 195 | A4-M1-B8 |
| 196 | A6-M1-B8 |
| 197 | A24-M1-B8 |
| 198 | A25-M1-B8 |
| 199 | A26-M1-B8 |
| 200 | A35-M1-B8 |
| 201 | A36-M1-B8 |
| 202 | A33-M1-B8 |
| 203 | A34-M1-B8 |
| 204 | A27-M1-B8 |
| 205 | A28-M1-B8 |
| 206 | A8-M1-B8 |
| 207 | A30-M1-B8 |
| 208 | A17-M1-B10 |
| 209 | A31-M1-B10 |
| 210 | A18-M1-B10 |
| 211 | A3-M1-B10 |
| 212 | A19-M1-B10 |
| 213 | A20-M1-B10 |
| 214 | A32-M1-B10 |
| 215 | A11-M1-B10 |
| 216 | A22-M1-B10 |
| 217 | A6-M1-B10 |
| 218 | A24-M1-B10 |
| 219 | A25-M1-B10 |
| 220 | A26-M1-B10 |
| 221 | A35-M1-B10 |
| 222 | A36-M1-B10 |
| 223 | A33-M1-B10 |
| 224 | A5-M1-B10 |
| 225 | A27-M1-B10 |
| 226 | A28-M1-B10 |
| 227 | A1-M1-B10 |
| 228 | A8-M1-B10 |
| 229 | A30-M1-B10 |
| 230 | A17-M1-B17 |
| 231 | A31-M1-B17 |
| 232 | A18-M1-B17 |
| 233 | A3-M1-B17 |
| 234 | A19-M1-B17 |
| 235 | A20-M1-B17 |
| 236 | A32-M1-B17 |
| 237 | A11-M1-B17 |
| 238 | A21-M1-B17 |
| 239 | A4-M1-B17 |
| 240 | A6-M1-B17 |
| 241 | A24-M1-B17 |
| 242 | A25-M1-B17 |
| 243 | A26-M1-B17 |
| 244 | A36-M1-B17 |
| 245 | A33-M1-B17 |
| 246 | A5-M1-B17 |
| 247 | A27-M1-B17 |
| 248 | A28-M1-B17 |
| 249 | A1-M1-B17 |

-continued

| Entry | Compound |
|---|---|
| 250 | A8-M1-B17 |
| 251 | A30-M1-B17 |
| 252 | A17-M1-B30 |
| 253 | A31-M1-B30 |
| 254 | A19-M1-B30 |
| 255 | A20-M1-B30 |
| 256 | A32-M1-B30 |
| 257 | A21-M1-B30 |
| 258 | A22-M1-B30 |
| 259 | A4-M1-B30 |
| 260 | A24-M1-B30 |
| 261 | A25-M1-B30 |
| 262 | A26-M1-B30 |
| 263 | A35-M1-B30 |
| 264 | A36-M1-B30 |
| 265 | A33-M1-B30 |
| 266 | A5-M1-B30 |
| 267 | A28-M1-B30 |
| 268 | A1-M1-B30 |
| 269 | A8-M1-B30 |
| 270 | A30-M1-B30 |
| 271 | A17-M1-B3 |
| 272 | A31-M1-B3 |
| 273 | A18-M1-B3 |
| 274 | A3-M1-B3 |
| 275 | A37-M1-B3 |
| 276 | A19-M1-B3 |
| 277 | A20-M1-B3 |
| 278 | A32-M1-B3 |
| 279 | A11-M1-B3 |
| 280 | A21-M1-B3 |
| 281 | A22-M1-B3 |
| 282 | A4-M1-B3 |
| 283 | A6-M1-B3 |
| 284 | A24-M1-B3 |
| 285 | A25-M1-B3 |
| 286 | A26-M1-B3 |
| 287 | A36-M1-B3 |
| 288 | A34-M1-B3 |
| 289 | A27-M1-B3 |
| 290 | A28-M1-B3 |
| 291 | A29-M1-B3 |
| 292 | A8-M1-B3 |
| 293 | A30-M1-B3 |
| 294 | A17-M1-B7 |
| 295 | A31-M1-B7 |
| 296 | A3-M1-B7 |
| 297 | A19-M1-B7 |
| 298 | A20-M1-B7 |
| 299 | A32-M1-B7 |
| 300 | A11-M1-B7 |
| 301 | A21-M1-B7 |
| 302 | A22-M1-B7 |
| 303 | A6-M1-B7 |
| 304 | A24-M1-B7 |
| 305 | A25-M1-B7 |
| 306 | A26-M1-B7 |
| 307 | A35-M1-B7 |
| 308 | A36-M1-B7 |
| 309 | A33-M1-B7 |
| 310 | A5-M1-B7 |
| 311 | A34-M1-B7 |
| 312 | A27-M1-B7 |
| 313 | A28-M1-B7 |
| 314 | A29-M1-B7 |
| 315 | A8-M1-B7 |
| 316 | A30-M1-B7 |
| 317 | A17-M1-B31 |
| 318 | A31-M1-B31 |
| 319 | A18-M1-B31 |
| 320 | A3-M1-B31 |
| 321 | A19-M1-B31 |
| 322 | A20-M1-B31 |
| 323 | A32-M1-B31 |
| 324 | A11-M1-B31 |
| 325 | A21-M1-B31 |
| 326 | A22-M1-B31 |

-continued

| Entry | Compound |
|---|---|
| 327 | A4-M1-B31 |
| 328 | A24-M1-B31 |
| 329 | A26-M1-B31 |
| 330 | A33-M1-B31 |
| 331 | A5-M1-B31 |
| 332 | A27-M1-B31 |
| 333 | A28-M1-B31 |
| 334 | A29-M1-B31 |
| 335 | A1-M1-B31 |
| 336 | A8-M1-B31 |
| 337 | A17-M1-B32 |
| 338 | A31-M1-B32 |
| 339 | A18-M1-B32 |
| 340 | A37-M1-B32 |
| 341 | A19-M1-B32 |
| 342 | A20-M1-B32 |
| 343 | A32-M1-B32 |
| 344 | A11-M1-B32 |
| 345 | A21-M1-B32 |
| 346 | A4-M1-B32 |
| 347 | A6-M1-B32 |
| 348 | A24-M1-B32 |
| 349 | A25-M1-B32 |
| 350 | A26-M1-B32 |
| 351 | A35-M1-B32 |
| 352 | A36-M1-B32 |
| 353 | A33-M1-B32 |
| 354 | A5-M1-B32 |
| 355 | A27-M1-B32 |
| 356 | A28-M1-B32 |
| 357 | A1-M1-B32 |
| 358 | A8-M1-B32 |
| 359 | A30-M1-B32 |
| 360 | A17-M1-B33 |
| 361 | A31-M1-B33 |
| 362 | A3-M1-B33 |
| 363 | A19-M1-B33 |
| 364 | A20-M1-B33 |
| 365 | A32-M1-B33 |
| 366 | A11-M1-B33 |
| 367 | A21-M1-B33 |
| 368 | A22-M1-B33 |
| 369 | A4-M1-B33 |
| 370 | A24-M1-B33 |
| 371 | A25-M1-B33 |
| 372 | A26-M1-B33 |
| 373 | A35-M1-B33 |
| 374 | A36-M1-B33 |
| 375 | A33-M1-B33 |
| 376 | A5-M1-B33 |
| 377 | A27-M1-B33 |
| 378 | A28-M1-B33 |
| 379 | A1-M1-B33 |
| 380 | A8-M1-B33 |
| 381 | A30-M1-B33 |
| 382 | A17-M1-B34 |
| 383 | A31-M1-B34 |
| 384 | A18-M1-B34 |
| 385 | A3-M1-B34 |
| 386 | A19-M1-B34 |
| 387 | A20-M1-B34 |
| 388 | A32-M1-B34 |
| 389 | A11-M1-B34 |
| 390 | A21-M1-B34 |
| 391 | A22-M1-B34 |
| 392 | A4-M1-B34 |
| 393 | A6-M1-B34 |
| 394 | A24-M1-B34 |
| 395 | A25-M1-B34 |
| 396 | A26-M1-B34 |
| 397 | A35-M1-B34 |
| 398 | A36-M1-B34 |
| 399 | A33-M1-B34 |
| 400 | A5-M1-B34 |
| 401 | A27-M1-B34 |
| 402 | A28-M1-B34 |
| 403 | A29-M1-B34 |

| Entry | Compound |
|---|---|
| 404 | A8-M1-B34 |
| 405 | A30-M1-B34 |
| 406 | A17-M1-B35 |
| 407 | A31-M1-B35 |
| 408 | A18-M1-B35 |
| 409 | A37-M1-B35 |
| 410 | A19-M1-B35 |
| 411 | A32-M1-B35 |
| 412 | A11-M1-B35 |
| 413 | A22-M1-B35 |
| 414 | A4-M1-B35 |
| 415 | A6-M1-B35 |
| 416 | A25-M1-B35 |
| 417 | A26-M1-B35 |
| 418 | A35-M1-B35 |
| 419 | A36-M1-B35 |
| 420 | A5-M1-B35 |
| 421 | A27-M1-B35 |
| 422 | A28-M1-B35 |
| 423 | A29-M1-B35 |
| 424 | A1-M1-B35 |
| 425 | A8-M1-B35 |
| 426 | A30-M1-B35 |
| 427 | A17-M1-B36 |
| 428 | A31-M1-B36 |
| 429 | A18-M1-B36 |
| 430 | A3-M1-B36 |
| 431 | A19-M1-B36 |
| 432 | A32-M1-B36 |
| 433 | A11-M1-B36 |
| 434 | A21-M1-B36 |
| 435 | A22-M1-B36 |
| 436 | A6-M1-B36 |
| 437 | A24-M1-B36 |
| 438 | A25-M1-B36 |
| 439 | A26-M1-B36 |
| 440 | A35-M1-B36 |
| 441 | A36-M1-B36 |
| 442 | A33-M1-B36 |
| 443 | A5-M1-B36 |
| 444 | A34-M1-B36 |
| 445 | A27-M1-B36 |
| 446 | A28-M1-B36 |
| 447 | A1-M1-B36 |
| 448 | A8-M1-B36 |
| 449 | A30-M1-B36 |
| 450 | A17-M1-B37 |
| 451 | A31-M1-B37 |
| 452 | A18-M1-B37 |
| 453 | A3-M1-B37 |
| 454 | A19-M1-B37 |
| 455 | A20-M1-B37 |
| 456 | A32-M1-B37 |
| 457 | A11-M1-B37 |
| 458 | A21-M1-B37 |
| 459 | A22-M1-B37 |
| 460 | A4-M1-B37 |
| 461 | A6-M1-B37 |
| 462 | A24-M1-B37 |
| 463 | A25-M1-B37 |
| 464 | A26-M1-B37 |
| 465 | A36-M1-B37 |
| 466 | A33-M1-B37 |
| 467 | A5-M1-B37 |
| 468 | A27-M1-B37 |
| 469 | A28-M1-B37 |
| 470 | A29-M1-B37 |
| 471 | A8-M1-B37 |
| 472 | A30-M1-B37 |
| 473 | A17-M1-B38 |
| 474 | A31-M1-B38 |
| 475 | A3-M1-B38 |
| 476 | A19-M1-B38 |
| 477 | A20-M1-B38 |
| 478 | A32-M1-B38 |
| 479 | A11-M1-B38 |
| 480 | A21-M1-B38 |
| 481 | A22-M1-B38 |
| 482 | A4-M1-B38 |
| 483 | A6-M1-B38 |
| 484 | A24-M1-B38 |
| 485 | A25-M1-B38 |
| 486 | A26-M1-B38 |
| 487 | A35-M1-B38 |
| 488 | A36-M1-B38 |
| 489 | A5-M1-B38 |
| 490 | A27-M1-B38 |
| 491 | A28-M1-B38 |
| 492 | A1-M1-B38 |
| 493 | A8-M1-B38 |
| 494 | A30-M1-B38 |
| 495 | A17-M1-B39 |
| 496 | A31-M1-B39 |
| 497 | A3-M1-B39 |
| 498 | A19-M1-B39 |
| 499 | A20-M1-B39 |
| 500 | A32-M1-B39 |
| 501 | A11-M1-B39 |
| 502 | A21-M1-B39 |
| 503 | A22-M1-B39 |
| 504 | A4-M1-B39 |
| 505 | A6-M1-B39 |
| 506 | A24-M1-B39 |
| 507 | A25-M1-B39 |
| 508 | A26-M1-B39 |
| 509 | A35-M1-B39 |
| 510 | A36-M1-B39 |
| 511 | A33-M1-B39 |
| 512 | A5-M1-B39 |
| 513 | A34-M1-B39 |
| 514 | A27-M1-B39 |
| 515 | A28-M1-B39 |
| 516 | A1-M1-B39 |
| 517 | A8-M1-B39 |
| 518 | A30-M1-B39 |
| 519 | A17-M1-B40 |
| 520 | A31-M1-B40 |
| 521 | A3-M1-B40 |
| 522 | A19-M1-B40 |
| 523 | A20-M1-B40 |
| 524 | A32-M1-B40 |
| 525 | A11-M1-B40 |
| 526 | A21-M1-B40 |
| 527 | A22-M1-B40 |
| 528 | A4-M1-B40 |
| 529 | A6-M1-B40 |
| 530 | A24-M1-B40 |
| 531 | A25-M1-B40 |
| 532 | A26-M1-B40 |
| 533 | A35-M1-B40 |
| 534 | A36-M1-B40 |
| 535 | A33-M1-B40 |
| 536 | A5-M1-B40 |
| 537 | A34-M1-B40 |
| 538 | A27-M1-B40 |
| 539 | A28-M1-B40 |
| 540 | A29-M1-B40 |
| 541 | A1-M1-B40 |
| 542 | A8-M1-B40 |
| 543 | A30-M1-B40 |
| 544 | A17-M1-B41 |
| 545 | A31-M1-B41 |
| 546 | A18-M1-B41 |
| 547 | A3-M1-B41 |
| 548 | A19-M1-B41 |
| 549 | A20-M1-B41 |
| 550 | A32-M1-B41 |
| 551 | A11-M1-B41 |
| 552 | A21-M1-B41 |
| 553 | A22-M1-B41 |
| 554 | A4-M1-B41 |
| 555 | A6-M1-B41 |
| 556 | A24-M1-B41 |
| 557 | A25-M1-B41 |

-continued

| Entry | Compound |
|---|---|
| 558 | A26-M1-B41 |
| 559 | A35-M1-B41 |
| 560 | A33-M1-B41 |
| 561 | A5-M1-B41 |
| 562 | A27-M1-B41 |
| 563 | A28-M1-B41 |
| 564 | A1-M1-B41 |
| 565 | A30-M1-B41 |
| 566 | A17-M1-B42 |
| 567 | A18-M1-B42 |
| 568 | A19-M1-B42 |
| 569 | A32-M1-B42 |
| 570 | A11-M1-B42 |
| 571 | A22-M1-B42 |
| 572 | A4-M1-B42 |
| 573 | A24-M1-B42 |
| 574 | A25-M1-B42 |
| 575 | A26-M1-B42 |
| 576 | A35-M1-B42 |
| 577 | A36-M1-B42 |
| 578 | A5-M1-B42 |
| 579 | A34-M1-B42 |
| 580 | A27-M1-B42 |
| 581 | A28-M1-B42 |
| 582 | A1-M1-B42 |
| 583 | A8-M1-B42 |
| 584 | A30-M1-B42 |
| 585 | A17-M1-B6 |
| 586 | A31-M1-B6 |
| 587 | A18-M1-B6 |
| 588 | A3-M1-B6 |
| 589 | A19-M1-B6 |
| 590 | A20-M1-B6 |
| 591 | A32-M1-B6 |
| 592 | A11-M1-B6 |
| 593 | A6-M1-B6 |
| 594 | A24-M1-B6 |
| 595 | A25-M1-B6 |
| 596 | A26-M1-B6 |
| 597 | A35-M1-B6 |
| 598 | A36-M1-B6 |
| 599 | A33-M1-B6 |
| 600 | A5-M1-B6 |
| 601 | A28-M1-B6 |
| 602 | A8-M1-B6 |
| 603 | A30-M1-B6 |
| 604 | A17-M1-B43 |
| 605 | A18-M1-B43 |
| 606 | A19-M1-B43 |
| 607 | A32-M1-B43 |
| 608 | A11-M1-B43 |
| 609 | A21-M1-B43 |
| 610 | A22-M1-B43 |
| 611 | A6-M1-B43 |
| 612 | A24-M1-B43 |
| 613 | A26-M1-B43 |
| 614 | A33-M1-B43 |
| 615 | A5-M1-B43 |
| 616 | A28-M1-B43 |
| 617 | A1-M1-B43 |
| 618 | A8-M1-B43 |
| 619 | A38-M1-B41 |
| 620 | A39-M1-B8 |
| 621 | A39-M1-B34 |
| 1190 | A40-M1-B11 |
| 1191 | A41-M1-B24 |
| 1192 | A42-M1-B24 |
| 1193 | A43-M1-B24 |
| 1194 | A44-M1-B24 |
| 1195 | A45-M1-B25 |
| 1196 | A42-M1-B25 |
| 1197 | A45-M1-B26 |
| 1198 | A42-M1-B26 |
| 1199 | A44-M1-B26 |
| 1200 | A45-M1-B27 |
| 1201 | A41-M1-B27 |
| 1202 | A42-M1-B27 |

-continued

| Entry | Compound |
|---|---|
| 1203 | A43-M1-B27 |
| 1204 | A44-M1-B27 |
| 1205 | A45-M1-B28 |
| 1206 | A41-M1-B28 |
| 1207 | A42-M1-B28 |
| 1208 | A43-M1-B28 |
| 1209 | A44-M1-B28 |
| 1210 | A42-M1-B29 |
| 1211 | A44-M1-B29 |
| 1212 | A45-M1-B8 |
| 1213 | A41-M1-B8 |
| 1214 | A42-M1-B8 |
| 1215 | A43-M1-B8 |
| 1216 | A44-M1-B8 |
| 1217 | A45-M1-B10 |
| 1218 | A41-M1-B10 |
| 1219 | A42-M1-B10 |
| 1220 | A43-M1-B10 |
| 1221 | A44-M1-B10 |
| 1222 | A45-M1-B17 |
| 1223 | A41-M1-B17 |
| 1224 | A42-M1-B17 |
| 1225 | A43-M1-B17 |
| 1226 | A44-M1-B17 |
| 1227 | A45-M1-B30 |
| 1228 | A42-M1-B30 |
| 1229 | A43-M1-B30 |
| 1230 | A44-M1-B30 |
| 1231 | A41-M1-B3 |
| 1232 | A42-M1-B3 |
| 1233 | A43-M1-B3 |
| 1234 | A44-M1-B3 |
| 1235 | A45-M1-B7 |
| 1236 | A41-M1-B7 |
| 1237 | A42-M1-B7 |
| 1238 | A43-M1-B7 |
| 1239 | A44-M1-B7 |
| 1240 | A44-M1-B31 |
| 1241 | A45-M1-B32 |
| 1242 | A41-M1-B32 |
| 1243 | A42-M1-B32 |
| 1244 | A43-M1-B32 |
| 1245 | A44-M1-B32 |
| 1246 | A41-M1-B33 |
| 1247 | A42-M1-B33 |
| 1248 | A43-M1-B33 |
| 1249 | A44-M1-B33 |
| 1250 | A41-M1-B34 |
| 1251 | A43-M1-B34 |
| 1252 | A44-M1-B34 |
| 1253 | A45-M1-B35 |
| 1254 | A41-M1-B35 |
| 1255 | A42-M1-B35 |
| 1256 | A43-M1-B35 |
| 1257 | A44-M1-B35 |
| 1258 | A45-M1-B36 |
| 1259 | A41-M1-B36 |
| 1260 | A42-M1-B36 |
| 1261 | A43-M1-B36 |
| 1262 | A44-M1-B36 |
| 1263 | A41-M1-B37 |
| 1264 | A42-M1-B37 |
| 1265 | A43-M1-B37 |
| 1266 | A44-M1-B37 |
| 1267 | A45-M1-B38 |
| 1268 | A41-M1-B38 |
| 1269 | A42-M1-B38 |
| 1270 | A43-M1-B38 |
| 1271 | A44-M1-B38 |
| 1272 | A45-M1-B39 |
| 1273 | A41-M1-B39 |
| 1274 | A42-M1-B39 |
| 1275 | A43-M1-B39 |
| 1276 | A44-M1-B39 |
| 1277 | A45-M1-B40 |
| 1278 | A41-M1-B40 |
| 1279 | A42-M1-B40 |

103
-continued

| Entry | Compound |
|---|---|
| 1280 | A43-M1-B40 |
| 1281 | A44-M1-B40 |
| 1282 | A45-M1-B41 |
| 1283 | A41-M1-B41 |
| 1284 | A42-M1-B41 |
| 1285 | A43-M1-B41 |
| 1286 | A44-M1-B41 |
| 1287 | A45-M1-B42 |
| 1288 | A41-M1-B42 |
| 1289 | A42-M1-B42 |
| 1290 | A44-M1-B42 |
| 1291 | A41-M1-B6 |
| 1292 | A42-M1-B6 |
| 1293 | A43-M1-B6 |
| 1294 | A44-M1-B6 |
| 1295 | A42-M1-B43 |
| 1296 | A44-M1-B43 |
| 1297 | A46-M1-B24 |
| 1298 | A47-M1-B24 |
| 1299 | A48-M1-B24 |
| 1300 | A49-M1-B24 |
| 1301 | A50-M1-B24 |
| 1302 | A51-M1-B24 |
| 1303 | A52-M1-B24 |
| 1304 | A53-M1-B24 |
| 1305 | A54-M1-B25 |
| 1306 | A48-M1-B25 |
| 1307 | A49-M1-B25 |
| 1308 | A50-M1-B25 |
| 1309 | A51-M1-B25 |
| 1310 | A52-M1-B25 |
| 1311 | A53-M1-B25 |
| 1312 | A54-M1-B26 |
| 1313 | A46-M1-B26 |
| 1314 | A47-M1-B26 |
| 1315 | A48-M1-B26 |
| 1316 | A49-M1-B26 |
| 1317 | A50-M1-B26 |
| 1318 | A51-M1-B26 |
| 1319 | A52-M1-B26 |
| 1320 | A53-M1-B26 |
| 1321 | A54-M1-B27 |
| 1322 | A46-M1-B27 |
| 1323 | A47-M1-B27 |
| 1324 | A48-M1-B27 |
| 1325 | A49-M1-B27 |
| 1326 | A50-M1-B27 |
| 1327 | A51-M1-B27 |
| 1328 | A52-M1-B27 |
| 1329 | A53-M1-B27 |
| 1330 | A54-M1-B28 |
| 1331 | A46-M1-B28 |
| 1332 | A47-M1-B28 |
| 1333 | A48-M1-B28 |
| 1334 | A49-M1-B28 |
| 1335 | A50-M1-B28 |
| 1336 | A51-M1-B28 |
| 1337 | A52-M1-B28 |
| 1338 | A53-M1-B28 |
| 1339 | A54-M1-B29 |
| 1340 | A47-M1-B29 |
| 1341 | A48-M1-B29 |
| 1342 | A49-M1-B29 |
| 1343 | A50-M1-B29 |
| 1344 | A51-M1-B29 |
| 1345 | A53-M1-B29 |
| 1346 | A54-M1-B8 |
| 1347 | A46-M1-B8 |
| 1348 | A48-M1-B8 |
| 1349 | A49-M1-B8 |
| 1350 | A50-M1-B8 |
| 1351 | A51-M1-B8 |
| 1352 | A52-M1-B8 |
| 1353 | A53-M1-B8 |
| 1354 | A46-M1-B10 |
| 1355 | A47-M1-B10 |
| 1356 | A48-M1-B10 |

104
-continued

| Entry | Compound |
|---|---|
| 1357 | A49-M1-B10 |
| 1358 | A50-M1-B10 |
| 1359 | A51-M1-B10 |
| 1360 | A52-M1-B10 |
| 1361 | A53-M1-B10 |
| 1362 | A54-M1-B17 |
| 1363 | A46-M1-B17 |
| 1364 | A47-M1-B17 |
| 1365 | A48-M1-B17 |
| 1366 | A49-M1-B17 |
| 1367 | A50-M1-B17 |
| 1368 | A51-M1-B17 |
| 1369 | A53-M1-B17 |
| 1370 | A47-M1-B30 |
| 1371 | A48-M1-B30 |
| 1372 | A49-M1-B30 |
| 1373 | A50-M1-B30 |
| 1374 | A51-M1-B30 |
| 1375 | A52-M1-B30 |
| 1376 | A53-M1-B30 |
| 1377 | A54-M1-B3 |
| 1378 | A46-M1-B3 |
| 1379 | A47-M1-B3 |
| 1380 | A48-M1-B3 |
| 1381 | A49-M1-B3 |
| 1382 | A50-M1-B3 |
| 1383 | A51-M1-B3 |
| 1384 | A52-M1-B3 |
| 1385 | A53-M1-B3 |
| 1386 | A54-M1-B7 |
| 1387 | A46-M1-B7 |
| 1388 | A48-M1-B7 |
| 1389 | A49-M1-B7 |
| 1390 | A50-M1-B7 |
| 1391 | A51-M1-B7 |
| 1392 | A52-M1-B7 |
| 1393 | A53-M1-B7 |
| 1394 | A54-M1-B31 |
| 1395 | A46-M1-B31 |
| 1396 | A47-M1-B31 |
| 1397 | A48-M1-B31 |
| 1398 | A49-M1-B31 |
| 1399 | A50-M1-B31 |
| 1400 | A51-M1-B31 |
| 1401 | A52-M1-B31 |
| 1402 | A53-M1-B31 |
| 1403 | A54-M1-B32 |
| 1404 | A46-M1-B32 |
| 1405 | A47-M1-B32 |
| 1406 | A48-M1-B32 |
| 1407 | A52-M1-B32 |
| 1408 | A53-M1-B32 |
| 1409 | A54-M1-B33 |
| 1410 | A47-M1-B33 |
| 1411 | A48-M1-B33 |
| 1412 | A49-M1-B33 |
| 1413 | A50-M1-B33 |
| 1414 | A51-M1-B33 |
| 1415 | A52-M1-B33 |
| 1416 | A53-M1-B33 |
| 1417 | A54-M1-B34 |
| 1418 | A47-M1-B34 |
| 1419 | A48-M1-B34 |
| 1420 | A49-M1-B34 |
| 1421 | A50-M1-B34 |
| 1422 | A51-M1-B34 |
| 1423 | A52-M1-B34 |
| 1424 | A53-M1-B34 |
| 1425 | A54-M1-B35 |
| 1426 | A48-M1-B35 |
| 1427 | A49-M1-B35 |
| 1428 | A50-M1-B35 |
| 1429 | A51-M1-B35 |
| 1430 | A52-M1-B35 |
| 1431 | A53-M1-B35 |
| 1432 | A47-M1-B36 |
| 1433 | A48-M1-B36 |

| Entry | Compound |
|---|---|
| 1434 | A49-M1-B36 |
| 1435 | A50-M1-B36 |
| 1436 | A51-M1-B36 |
| 1437 | A52-M1-B36 |
| 1438 | A53-M1-B36 |
| 1439 | A54-M1-B37 |
| 1440 | A47-M1-B37 |
| 1441 | A48-M1-B37 |
| 1442 | A49-M1-B37 |
| 1443 | A50-M1-B37 |
| 1444 | A51-M1-B37 |
| 1445 | A52-M1-B37 |
| 1446 | A53-M1-B37 |
| 1447 | A54-M1-B38 |
| 1448 | A46-M1-B38 |
| 1449 | A48-M1-B38 |
| 1450 | A49-M1-B38 |
| 1451 | A50-M1-B38 |
| 1452 | A51-M1-B38 |
| 1453 | A52-M1-B38 |
| 1454 | A53-M1-B38 |
| 1455 | A54-M1-B39 |
| 1456 | A46-M1-B39 |
| 1457 | A47-M1-B39 |
| 1458 | A48-M1-B39 |
| 1459 | A49-M1-B39 |
| 1460 | A50-M1-B39 |
| 1461 | A51-M1-B39 |
| 1462 | A52-M1-B39 |
| 1463 | A53-M1-B39 |
| 1464 | A54-M1-B40 |
| 1465 | A47-M1-B40 |
| 1466 | A48-M1-B40 |
| 1467 | A49-M1-B40 |
| 1468 | A50-M1-B40 |
| 1469 | A51-M1-B40 |
| 1470 | A52-M1-B40 |
| 1471 | A53-M1-B40 |
| 1472 | A54-M1-B41 |
| 1473 | A46-M1-B41 |
| 1474 | A47-M1-B41 |
| 1475 | A48-M1-B41 |
| 1476 | A49-M1-B41 |
| 1477 | A50-M1-B41 |
| 1478 | A51-M1-B41 |
| 1479 | A52-M1-B41 |
| 1480 | A53-M1-B41 |
| 1481 | A54-M1-B41 |
| 1482 | A46-M1-B42 |
| 1483 | A48-M1-B42 |
| 1484 | A49-M1-B42 |
| 1485 | A50-M1-B42 |
| 1486 | A51-M1-B42 |
| 1487 | A52-M1-B42 |
| 1488 | A53-M1-B42 |
| 1489 | A46-M1-B6 |
| 1490 | A47-M1-B6 |
| 1491 | A48-M1-B6 |
| 1492 | A49-M1-B6 |
| 1493 | A50-M1-B6 |
| 1494 | A51-M1-B6 |
| 1495 | A52-M1-B6 |
| 1496 | A53-M1-B6 |
| 1497 | A54-M1-B43 |
| 1498 | A48-M1-B43 |
| 1499 | A49-M1-B43 |
| 1500 | A51-M1-B43 |
| 1501 | A53-M1-B43. |

14. A method for treating a disease caused by and/or associated with a dysregulated protein kinase activity, selected from the group consisting of breast carcinoma, ovarian carcinoma and fibrosarcoma, which comprises administering to a mammal in need thereof an effective amount of a compound of formula (I) as defined in claim 1.

15. A pharmaceutical composition comprising a therapeutically effective amount of a compound of formula (I) as defined in claim 1, and, at least, one pharmaceutically acceptable excipient, carrier and/or diluent.

* * * * *